(12) United States Patent
Wang et al.

(10) Patent No.: US 9,182,352 B2
(45) Date of Patent: **\*Nov. 10, 2015**

(54) SYSTEM AND METHOD FOR DETECTING OIL OR GAS UNDERGROUND USING LIGHT SCATTERING SPECTRAL ANALYSES

(71) Applicant: OptoTrace (Suzhou) Technologies, Inc., SuZhou (CN)

(72) Inventors: Hong Wang, Cupertino, CA (US); Xun Guo, San Jose, CA (US); Xue Zhong, SuZhou (CN); Dong Zhang, SuZhou (CN); Chunwei Liu, SuZhou (CN); Hao Zhou, SuZhou (CN); Tianrui Ni, SuZhou (CN)

(73) Assignee: OptoTrace (SuZhou) Technologies, Inc., Suzhou (CN)

( * ) Notice: Subject to any disclaimer, the term of this patent is extended or adjusted under 35 U.S.C. 154(b) by 41 days.

This patent is subject to a terminal disclaimer.

(21) Appl. No.: 14/051,396

(22) Filed: Oct. 10, 2013

(65) Prior Publication Data

US 2014/0043607 A1    Feb. 13, 2014

Related U.S. Application Data

(63) Continuation of application No. 13/080,142, filed on Apr. 5, 2011, now Pat. No. 8,582,099, which is a continuation-in-part of application No. 12/502,903, filed on Jul. 14, 2009, now Pat. No. 7,929,133, which (Continued)

(51) Int. Cl.
*G01J 3/44* (2006.01)
*G01N 21/65* (2006.01)
*B82Y 20/00* (2011.01)
*G01N 33/543* (2006.01)
*G01J 3/02* (2006.01)
*B82Y 40/00* (2011.01)

(52) U.S. Cl.
CPC ............... *G01N 21/65* (2013.01); *B82Y 20/00* (2013.01); *G01J 3/0264* (2013.01); *G01J 3/44* (2013.01); *G01N 21/658* (2013.01); *G01N 33/54346* (2013.01); *B82Y 40/00* (2013.01)

(58) Field of Classification Search
CPC ............... G01N 21/65; G01N 21/658; G01N 2021/656; G01J 3/02; G01J 3/44
USPC .............................................. 356/301, 72–73
See application file for complete search history.

(56) References Cited

U.S. PATENT DOCUMENTS

| | | |
|---|---|---|
| 4,933,274 A | 6/1990 | Sanford |
| 5,017,007 A | 5/1991 | Milne |
| 5,244,788 A | 9/1993 | Hubscher |

(Continued)

*Primary Examiner* — Abdullahi Nur
(74) *Attorney, Agent, or Firm* — SV Patent Service

(57) ABSTRACT

A method for detecting crude oil or gas in a drilling sample includes introducing a drilling sample into a sample solution containing nano particles, illuminating the sample solution comprising the drilling sample and the nano particles by a laser beam, collecting light scattered by the drilling sample and the nano particles in the sample solution, obtaining a Raman spectrum from the light scattered by the drilling sample and the nano particles in the sample solution, identifying, in the Raman spectrum, a spectral signature associated with a substance around a predetermined Raman shift, and detecting targeted chemicals correlated with crude oil or gas existence underground from where the drilling sample, based on the spectral signature of the substance in the Raman spectrum.

25 Claims, 52 Drawing Sheets

Related U.S. Application Data is a continuation-in-part of application No. 12/262,667, filed on Oct. 31, 2008, now Pat. No. 7,576,854, which is a continuation-in-part of application No. 11/562,409, filed on Nov. 21, 2006, now Pat. No. 7,460,224, said application No. 13/080,142 is a continuation-in-part of application No. 12/625,970, filed on Nov. 25, 2009, now Pat. No. 8,213,007, which is a continuation-in-part of application No. 12/403,522, filed on Mar. 13, 2009, now Pat. No. 8,102,525, said application No. 13/080,142 is a continuation-in-part of application No. 12/643,689, filed on Dec. 21, 2009, now Pat. No. 8,081,308.

(60) Provisional application No. 60/751,472, filed on Dec. 19, 2005.

(56) References Cited

U.S. PATENT DOCUMENTS

| | | |
|---|---|---|
| 5,527,712 A | 6/1996 | Sheehy |
| 5,864,397 A | 1/1999 | Vo-Dinh |
| 6,361,861 B2 | 3/2002 | Gao |
| 6,406,777 B1 | 6/2002 | Boss |
| 6,614,523 B1 | 9/2003 | Boss |
| 2002/0123050 A1 | 9/2002 | Poponin |
| 2003/0059820 A1 | 3/2003 | Vo-Dinh |
| 2003/0175472 A1 | 9/2003 | Den |
| 2004/0106203 A1 | 6/2004 | Stasiak |
| 2005/0136552 A1 | 6/2005 | Buechler |
| 2009/0214392 A1* | 8/2009 | Kameoka et al. ............ 422/102 |

* cited by examiner

SYSTEM AND METHOD FOR DETECTING OIL OR GAS UNDERGROUND USING LIGHT SCATTERING SPECTRAL ANALYSES

FIELD OF INVENTION

This invention relates to technologies for detecting crude oil and gas from drilling mud or rock samples extracted from underground.

BACKGROUND OF INVENTION

Raman scattering is an inelastic scattering of a photon which creates or annihilates an optical phonon. Raman scattering is the result of the interaction of incident photons with chemical molecular vibrations (i.e. phonons). A unique molecular structure results in a unique Raman scattering spectrum. Therefore, Raman scattering provides spectral fingerprint details about the molecules, and can also be used to distinguish molecular isomers and chiral molecules from each other.

Raman spectroscopy became commercially available after the invention of lasers in the late 1960's. A laser beam having a narrow line width is used to illuminate the testing chemicals in solid, liquid, or gas forms. The narrow line width of the laser beam can eliminate the overlaps of scattering peaks from photons with various wavelengths. The scattered light is collected by a photon detector such as Charge-Coupled Devices (CCD) or CMOS detector, which produces a Raman spectrum which is the intensity of the scattered light as a function of Raman shift defined as the wavenumber difference between the scattering light and incident laser. The spectral peaks in a Raman spectrum correspond to the vibration strengths of various molecular bonds, thus provide spectral fingerprints of the molecules.

Although Raman scattering is a useful analytical tool, Raman scattering has not been widely applied because of its weak scattering signals. Raman scattering has very weak signals due to the very small scattering cross section of molecules. Typically, only about $10^{-8}$ of the incident photons participates in Raman scattering. High power laser and high sensitivity CCD detector can be used to improve the scattering signals; however, it only makes limited improvement in detecting Raman scattered signal, and it requires extra costs and additional hardware, and can cause unexpected damages to samples.

Raman scattering signal can be enhanced by placing testing molecules in the vicinity of roughened surfaces. In Nano-Enhanced Raman Spectroscopy (NERS), or surface-enhanced Raman spectroscopy (SERS), a sample surface can be formed by deposition of metallic particles or clusters. The nano-enhanced Raman scattering phenomena can be explained by interaction between photons with localized electromagnetic field enhancement and chemical enhancement. The enhancement by SERS has been observed in different research labs. An Intel team used a porous silicon structure with coatings of noble metals such as silver on the surface, and demonstrated that Raman scattering signal increased as the porous silicon pore-size was decreased.

Accordingly, there is a need for low cost, convenient SERS devices for a wide-range of commercial applications.

SUMMARY OF THE INVENTION

The present application discloses a convenient method for detecting oil and gas under the ground. The disclosed method is accurate and can be implemented in the field near the drilling hole where the drilling fluids and rock samples are collected. The disclosed methods can significantly shorten testing cycle times (from a day or days to minutes) and decreases measurement costs, compared to conventional testing methods.

Since nano-surface enhanced Raman spectral analysis is highly sensitive, the presently disclosed method is capable of detecting substances that are partially evaporated in the drilling samples (for example, mud, rock, etc.), during the drilling, or after the drilling sample is obtained but before the measurement. Thus, the presently disclosed method is especially advantageous for hydrocarbon molecules that have low boiling or vaporization temperatures, which are often rich in the content of oil or gas.

Another advantage of the presently disclosed methods is that the central office can instantaneously monitor testing results from multiple locations in the field, which allows the monitoring network system to have a global picture for potential oil and gas deposits in a large geological area.

Yet another advantage of the presently disclosed methods is that by providing testing in the field, feedback and guidance can be provided almost real time to the drilling strategies in the field. For example, if a drilling hole or rock core show promising oil/gas content at different depths underground, more drilling can be done at different depths or in the adjacent areas to explore detailed scope of the oil and gas deposits underground. If the in-field testing result is not promising at a location, the drilling team can quickly move on to the next location. Thus the entire drilling exploration is made more efficient by the presently disclosed methods.

In one aspect, the present invention relates to a method for detecting crude oil or gas in a drilling sample. The method includes introducing a drilling sample into a sample solution containing nano particles; illuminating the sample solution comprising the drilling sample and the nano particles by a laser beam; collecting light scattered by the drilling sample and the nano particles in the sample solution; obtaining a Raman spectrum from the light scattered by the drilling sample and the nano particles in the sample solution; identifying, in the Raman spectrum, a spectral signature associated with a substance around a predetermined Raman shift; and determining oil or gas content in the drilling sample based on the spectral signature of the substance in the Raman spectrum.

Implementations of the system may include one or more of the following. The drilling sample can be extracted from a first drilling hole in the ground, and wherein the steps of illuminating the sample solution and collecting light scattered by the drilling sample are conducted in the vicinity of the first drilling hole. The drilling sample can be collected in a first drilling hole underground, and the steps of illuminating the sample solution and collecting light can be conducted by a detector in the drilling hole underground. The method can further include adjusting drilling depths or locations of one or more drilling holes in real time in response to the crude oil or gas content determined in the drilling. The substance can include aromatic molecules. The substance can include at least one of a multi-ring aromatic molecule, thiophene, dibenzothiophene, methyl dibenzothiophene, phenanthrene, methylphenanthrene, carbazole, or a homologue of aforementioned molecules, n-hexane, cyclohexane, benzene, toluene, or xylene, otctane, heptane, or nonane. The substance can include nitrogen containing hydrocarbon compounds. The nitrogen containing hydrocarbon compounds can include carbazole or homologue compound molecules of carbazole. The substance can include sulfur containing hydrocarbon compounds. The sulfur containing hydrocarbon compounds can include dibenzothiophene or homologue compound molecules of dibenzothiophene. The spectral signature can include at least one spectral peak around the predetermined Raman shift. The method can further include determining a concentration of the substance in the drilling sample using the spectral signature. The method can further include after the step of introducing, allowing molecules in the drilling sample to adsorb to the nano particles in the sample solution. The sample solution can include multi-valence ions. The method can further include introducing an ionic material into the sample solution, wherein the sample solution has an ionic concentration in a range from about 10 µM to a saturation level. The nano particles can include a magnetic or ferromagnetic material. The method can further include applying an electrical field, a magnetic field, or an electro-magnetic field to the sample solution during the step of collecting. The nano particles can include a material selected from a group consisting of a metal, a metal alloy, an oxide material, silicon, a polymeric material, and a combination thereof. The nano particles have an average dimension in a range from about 1 nm to about 10 µm. The nano particles can have an average dimension in a range from about 5 nm to about 500 nm. The nano particles can have a size distribution characterized by an average dimension and a width, wherein the ratio of the width to the average dimension is in a range from about 0.01 to about 3. The nano particles can include carbon nano tubes.

In another aspect, the present invention relates to a method for predicting presence of crude oil or gas in the underground. The method includes defining an array of sample dots on a surface of a sliced rock sample obtained from underground; illuminating each of the sample dots on the surface of the sliced rock sample by a laser beam; collecting light scattered by the surface of the sliced rock sample at each of the sample dots; obtaining a Raman spectrum from the surface of the sliced rock sample at each of sample dots; determining a mineral content at each of the sample dots on the surface of the sliced rock sample based on the Raman spectrum; obtaining a map of mineral content on the surface of the sliced rock sample; and predicting a probability of crude oil or gas underground using the map of mineral content.

Implementations of the system may include one or more of the following. The method can further include establishing Raman spectral signatures in a plurality of minerals, wherein the step of determining a mineral content includes identifying a Raman spectral signature associated with one of the plurality of minerals in the Raman spectrum. The method can further include for at least one of the plurality of minerals, establishing a quantitative dependence of spectral intensity at one of the Raman spectral signatures as a function of the concentration of the one of the plurality of minerals, wherein the step of determining a mineral content includes calculating a concentration of the one of the plurality of minerals based on the function and spectral intensities at the spectral signature. The sliced rock sample can be extracted from a first drilling hole in the ground, and wherein the steps of illuminating and collecting light are conducted in the vicinity of the first drilling hole. The method can further include in response to the map of mineral content on the surface of the sliced rock sample, adjusting drilling depths or locations of one or more drilling holes in real time. The mineral content includes one or more of Quartz, Calcite, Plagioclase, Dolomite, Pyroxene, Chlorite, Kalifeldspar, Na-feldspar, Amphibole, MuscLaumontite and analcime ovite, Biotite, Ankerite, Siderite, Anhydrite, Gypsum, Thenardite, Barite, Pyrite, Glauberite, Laumontite, Analcime, Illite, Smectite, Kaolinite, Corundum, Ankerite, Halite, Mica, Hornblende, or Granite.

In another aspect, the present invention relates to a method for predicting presence of crude oil or gas in the underground. The method includes receiving a drilling sample to detect hydrocarbon gases extracting from a drilling sample, which include, but not limited to, $CH_4$, $C_2H_6$, $iC_4H_{10}$, $nC_4H_{10}$, $iC_5H_{12}$, $nC_5H_{12}$, $C_mH_n$ (m is an integer, 1, 2, 3, etc., n=2×m+2). It is also valuable to be able to detect non-hydrocarbon gases, including $O_2$, $N_2$, CO, $CO_2$, $H_2$, $H_2S$, $SO_2$, $NH_3$, etc. using a Raman sensor.

In another aspect, the present invention relates to a method for predicting presence of oil or gas in the underground. The method includes receiving a drilling sample and a sliced rock sample obtained from a same geological location; introducing the drilling sample into a sample solution containing nano particles; illuminating the sample solution comprising the drilling sample and the nano particles by a first laser beam; collecting light scattered by the drilling sample and the nano particles in the sample solution; obtaining a first Raman spectrum from the light scattered by the drilling sample and the nano particles in the sample solution; identifying, in the first Raman spectrum, a spectral signature associated with a substance around a predetermined Raman shift; determining oil or gas content in the drilling sample based on the spectral signature of the substance in the first Raman spectrum; illuminating a surface of the sliced rock sample by a second laser beam; collecting light scattered by the surface of the sliced rock sample at each of the sample dots; obtaining a second Raman spectrum using the light scattered from the surface of the sliced rock sample at each of sample dots; determining a mineral content at each of the sample dots on the surface of the sliced rock sample based on the second Raman spectrum; and predicting a probability of crude oil or gas underground using the mineral content and crude oil or gas content in the drilling sample.

These and other aspects, their implementations and other features are described in detail in the drawings, the description and the claims.

DETAILED DESCRIPTION OF THE INVENTION

Figure 1:
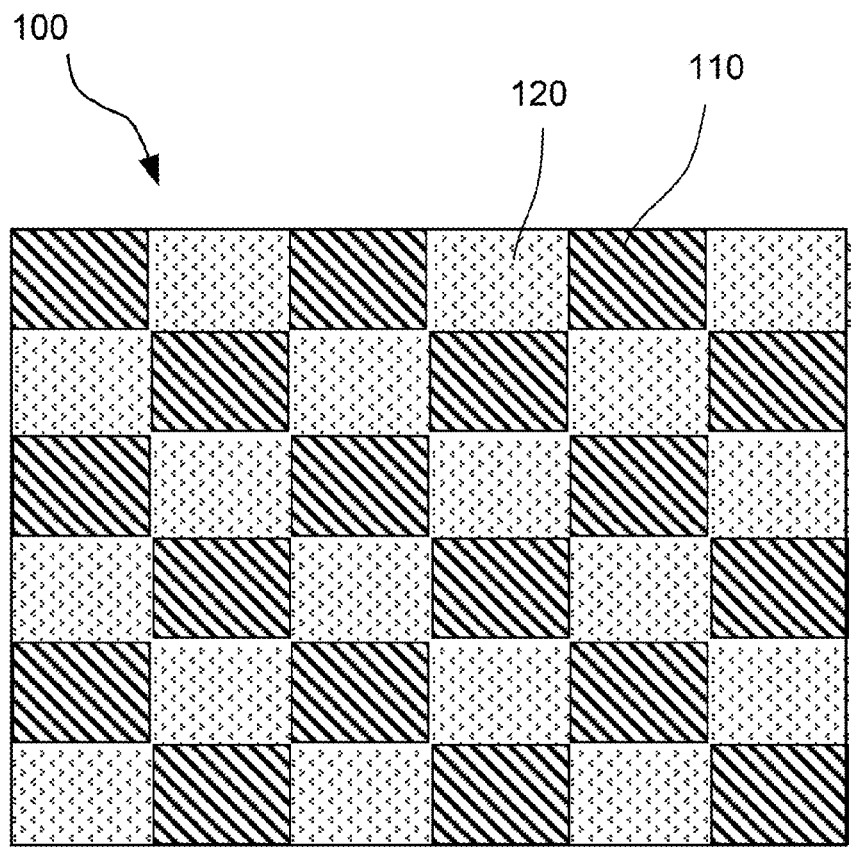
FIG. 1 is a top view of a square array of an array device according to the present invention.

The present invention provides new devices and apparatus/systems as well as methods for improved performance of Nano-Enhanced Raman Spectroscopy (NERS), or called Surface-Enhanced Raman Spectroscopy (SERS).

SERS selectivity of surface signal results from the presence of surface enhancement mechanisms demonstrated only at the surface of nano particles. There are two primary mechanisms of surface enhancement: electromagnetic enhancement and chemical enhancement. The electromagnetic enhancement is dependent on rough features, nano particle size, shape and distribution present on a surface with nano particles, while the chemical enhancement involves electronic charge transfer and changes to the adsorbate electronic states due to chemisorption of the analytes.

SERS is observed primarily from analytes adsorbed onto coinage (Au, Ag, and Cu) or alkali (Li, Na, K) metal surfaces, with the excitation wavelength near or in the visible region. Theoretically, any metal would be capable of exhibiting the effect of surface enhancement, but the coinage and alkali metals satisfy calculable requirements and provide the strong enhancement.

The great part of the overall enhancement of SERS is due to an electromagnetic enhancement mechanism that is a direct consequence of the presence of metal roughness features, nano particle size, shape and distribution present on a surface with nano particles, or nano particle size, shape and distribution present in a test reagent containing nano particles.

The chemical enhancement mechanism also provides enhancement for the gain of Raman signal intensity. The molecule is adsorbed onto the surface and interacts with the surface. The chemical enhancement exists because of this interaction. The metal adsorbate proximity allows pathways of electronic coupling from which novel charge-transfer intermediates emerge, leading to a SERS condition with higher Raman scattering cross-sections. In addition, the electronic orbits of the adsorbate molecules may contact and interact with the conducting electrons of the metal, altering the chemical state of the chemical substance. It is also proposed that the chemical enhancement may be an alteration in the scattering cross-section, which is the chemical nature of the chemical substance changing due to its interaction with the metal.

The present invention provides an array device comprising a substrate, or the nano particles in a test reagent, supporting a plurality of nano structures and an exposed sensing surface upon the nano structures, wherein said surface includes at least one active SERS nano surface and at least one inactive SERS nano surface established in proximity to the active SERS nano surface. Accordingly, the performance of this SERS device benefits from both electromagnetic effect and chemical enhancement to the Raman signal intensity.

The term, "active SERS nano surface", when used herein, encompasses a well-defined metal surface having at least one surface dimension on a nanometer scale. The surface may or may not be flat. The active SERS nano surface exhibits electromagnetic enhancement to Raman signal under photon irradiation. Examples of materials for the active SERS surface include noble metal such as Ag, Au, Cu, and Pt, and transition metals such as Al, Fe, Co, Ni, Ru, Rh, and Pd. The material used for the active SERS surface is referred as "active material".

The term, "inactive SERS nano surface", refers to a surface having at least one dimension on a nanometer scale. The surface may or may not be flat. In contrary to the active SERS nano surface, the inactive SERS nano surface does not exhibit significant electromagnetic enhancement to Raman signal just by itself. However, when the inactive SERS surface was placed in proximity to the active SERS nano surface, a relatively stronger enhancement of Raman signal was observed, compared with the signal from merely the active SERS nano surface. Therefore, the inactive SERS nano surface arranged in an alternative fashion with the active SERS surface provides further enhancement to Raman signal. Examples of materials for the inactive SERS nano surface include insulators such as $SiO_2$, $Al_2O_3$, $Si_3N_4$, $Ta_2O_5$, $TiO_2$, and air (open space). The material used for the inactive SERS nano surface is referred as "inactive material".

The term, "nano structure", as used herein, is intended to mean a 3-dimensional object either extruded away from the substrate or recessed toward the substrate, or small size particles having at least one dimension on a nanometer scale, or the nano particles in a test reagent. Non-limiting examples of the shape of the nano structure include nano rod, nano pyramid, nano hole, nano pit, and nano particles at the surface of a substrate, or nano particles in a solution, or a test reagent, containing noble metal (such as silver Ag, gold Au, etc.) nano particles with averaged particle size in the range of about 2 and about 100 nm, Then, light scattered by the mixed sample solution, with or without the nano-scale surface structure, and the adsorbed molecules is collected.

According to one embodiment of the present invention, an improved SERS performance is achieved by arranging the inactive SERS nano surface next to the nano active SERS surface. FIGS. 1-11 provide exemplary array devices for improved SERS applications.

FIG. 1 is a top view of a square array 100 with a plurality of active SERS nano surfaces 110 and inactive SERS nano surfaces 120 established on a substrate, or the nano particles in a test reagent. As shown in FIG. 1, each active SERS nano surface is alternatively arranged with each inactive nano SERS surface. The active SERS surfaces are made from a material selected from a group of noble metals, including but not limited to Ag, Au, Cu and Pt. The active SERS surfaces may also be made from a material selected from a group of transition metals, including but not limited to Al, Fe, Co, Ni, Ru, Rh, and Pd. The inactive SERS nano surfaces are made from insulating materials, including but not limited to $SiO_2$, $Al_2O_3$, $Si_3N_4$, $Ta_2O_5$, $TiO_2$, and open space (air).

Figure 2A:
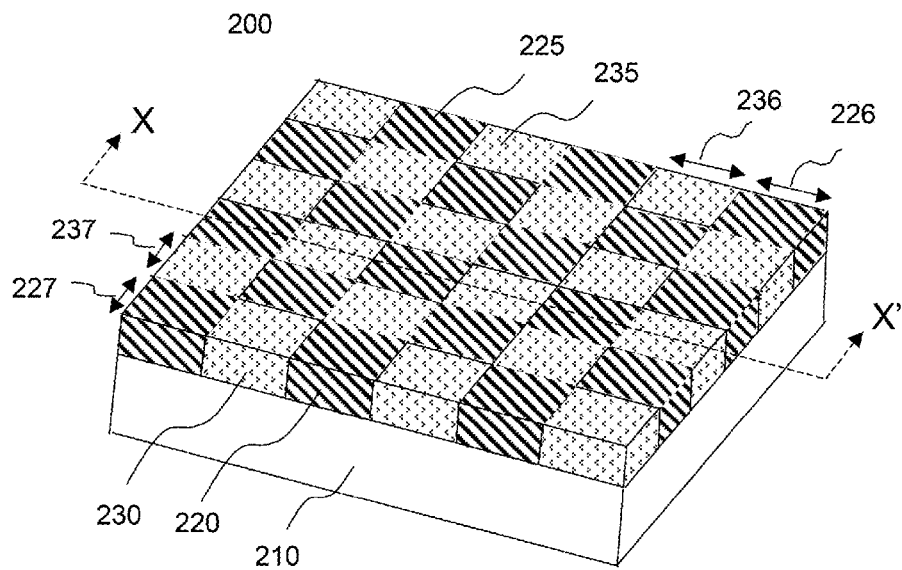
FIGS. 2A and 2B show a square array according to the present invention.

FIG. 2A shows a perspective view of an array device 200 according to one aspect of the present invention. The device comprises a substrate 210, an array of rectangular rods 220 made of an active material and an array of rectangular rods 230 made of an inactive material. Each active rod 220 is alternatively arranged with each inactive rod 230. The active rod 220 provides the active SERS nano surface 225 and the inactive rod 230 provides the inactive nano SERS 235. Both surfaces 225 and 235 are substantially square, having dimensions of 226, 227, 236, and 237 between about 5 nm to 300 nm. In one embodiment, the dimension of the squares is between about 1 nm and about 10 μm.

Figure 2B:
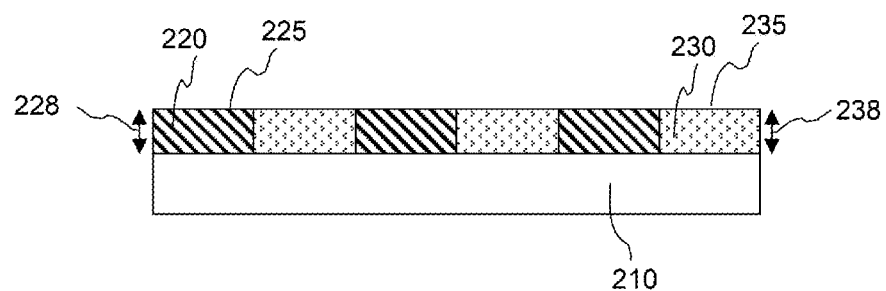

FIG. 2B is a sectional view of the structure of FIG. 2A, sliced at line X-X' of the structure shown in FIG. 1. The height 228 of the active surface 225 is substantially equal to the height 238 of the inactive surface 235. The height 228 and 238 is between 5 nm to 1000 nm. In one embodiment, the height 228 and 238 is between 1 nm to 5 μm.

Figure 3A:
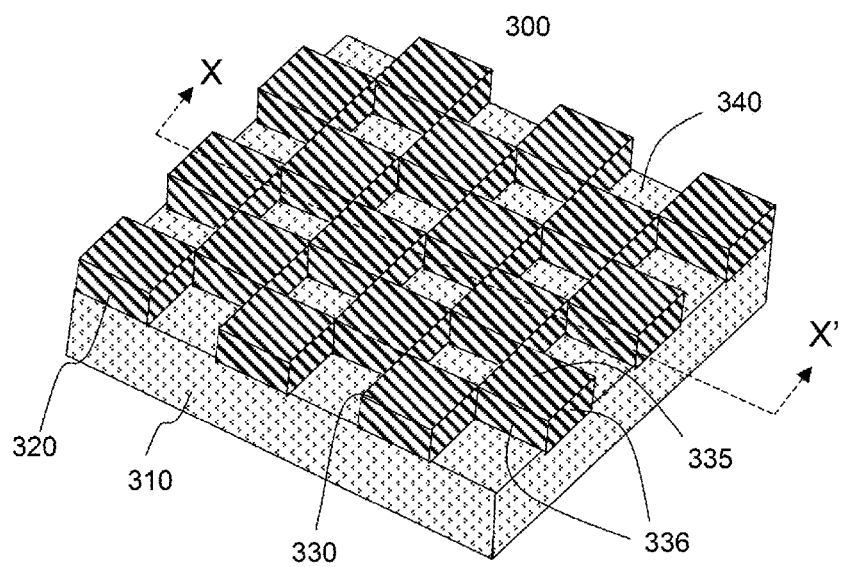
FIGS. 3A and 3B show a square array according to the present invention.
Figure 3B:
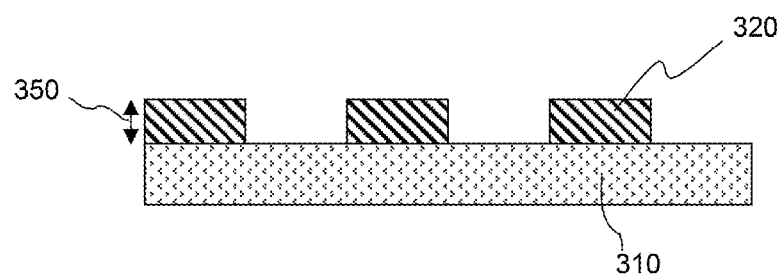

FIG. 3A shows a perspective view of another square array 300. The substrate 310 is made from an inactive material. A plurality of square rods 320 are formed on the substrate. The rod 320 provides the active SERS nano surface 330, which includes top surface 335 and side wall 336. The active SERS nano surface 330 is surrounded by four square areas 340 of inactive SERS nano surfaces. The square area 335 of the active SERS surface is substantially equal to the inactive area 340. A sectional view of a cutoff at line X-X' is shown in FIG. 3B. The height 350 of the rod 320 is between 5 nm to 1000 nm. In one embodiment, the height 350 of the rod 320 is between 1 nm to 5 μm.

The detection sensitivity of the Raman scattering sensors can be enhanced when at least a portion of the nano structures or nano surfaces (active or inactive) has a nano feature size functionally matched with a characteristic parameter of electrons or phonons such as an electron mean-free path (MFP) of electrons on the surface, electron wavelength of electrons on the surface, a phonon MFP of phonons on the surface and a phonon wavelength of phonons on the surface.

The term "nano feature size" is used herein to refer to the dimensions of an active nano SERS surface such as the diameter of an active nano SERS surface, the height or depth of a nano rod or a nano hole, or the spacing between nano structures in the array device.

The term, "functionally match" as described above may include the condition that the nano feature size is approximately equal to, smaller than, integer numbers of, or with a special mathematical function to the characteristic parameter of electrons or phonons.

Figure 4:
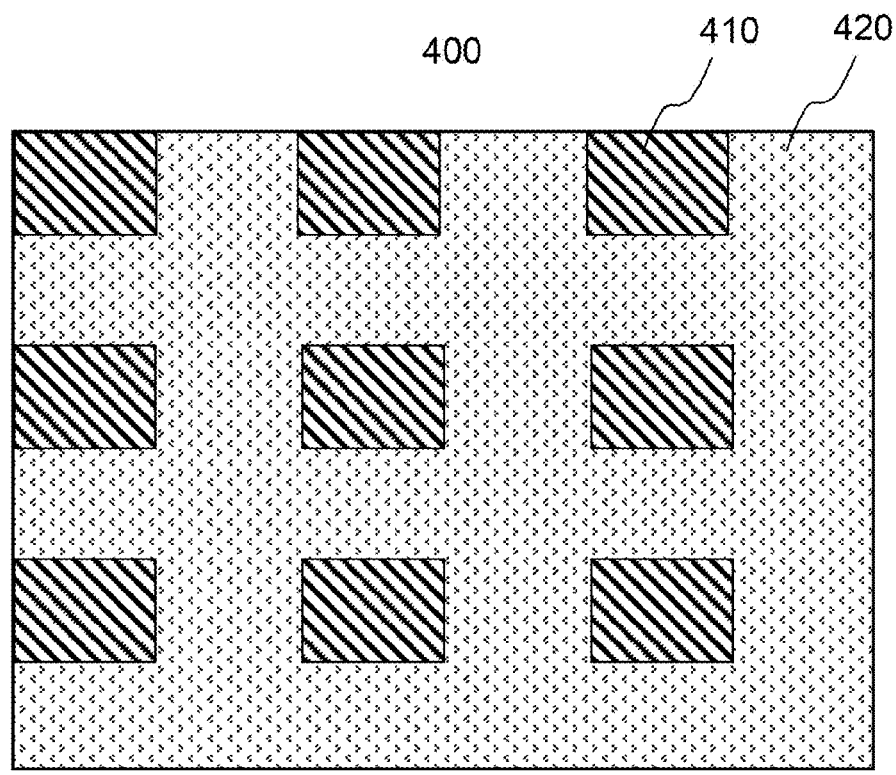
FIG. 4 is a top view of another square array according to the present invention.

FIG. 4 shows another example of a square array 400 of nano surface structure where the active SERS surfaces 410 are physically isolated from each other by inactive SERS nano surface 420. Again, the spacing between the active areas can be air or insulating materials as illustrated in FIGS. 2 and 3.

Figure 5A:
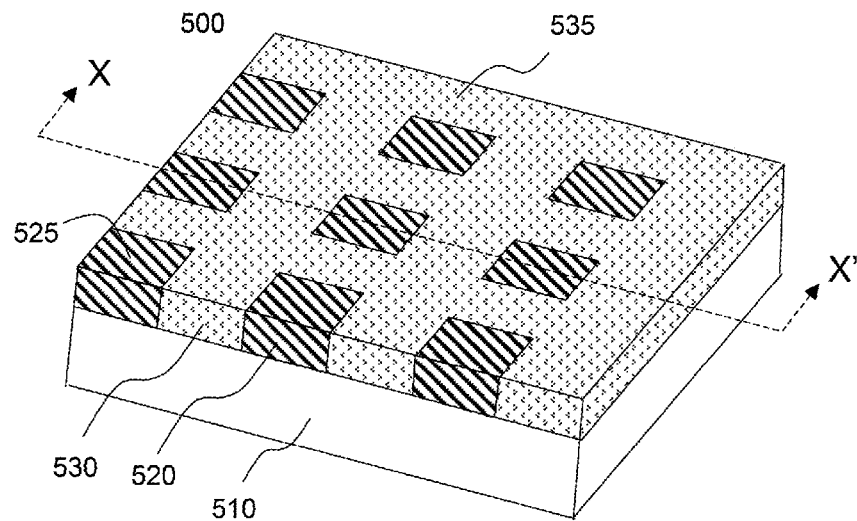
FIGS. 5A and 5B show a square array with isolated active areas and surrounding inactive areas.
Figure 5B:
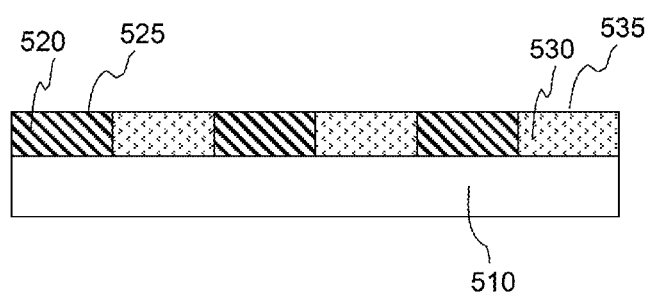

Referring now to FIGS. 5A and 5B, an array device 500 having square rods 520 of an active material is established on a substrate 510. Each rod 520 is surrounded by a region 530 made of an inactive material. A cutoff view from line X-X' is shown in FIG. 5B. Each active SERS nano surface 525 is isolated by an inactive nano surface 535.

Figure 6A:
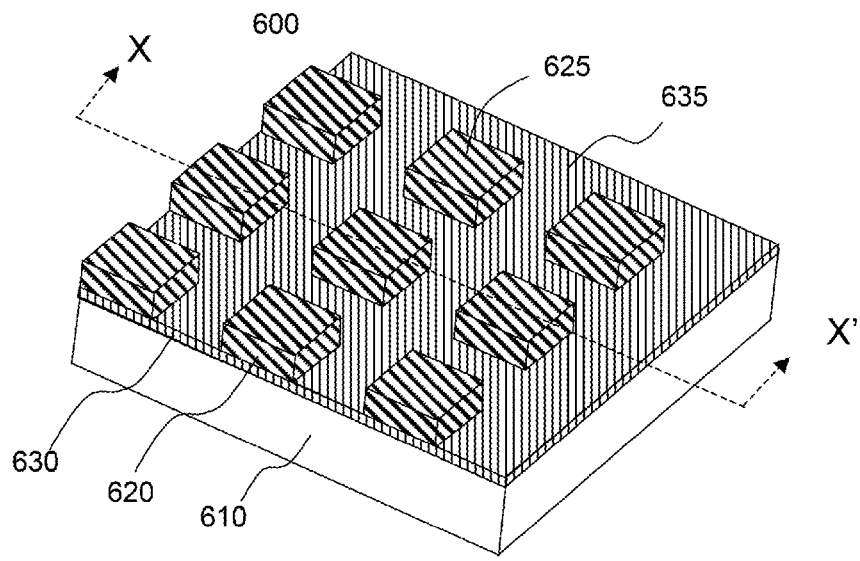
FIGS. 6A and 6B show a square array with a layer of active material connecting each of the active nano surface structure.
Figure 6B:
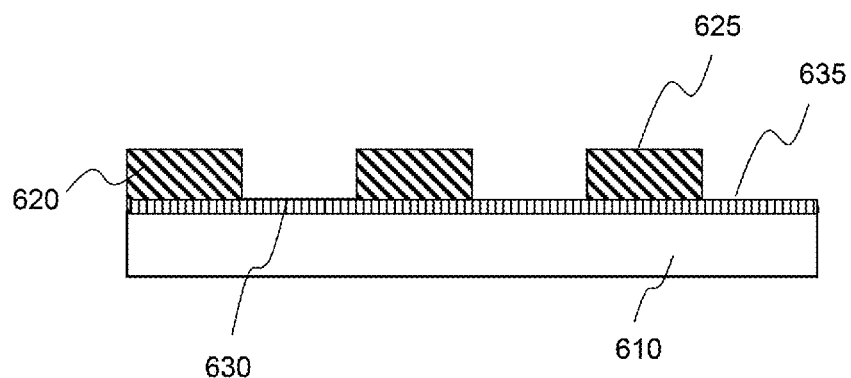

In some embodiments, FIG. 6A is a perspective view showing an array device 600 having a substrate 610 covered by a layer 630 of an active material. Square rods 620 of another active material established on the layer 630. A cutoff view from line X-X' is shown in FIG. 6B. Each active SERS nano surface 625 is isolated by another active nano surface 635. In a special case, a same active material is used for both square rods 620 and layer 630 and the active structures are connected at the bottom of the active areas. The connecting materials can be same as in the active area or different conductors.

Figure 7:
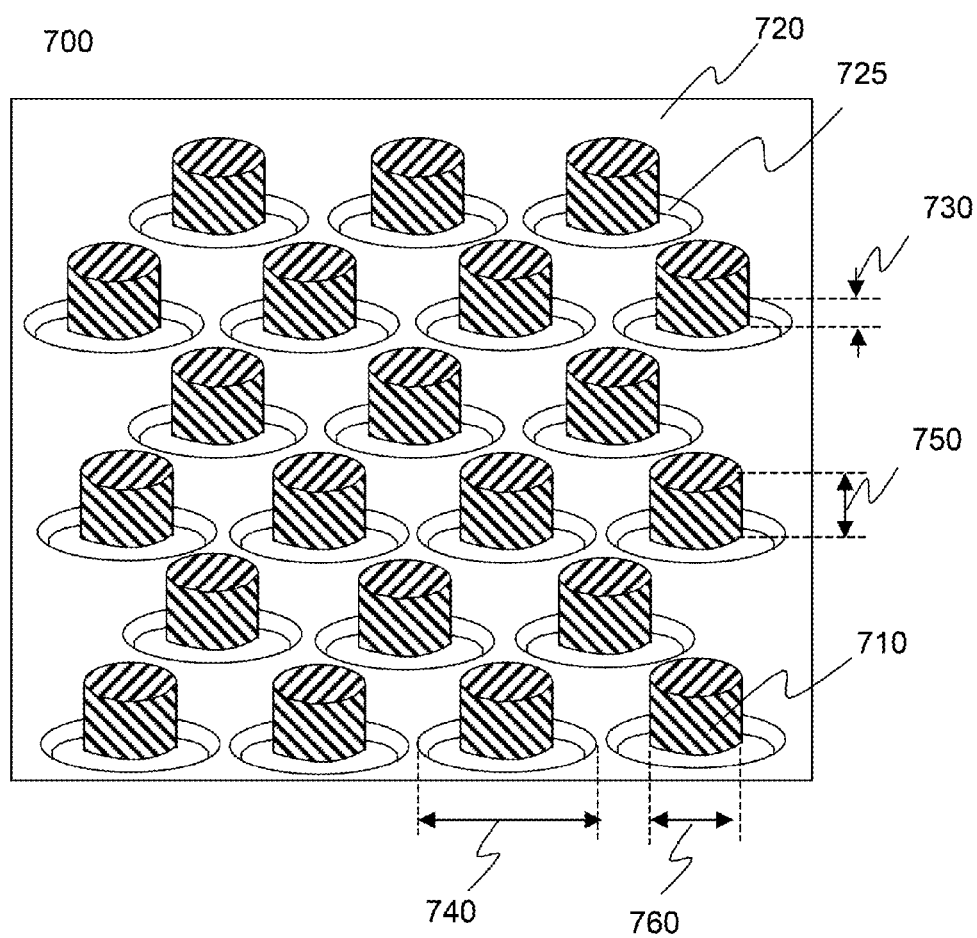
FIG. 7 is a three dimensional view of cylindrical form of array of independent active nano surface structures on surrounding inactive area, with an inactive area depression at the bottom of each of the active nano surface structures.

It is to be understood that the shapes of the nano structures can be altered as desired for specific applications. FIGS. 7-9E show examples of nano rods or nano holes. FIG. 7 shows a perspective view of cylindrical form of array of nano surface structures 700. The independent active areas in their cylindrical forms 710 are regularly distributed on surrounding inactive area 720 to form an array of the nano surface structures 700. The bottom of each of the active cylinder is situated on a depression 725 in the inactive area 720. The depth 730 of the depression in the inactive area is smaller than the height 750 of the cylindrical active rod 710. The diameter 740 of the depression 725 is larger than the diameter 760 of the active rod by a distance on a nanometer scale. Various geometrical features can be designated to maximize the adsorption of molecules. The depression shown on this figure is one of the examples of the enhancement providing structure.

Figure 8A:
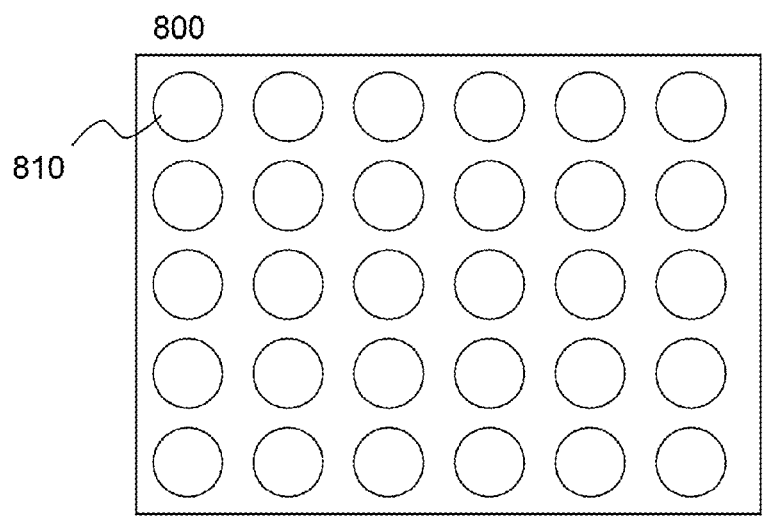
FIGS. 8A and 8B are top views of circular arrays.
Figure 8B:
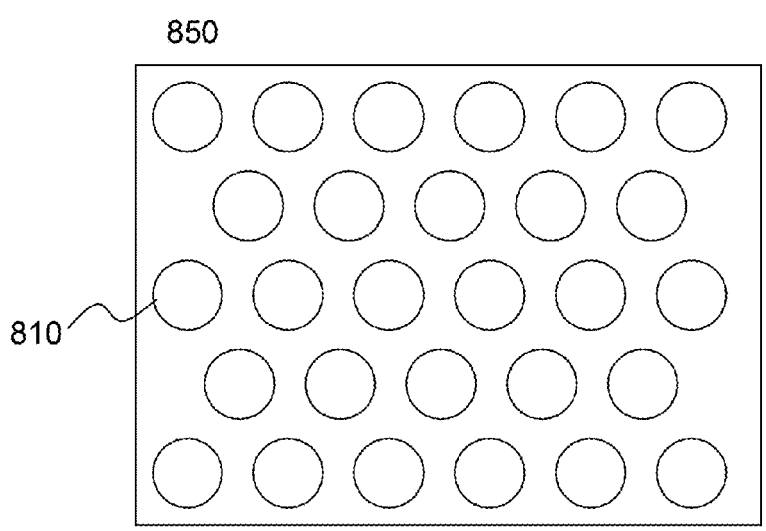

FIG. 8A shows a top view of circular array 800 of nano surface structures which are regularly distributed on a substrate. The area in circles 810 can be the active SERS nano surface or the inactive SERS nano surface (or even air, meaning empty). FIG. 8B shows a top view of another circular array 850 of nano surface structure with a tight packaging of the circles on a substrate.

Figure 9A:
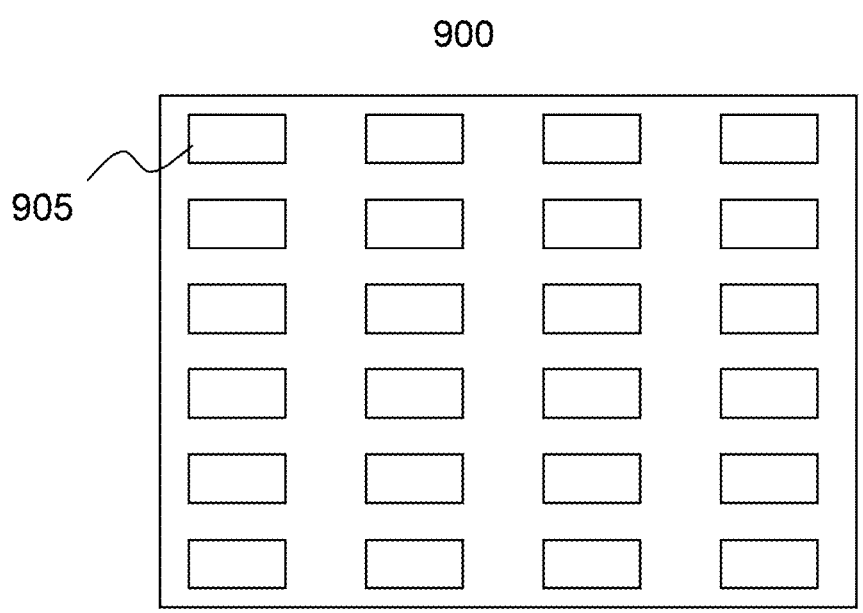
FIGS. 9A-9E show top views of arrays of various shapes.
Figure 9B:
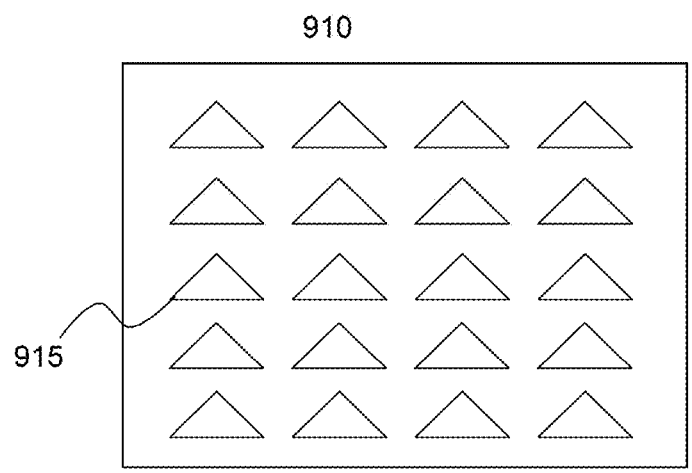
Figure 9C:
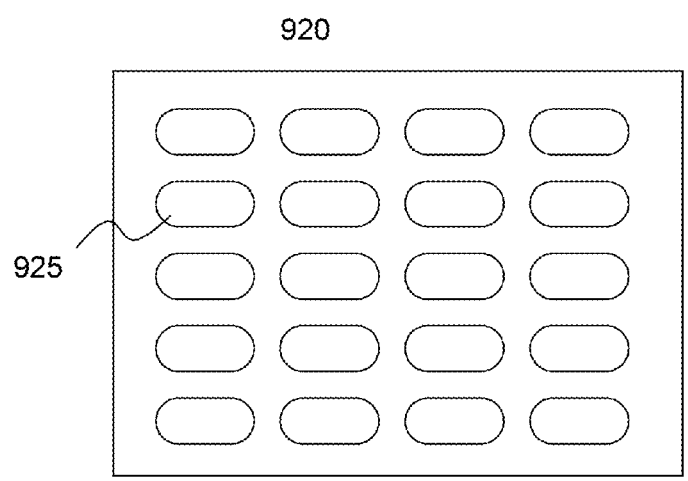
Figure 9D:
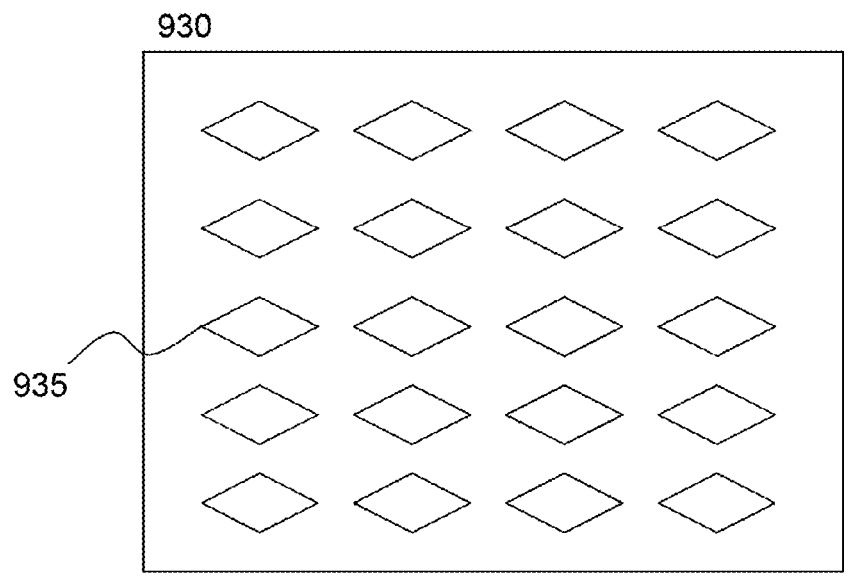
Figure 9E:
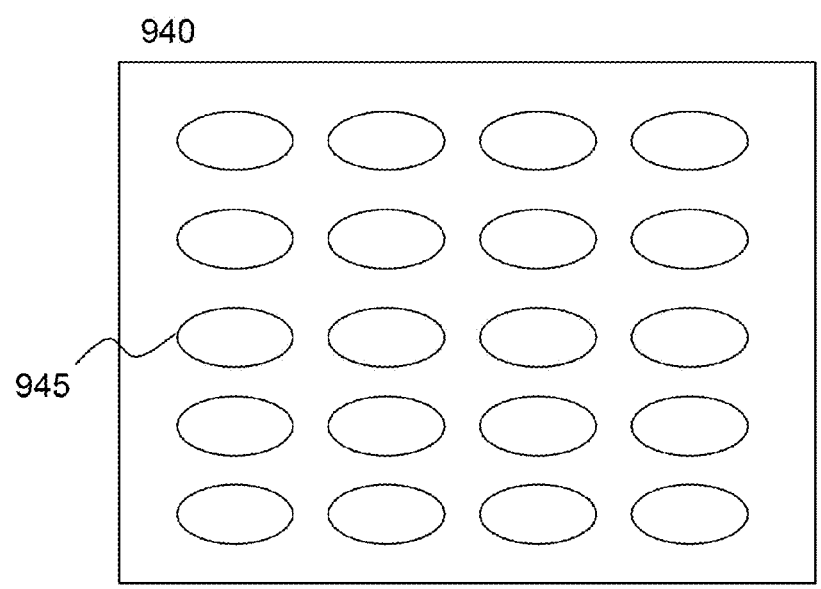

FIG. 9A shows a top view of an array 900 of rectangular nano surface structures 905. FIGS. 9B-9E show a top view of arrays 910, 920, 930, and 940 of triangular 915, round rectangular 925, diamond 935, and oval 945 shapes of nano rods or nano holes.

Figure 10:
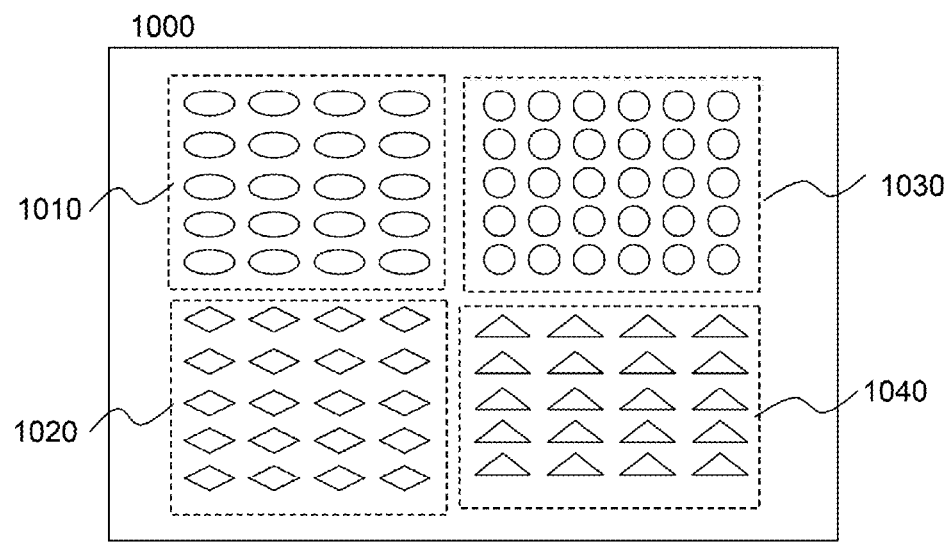
FIG. 10 shows an array comprising sub-arrays with various shapes.
Figure 11:
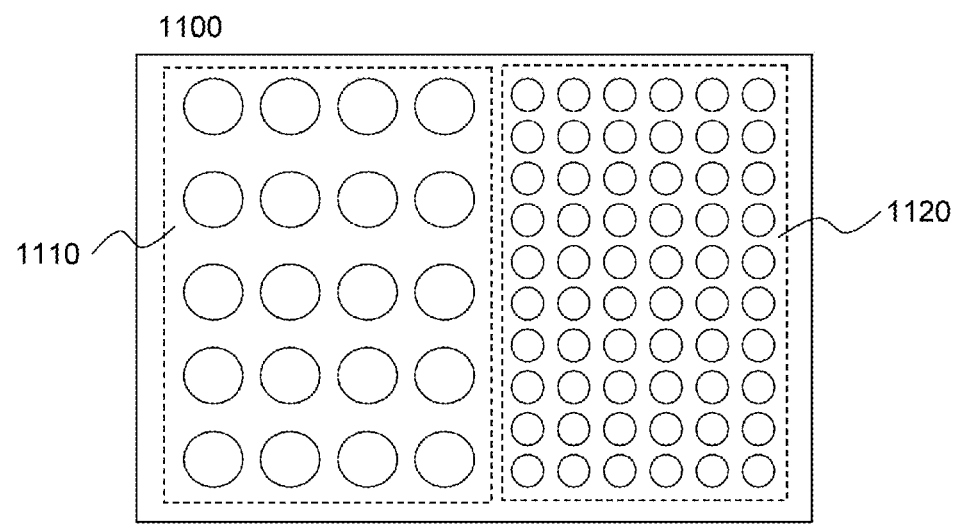
FIG. 11 shows an array comprising sub-arrays with various sizes.

FIGS. 10 and 11 illustrate that an array device can include a number of sub arrays on a substrate. An advantage of the combination of the sub-arrays is that the nano surface structures are optimized for chemical measurement by SERS for a wide range of substances. The combination of different arrays can be used as a general Raman enhancement tool.

FIG. 10 shows a top view of an array device 1000 having sub-arrays 1010, 1020, 1030, and 1040. Each of the sub-arrays has different shapes of the nano structures. FIG. 11 illustrate an array device 1100 having sub-arrays 1110 and 1120. The sub-arrays may have the same shape but have different size.

Figure 12:
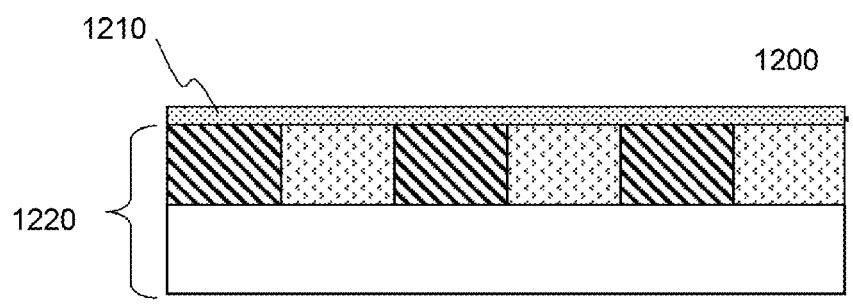
FIG. 12 is a cross sectional view of an array with a surface adsorption layer over the entire array.

With reference now to FIG. 12, an array device 1200 which has an adsorption layer 1210 over a structure 1220 which is similar to array 200 or 500 shown in FIG. 2 and FIG. 5 respectively. Based on the specific chemical bonding configurations of a measured chemical in SERS, the surface adsorption layer 1210 can be selected with adequate chemical bonds, either positive charged or negative charged, so that the measured chemicals can be adsorbed to the surface, and moved to close to and then adsorbed onto the active areas. The adsorption layer does not need to be very thick. In some cases, a monolayer or even island distributed layer will be sufficient. The layer thickness can be between 0.5 nm and 500 nm, preferred between 2 nm-20 nm. Materials suitable for the adsorption layer include Ag oxide, Au mixed with oxide, $TiO_2$, $SiO_2$, $Al_2O_3$, $Si_3N_4$, $Ta_2O_5$, ZnO, Zr oxide, Hf oxide, Y oxide, Ag oxide, Au oxide, Sn oxide, Sb oxide, or other metal oxide layer, metal layer doped with chlorine or chloride, polymers, etc.

Figure 13:
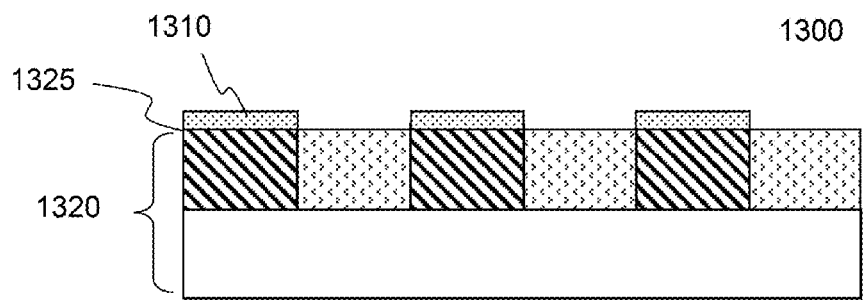
FIG. 13 is a cross sectional view of an array with a surface adsorption layer selectively covering active SERS nano surfaces.
Figure 14:
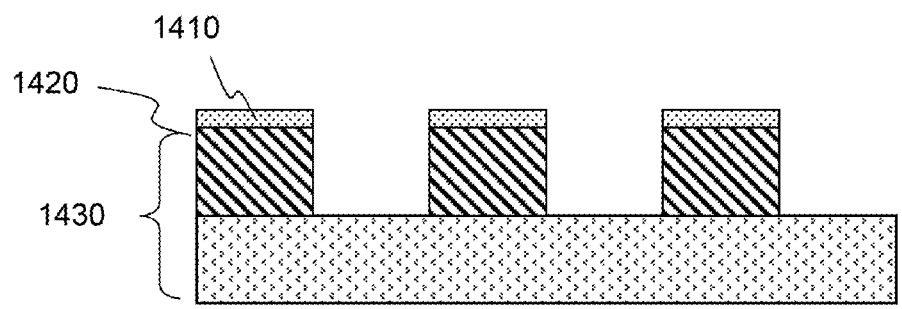
FIG. 14 is a cross sectional view of an array with a surface adsorption layer selectively covering active SERS nano surfaces according to the present invention.
Figure 15:
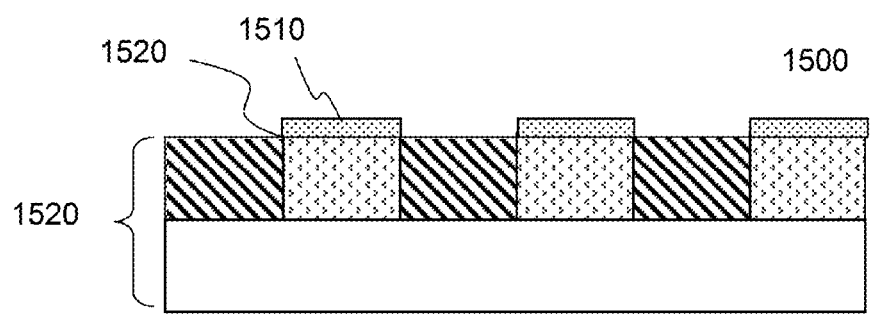
FIG. 15 is a cross sectional view of an array with a surface adsorption layer selectively covering inactive SERS nano surfaces.

FIGS. 13-15 illustrate various arrangements of the adsorption layer over an array device. In one embodiment, the adhesion layer covers only the active SERS nano surfaces. FIG. 13 shows an array device 1300 having the adsorption layer 1310 disposed selectively on the inactive SERS nano surfaces 1325. The structure 1320 is similar to the array device 200 or 500 shown in FIGS. 2 and 5 respectively. Alternatively, an adsorption layer 1410 may be selectively disposed on the active SERS nano surface 1420 for array 1400 shown in FIG. 14.

In another embodiment, an adsorption layer 1510 may be selectively disposed on top portion of the isolated inactive SERS nano surface 1520 as shown in FIG. 15. The structure 1530 is similar to the array structure 300 shown in FIG. 3.

The presently disclosed device is compatible with other arrangements of the adsorption layer, which can help bring molecules of an analysis close enough to the active nano SERS surface.

Figure 16:
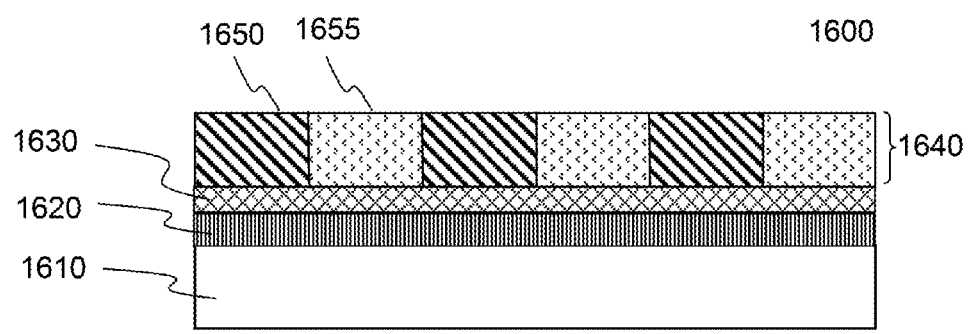
FIG. 16 is a cross sectional view of an array device with a function layer between a substrate and an array of nano structures.

In some embodiments, an enhancement of molecule adsorption to the device surface is provided by electrical biasing. FIG. 16 shows a device 1600 of an array of nano surface structure 1640 with active and inactive SERS nano surfaces 1650 and 1655 over a metallic layer 1620 on a substrate 1610. There is an optional insulator layer 1630 separating the array 1640 from the metallic layer 1620. Based on the charge states of the measured chemical molecules, a positive or negative bias can be applied to the metallic layer 1620 to attract the molecules to the sensing surface 1650 and 1655.

The metallic layer 1620 is also referred as a function layer. The term, "function layer", as used herein, refers to a layer providing electrical, magnetic, or thermal bias to the array device of nano surface structure.

Figure 17:
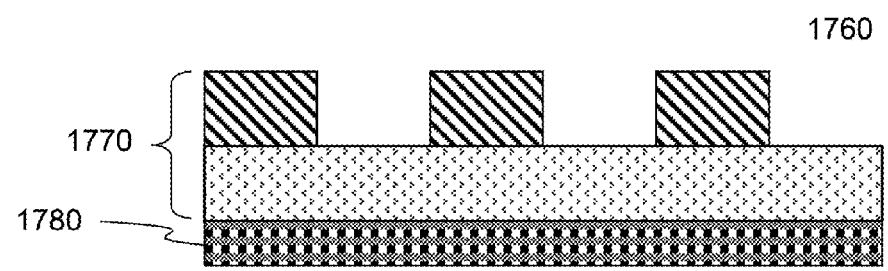
FIG. 17 shows another array device with a function layer.

In some embodiments, molecular adsorption to the device surface can be enhanced by lowering the temperate of the whole array. Given that the array is much thinner than the substrate, a thermal electrical cooler can be connected to the bottom of the substrate, or to the metal pad area of a sensing chip. Referring to FIG. 17, an array device 1760 includes a thermally conductive substrate 1780. By applying an electrical field to a cooler, the substrate 1780 including the nano array 1770 can be cooled down to, for example, a temperate range from −20° C. to 20° C. A lower temperature can be achieved by using a more expensive thermal electrical or other cooler. The lower the surface temperature, the more molecules will be condensed on the surface. By targeting cooled temperature to a sensing chip, selected chemical molecules depending on their boiling temperature would be adsorbed onto the surface.

In some embodiments, the function layer can be used for the purpose of applying a proper DC or AC biasing voltage to the device to attract chemical molecules since many of interested molecules carry positive or negative electric charges. Furthermore, the function layer provides a means to heat the sensing surface to vaporize unexpected/unwanted surface contamination and/or burn out surface contamination. The materials of the conductive layer can include, but not limited to, Ti, Ni, Cr, Pt, Ru, Ni—Cr alloy, NiCrN, Pt—Rh alloy, Cu—Au—Co alloy, Ir—Rh alloy or/and W—Re alloy. The conductive layer can have both good electrical and thermal conductivity, good adhesion to both silicon substrate and metallic sensing surface layer.

In some embodiments, the magnetic field is supplied by the function layer to the sensing chip, or by an external source. In this way, the chemical polar molecules on the sensing surface would have statistically preferred orientation; on the other hand, the chemical polar molecules under test could have their statistically preferred orientation. The effect of applied magnetic field or built-in magnetic materials at function layer is to enhance chemical specific binding, i.e., enhancing chemical molecule adsorption onto the sensing surface, so that to enhance Raman signal. The applied magnetic field can be parallel or perpendicular to the sensing surface. The magnetic field strength is ranging from 0.5 to 3000 gauss, or 2 to 100 gauss.

FIGS. 18-21 illustrate a number of examples of the array device. It will be appreciated that the described processes need not to be performed in the order in which they are herein described, but that these descriptions are merely exemplary of preferred methods making the array device. In addition, it is understood and appreciated that the scale of the components and features illustrated in the figures has been exaggerated to facilitate ease of discussion.

Figure 18:
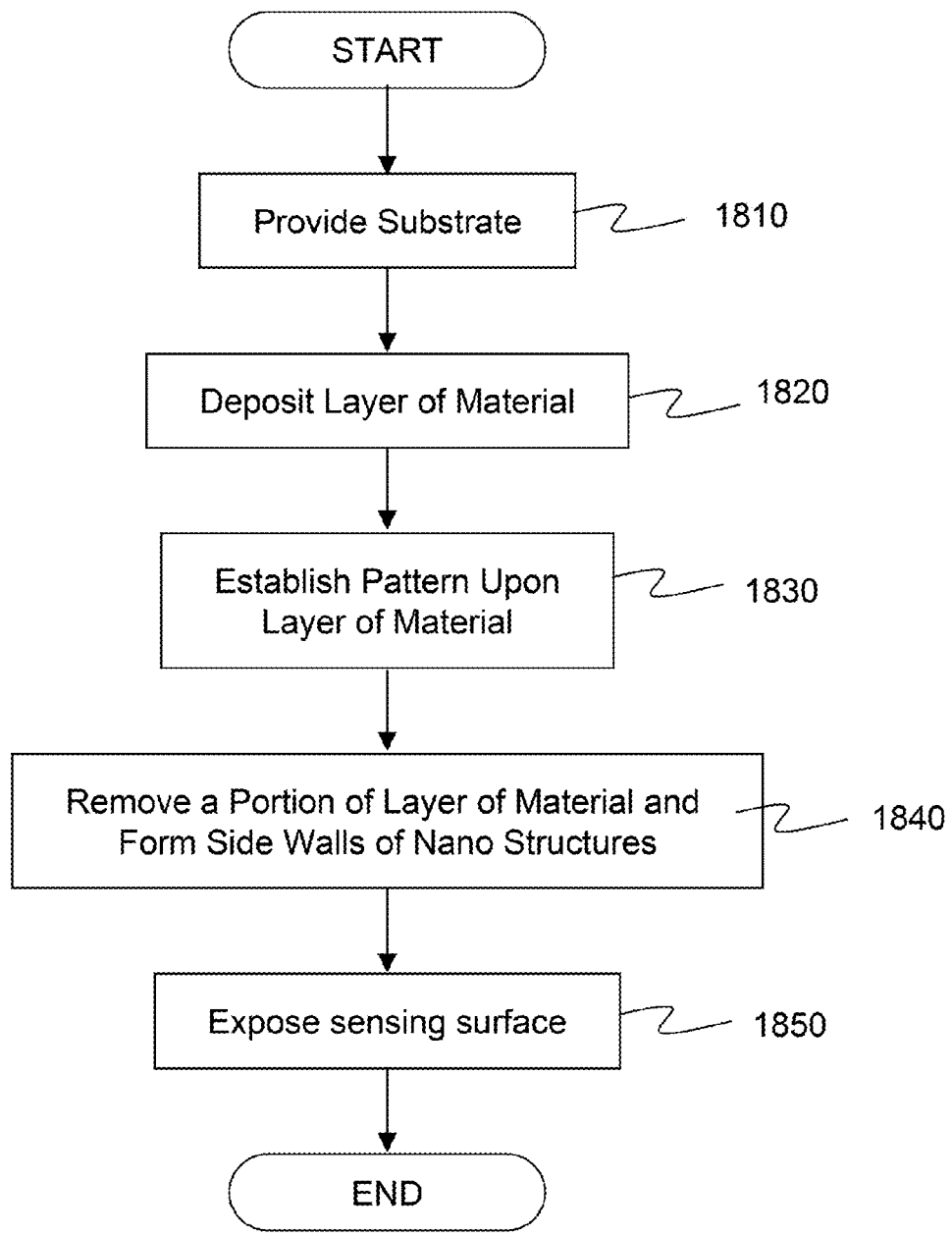
FIG. 18 is a flow chart of a method in accordance with the present invention.

FIG. 18 is a flowchart of a method of forming the array device. As indicated in block 1810, the process is commenced by providing a substrate. In at least one embodiment the substrate is a Si wafer. An inactive material may also be used as the substrate. At least one layer of material is deposited upon the substrate, block 1820. A pattern is then established upon the layer of material, block 1830. The pattern provides areas defining a plurality of nano structures. As in block 1840, a portion of the layer of material are removed, so that side walls of the nano structures are formed. The method further includes forming an exposed sensing surface upon the nano structures, wherein said surface comprises at least one active SERS nano surface and at least one inactive SERS nano surface established in proximity to the active nano SERS surface.

FIGS. 19A-19D provide detailed illustrations for making the nano structures in a sensor array in according to the present invention. The substrate 1900 is made from an inactive material. Alternatively, the substrate can be a non-inactive material with a coating of a layer of an inactive material to provide the inactive SERS nano surface for the completed device.

Figure 19A:
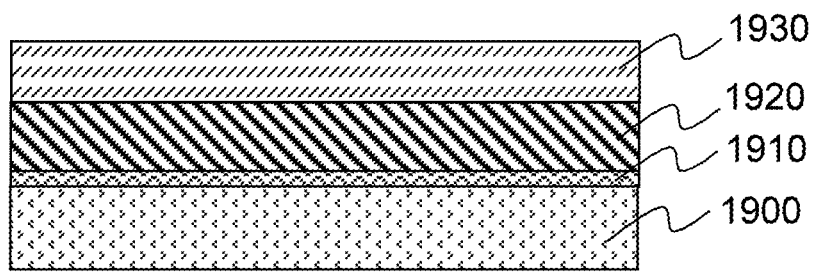
FIGS. 19A-19D show a process for forming an array device in accordance with the present invention.

As shown in FIG. 19A, an optional adhesion layer 1910 is deposited upon the substrate to adhere nano structures onto the substrate. Non-limiting examples of materials for the adhesion layer are Ti and Ni. The thickness of the adhesion layer can be between 10 to 100 nm.

Upon the adhesion layer, a layer of active material 1920 is deposited thereon. The thickness of the active layer 1920 is between 1 nm to 5 μm. In an embodiment, the thickness of the active layer 1920 is between 5 nm to 100 nm. A mask layer 1930 is then deposited on the layer of active material 1920. An example of the mask layer is a layer of photoresist or e-beam resist. An optional metal layer may be established between the resist layer 1930 and active layer 1920 to serve as a hard mask in subsequent processes.

Figure 19B:
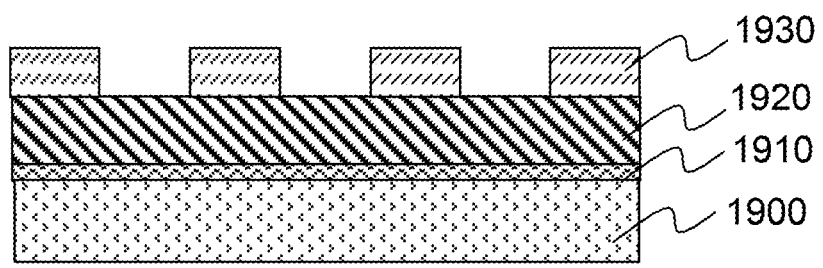

Next, a pattern on the resist layer 1930 is established by a photolithography process or e-beam process (FIG. 19B). Photolithography and e-beam patterning techniques are well known to those skilled in the art and commercially available and need not be described in more detail herein.

Figure 19C:
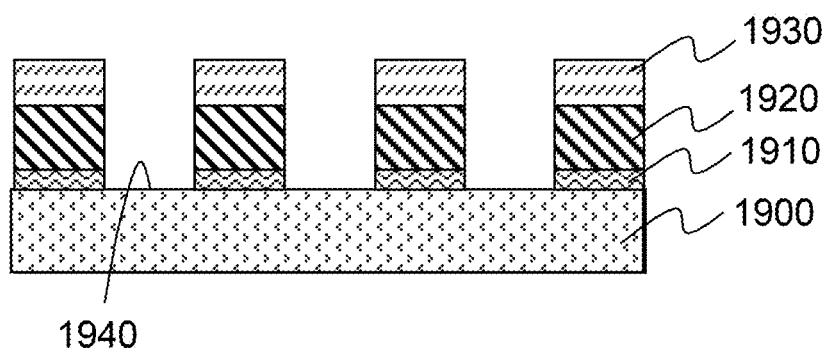
Figure 19D:
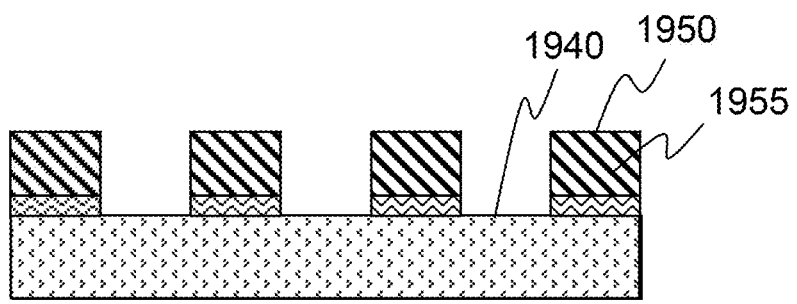

Next, the exposed portion of the active material and the adhesion layer are removed by etching processes such as wet chemical etching or plasma etching (FIG. 19C). The inactive SERS nano surfaces 1940 are formed around nano rods 1955. The remaining mask layer 1930 is finally removed. As shown in FIG. 19D, the completed device has a plurality of nano rods with the active SERS nano surfaces 1950 formed on the top and side wall surfaces of the rods. These active surfaces are surrounded by the exposed inactive SERS nano surface 1940.

In an alternative embodiment, layer 1900 can be an active material and layer 1920 can be an inactive material. The above detailed process can produce a device with an array of nano rods of the inactive material, in which the inactive SERS nano surfaces are surrounded by the active nano SERS surface.

Figure 20A:
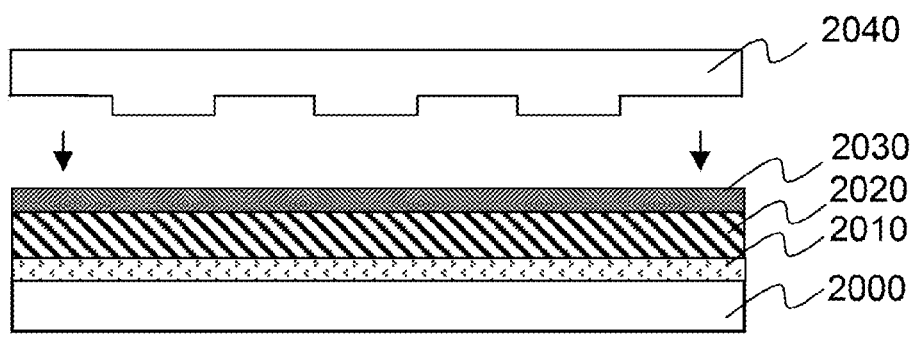
FIGS. 20A-20E show another process for forming an array device in accordance with the present invention.
Figure 20B:
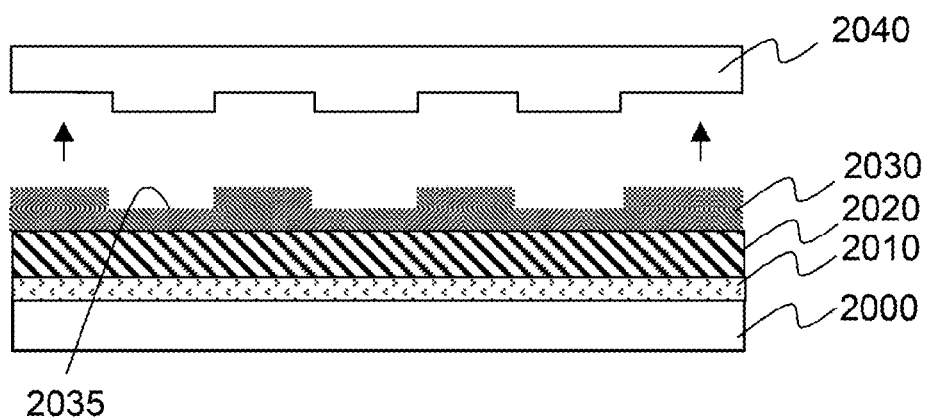
Figure 20C:
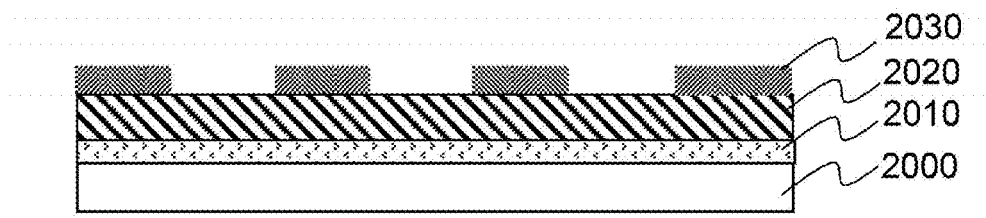
Figure 20D:
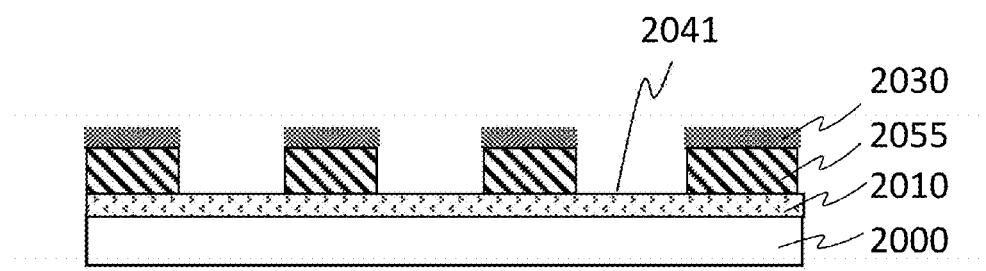
Figure 20E:
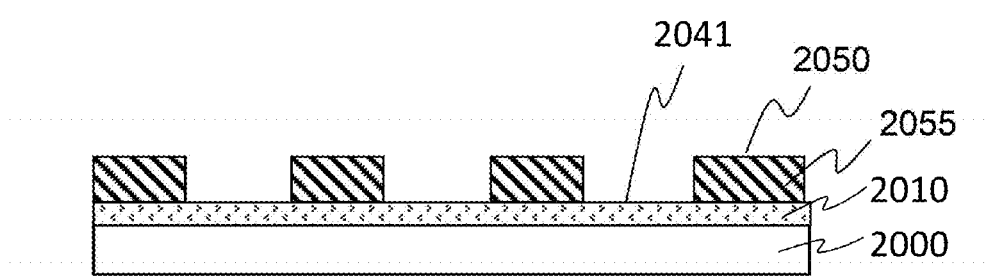

A sequence of steps of yet another embodiment of forming array device is shown in FIGS. 20A-20E. A pattern of the nano structures is defined by an imprint lithography process. The pattern can be produced on a substrate such as a silicon wafer by e-beam lithography and reactive ion etching. The patterned substrate can act as a mold. The pattern in the nano scale is a reverse image of a final nano array. In the first step, a layer of inactive material 2010 may be deposit onto the substrate 2000 to establish the inactive nano SERS surface. A layer of active material 2020 such as Ag or Au is then deposited onto the inactive layer. Then a layer of imprintable material 2030, such as a PMMA or other polymer, is coated on layer 2020. The mold 2040 is then pressed into layer 2030 (FIG. 20A). Imprinting is made during the step after removing the mold (FIG. 20B). In FIG. 20C, pattern transfer is complete using etching to remove residual resist 2035 in the compressed areas. Further chemical etch can be used to etch the metal film in the compressed areas (FIG. 20D). An array of nano surface structure is produced after removing the mask layer. As shown in FIG. 20E, the completed device has a plurality of nano rods with the active SERS nano surfaces 2050 formed on the top and side wall surfaces of the rods. These active surfaces are surrounded by the exposed inactive SERS nano surface 2040.

Figure 21A:
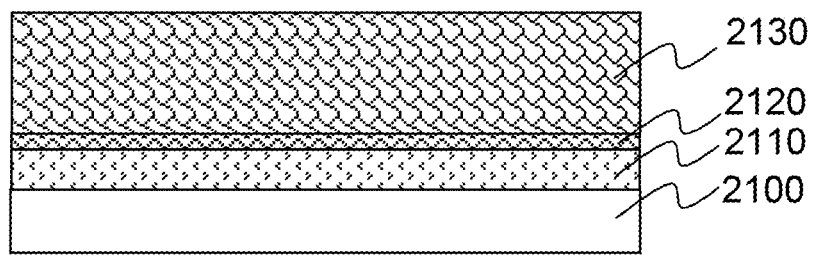
FIGS. 21A-21D show yet another process for forming an array device in accordance with the present invention.

In some embodiments, FIGS. 21A-21D show an array of nano structure formed by anodization process. FIG. 21A shows a stack of layers deposited on a substrate 2100. The substrate 2100 may be a silicon wafer. The first layer 2110 is an inactive material. This layer can be 30-50 nm $SiO_2$ made by oxidizing silicon wafers. Above the inactive layer, an adhesion layer 2120 is deposited. The thickness of the adhesion layer is usually controlled in the range of 100 Å-1,000 Å and optimized to provide best adhesion to a noble metal layer, e.g., an Ag or Au layer. The thickness of the adhesion layer 2120 is also optimized for applying an electric bias to the sensing surface for trace chemical detection and further for applying a lower temperature to the sensing surface to enhance sensitivity of trace chemical detection. Above the adhesion layer, an aluminum layer 2130 with a thickness in the range of 0.5-10.0 micrometers, is deposited. Then an anneal operation is performed on the aluminum layer 145 to recrystallize the Al film.

Figure 21B:
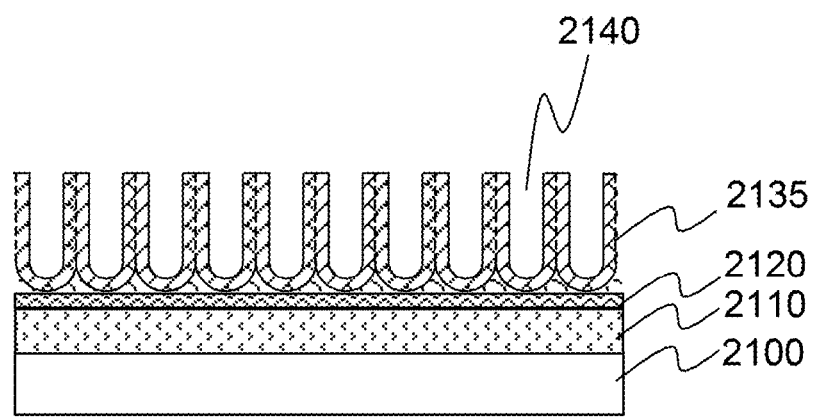

Next, an anodization process is carried out to produce a porous structure 2140 in a form of porous aluminum oxide 2135 (FIG. 21B). In the anodization process, the nano hole or nano rod diameter, the spacing between nano holes or nano rods, D, and the depth of nano hole array or height of nano rod array can be controlled and modified by adjusting operation voltage, current, chemical solution pH value and temperature and process time, etc. The porous structure is formed with naturally self-assembled hexagon-shaped nano pore-array that includes a plurality of pores 2140 surrounded by hexagon-shaped pore wall. Then a wet etch process is performed to widen the pores 2140 and to remove the barrier layer at the bottom of the pores.

Figure 21C:
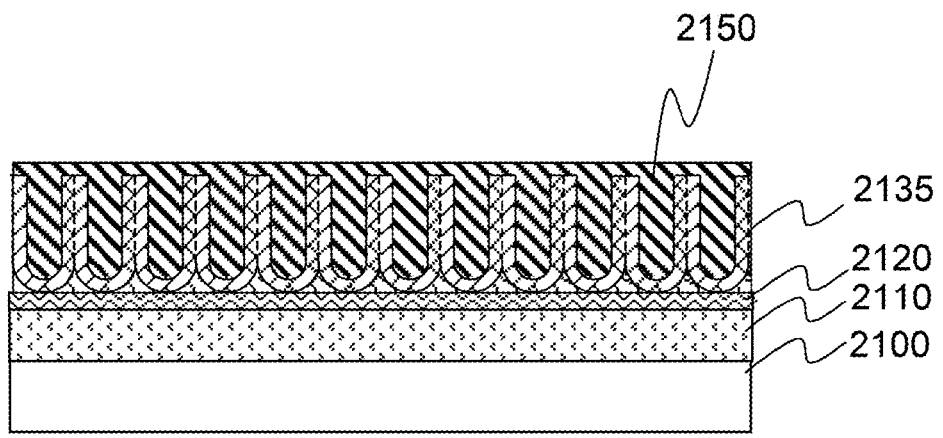
Figure 21D:
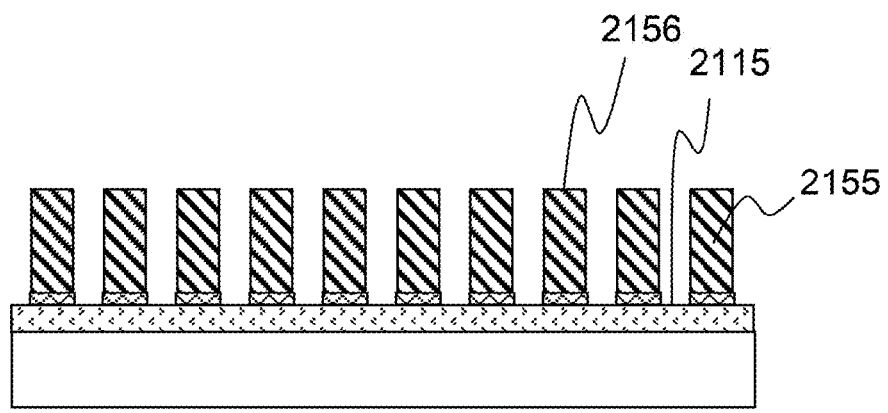

Next, an active material such as a noble metal 2150, such as Ag, Au, or Cu, is deposited to fill the plurality of pores by a physical, chemical, or electro-chemical method (FIG. 21C). A chemical process is then performed to remove the top portion of the noble metal 2150 and the aluminum oxide 2135. A plurality of noble metal columns 2155 are formed on top of the adhesion layer 2120. The exposed portion of the adhesion layer is removed to expose the inactive SERS nano surface 2115 (FIG. 21D). The completed device has a plurality of nano rods with the active SERS nano surfaces 2156 formed on the top and side wall surfaces of the rods. These active surfaces are surrounded by the exposed inactive SERS nano surface 2115.

Figure 22:
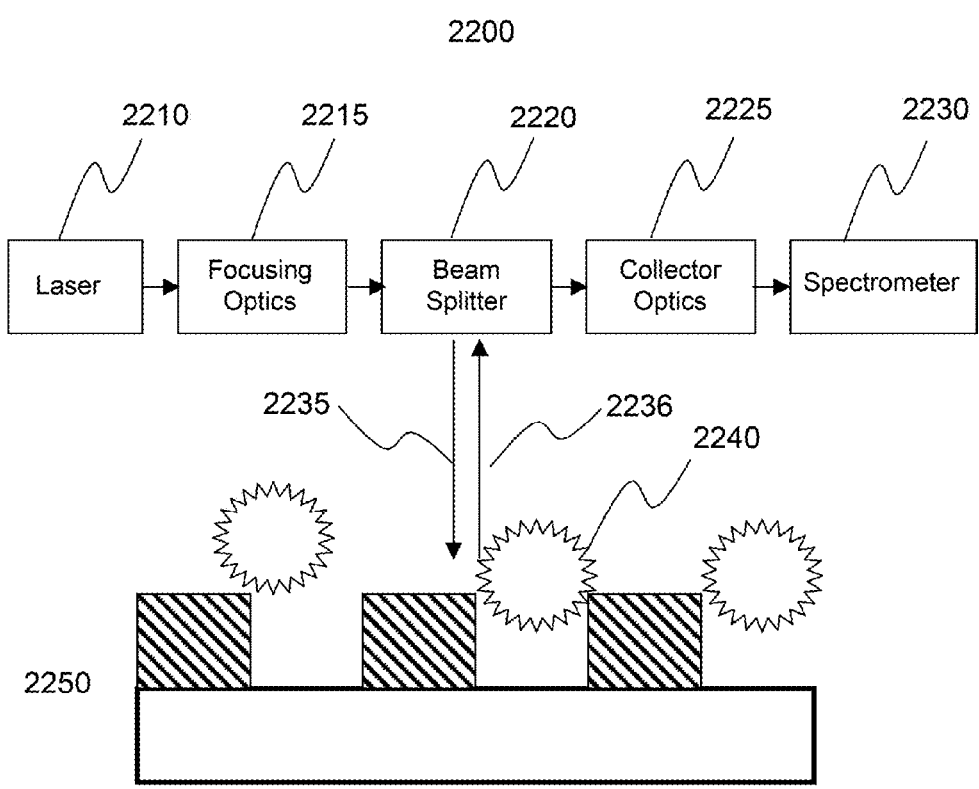
FIG. 22 is a diagram of a SERS system using an array device in accordance with the present invention.

FIG. 22 shows a trace chemical detection system based on the array device in accordance with one embodiment of the present invention. The system includes surface-enhanced Raman spectroscopy (SERS), surface-enhanced Raman resonance spectroscopy (SERRS), surface-enhanced coherent-anti stokes Raman scattering (SECARS), surface-enhanced infrared absorption (SEIRA) spectroscopy, surface-enhanced fluorescence spectroscopy (SEFLS), surface-enhanced photoluminescence spectroscopy (SEPLS), time-resolved above mentioned spectroscopy, other optical spectroscopic methods, and combination of above listed methods, for example, SERS combine with SEFLS or SERS combine with SEPLS, for chemical fingerprint identification and trace chemical sensing.

As shown in FIG. 22, a probe assembly 2200 includes an optical source 2210 such as a laser beam source and an optical assembly 2215 to focus the laser beam. The beam is then deflected by a deflector 2220 to irradiate an array device 2250. The array device 2250 is adsorbed with a chemical substance which is going to be analyzed. Molecules 2240 of the chemical substance adsorbed on the sensing surface of the array device scatter the incoming beam 2235. A portion of the scattered photons 2236 are collected by an optical system. A spectrum analyzer, such as a spectrometer, receives said portion of scattered photons and generates an output indicative of the composition of the chemical substance.

The system illustrated by FIG. 22 can be used in chemical fingerprint identification and trace chemical sensing in the areas of medical/health care, life science, environmental, food safety, forensic, homeland security, etc. For homeland security application at the areas including but not limited to airports, customs, cargos, harbors, trains and train stations, subways, buildings, shopping malls, theaters, resort centers, surface water and other water supply system including wells, the dangerous and harmful chemical compounds can include explosives, nerve agents, blood agents, blister agents, heavy metals and other poison chemicals, e.g., Pb, Cd, Hg, Tl, and arsenic contained compounds, volatile toxins, e.g., benzene, chloroform, pulmonary agents, e.g., phosgene, vinyl chloride, biological agents, toxins, and nuclear weapons. The explosive substances can include TNT, DNT, MNT, DNB, DMNB, EGDN, NG, RDX, PETN, TATP, TATB, HMX, ammonia nitrate, tetryl, picric acid, HNS, etc., and mixtures of two or more items mentioned above, for example, C-4, etc. The dangerous chemical substances also include nerve agents including but not limiting to tabun (GA), sarin (GB), soman (GD), Cyclosarin (GF), Lewisite and VX, etc. The blister agents can include HD (distilled sulfur mustard), etc. The tear agents, including 2-chloroacetonphenone, etc. The blood agents can include cyanides (cyanogen chloride (CK), hydrogen cyanide (AC), potassium cyanide (KCN), sodium cyanide (NaCN), etc.), arsine (SA). The blister agents can include but not limiting to lewisite, phosgene oxime (CX), mustards, etc. The biological agents can include category A agents, e.g., anthrax, *bacillus anthracis* (LD Viable), Ricin, *Yersinia pestis, Burk holderia mallei, Francisella tularensis, Brucella abortus*, smallpox, plagues, category B agents, e.g., Q fever, category C agents, e.g., yellow fever, and Severe acute respiratory syndrome (SARS) and bird flu, etc. The viruses include (but not limited to) Congo Crimea hemorrhagic fever virus, Eastern equine encephalitis virus, Japanese encephalitis virus (JEV), yellow fever virus (YFV), Ebora virus, Equine morbillivirus, Lassa fever virus, Marburg virus, Rift Valley fever virus, South American hemorrhagic fever virus (Junin, Machupo, Sabia, Flexal, Guanarito, etc.), Tick borne encephalitis virus, smallpox virus, virus which can cause Hantavirus pulmonary syndrome; bacteria include (but not limited to) Anthrax bacillus, Cattle, sheep, swine brucellosis, Burke Holder of glanders bacteria (*Pseudomonas mallei*, etc.), *Clostridium botulinum*, Turafrancisrand, the plague *bacillus*, etc.; *Rickettsia* include (but not limited to) *Q Rickettsia, Rickettsia prowazekii* (Cause typhus), *Rickettsia rickettsii*, etc.; Fungus include (but not limited to) *Coccidioides immitis*, etc.; toxins include (but not limited to) Abrin, Aflatoxin, Botulinum toxin, *Clostridium perfringens* toxin, Conch toxins, Two acetyl grass sickle enol toxin, Ricin, Shellfish toxins, Shiga toxin, *Staphylococcal enterotoxin Staphylococcal enterotoxin*, Tetrodotoxin, T-2 toin, etc.

The system based on the array device in accordance of the present invention can also be used in chemical fingerprint identification and trace chemical sensing in environmental application, for example, toxic materials monitoring and screening, including but not limited to inorganic, organic, nitrites and chlorine contained chemicals, such as $NO_2^-$ and $ClO_4^-$ groups and dioxins, benzene, aromatic group and its derivatives, cyanides, heavy metals including but not limited to Pb, Cd, Hg, $Cr^{6+}$ and arsenic contained compounds, and residue pesticides, insecticides, herbicides, and other toxic chemicals in ocean, lake, rivers, reservoir, and wells, and other surface and underground water, as well as in soul and in air.

For environmental protection, the disclosed chemical sensing system can be used for outdoor and indoor pollution monitoring and screening emission sources. Outdoor pollution includes auto vehicle exhaust gas, factory exhaust gas and liquid, etc. Indoor pollution monitoring and screening in both family houses and workplaces, including but not limited to building, airplane, space shuttle, boat and ship, submarine, and all other areas under the ceiling. Application includes but not limits to monitoring and screening air quality and other health problems associated with plastic floor, wall painting and decoration, painted furniture, plastic household, tools, toys and all other plastic materials indoor which may contain toxic materials, for example, benzene, its derivatives and other volatile organic compounds (VOC), polyvinyl chloride (PVC) and its plasticizer additives including phthalate, DEHA family, and heavy metals, etc.

For medical applications, non-invasive or minimal-invasive early disease screening test and diagnosis can be accomplished using the disclosed array device in accordance of the present invention. For example, test through human skin test, eye test, or body fluid test, including saliva, sweat, blood, and urine test, and human breath test to early detect diseases, including but not limited to lung cancer, breast cancer, oral and head cancers, ulcer, bronchial, oesophageal and stomach cancer, colon cancer, skin cancer, diseases of liver, kidney, pancreas, bladder, prostate, uterine, esophageal disease, oxidant stress, eye disease, diabetes, schizophrenia, lipid peroxidation, asthma, tuberculosis, helicobacter pylori, etc. Noninvasive or minimal-invasive test can be also applied to screening test and diagnose Alzheimer's disease.

The disclosed systems and methods are applicable to urine test by "Smart Toilet" equipped with SERS sensor to early detect diseases, including but not limited to prostate cancer, diseases of bladder, uterine, etc., and to monitoring and screening illicit drugs.

The disclosed systems and methods are applicable to human and animal body fluid test. For example, saliva test for oral cancer, blood test for early disease screening test or diagnosis, including but not limit to Alzheimer's disease, Parkinson disease, HIV, mad cow disease, cardiovascular disease, cancers, and rapid pathogen, virus or bacteria, identification and screening, including but not limited to SARS, bird flu, smallpox, HIV, anthrax, ricin, etc.

Raman screening test and diagnosis method can be applied to real time doctor visiting procedure, such as disease screening or special disease diagnosis. In this way, doctor is able to make judgment based on real time Raman test during patient visit, and make on timely decision for necessary medical treatment.

The disclosed systems and methods can be used during surgery, real-time in-line identify cancer tumor portion, rather than usually applied biopsy method which requires time, distinguish the boundary between cancer tumor portion and health portion to real-time support doctor to make decision on cutting location.

The disclosed systems and methods can be used in pharmaceutical applications in medicine R & D, manufacturing and quality monitoring. Raman method can be also applied to medical treatment, for example, medicine taking feedback process, surgery, Chemotherapy, Radiotherapy, etc. For example, before a medical treatment, like patient taking medicine and after patient taking medicine at different period of time, Raman test can be carried out to investigation effectiveness from medicine, then the result can be fed back to a doctor to modify prescription type and dose for the best medical treatment to different patients, respectively, with different level of medical treatment metabolism efficiency level.

The disclosed systems and methods are compatible with a miniaturized Raman sensor with wireless technology used inside human body. For example, a system-on-chip Raman system can be made in a tablet size which includes on-chip mini-laser source, MEMS based mini-spectrometer, wireless module, mini-probe, etc. Initial application will be disease screening test and diagnosis of digest system. For example, patient or a person being screened swallows a tablet sized Raman system after his/her digest system got cleaned (similar procedure to that of preparation for colon endoscopy test). Raman scans will be taken timely, for example, from every one minute to every hour a time. Then data will be transferred by wireless module, and a computer outside human body will receive Raman data and analyze, search, match, and decision making. The next stage of application is minimal invasive with a needle shaped probe head to bring mini-Raman sensor into diagnosis area inside human body. Raman data can be transferred through optic fiber, or wireless module. Applications include but not limit screening test and diagnosis of breast cancer, Alzheimer's disease, etc.

The disclosed systems and methods can be used in biotechnology and biomedical applications, such as fingerprint identification of DNA, RNA and protein, DNA sequencing, DNA sorting, etc.

The disclosed systems and methods can be used in forensic applications such as drug test and screening through saliva test, urine test, or powder test; false signature recognition; human identification and screening by DNA profiling; identify microscopic paint fragments, fiber identification, etc. The disclosed systems and methods can be used in drug screening through human body fluid test, or/and breath test by Raman method based on the array device in accordance of the present invention is developed.

The disclosed systems and methods are applicable to food, fruit and beverage monitoring and screening application, monitoring of chemicals in gas, liquid, power, gel, aerosol, or solid phases, including but not limited to ethylene, for stored fruits and vegetables with longer shelf time application; food safety, monitoring and screening harmful chemicals including but not limited residue pesticides (e.g., methamidophos, cypermethrin, deltamethrin, malachite green, etc.), dioxins, illegal artificial additives (e.g., Sudan I, Sudan II, Sudan III, Sudan IV, etc.), food processing by-products (e.g., acrylamide formed from potato chips from processing temperature over 120° C.) by Raman method based on the array device in accordance of the present invention is developed. Those chemicals include but not limit to acrylamide, malachite green, etc. Foods under investigation include but not limit to potato chips, French fries, fried potato, potato crisps, cookies, crackers, cereal products, crisp bread, bread, coffee, prepared toast, roasted nuts, biscuits, chocolates, popcorn, and aquatic products including fish, etc.

The disclosed systems and methods are applicable to identifying and monitoring food packaging processing and preparation materials, including but not limited to identify and screen polyvinyl chloride (PVC) and phthalate materials used as the microwave food wrap, kitchen film, food packaging, processing and preparation materials.

The disclosed systems and methods are applicable to screening counterfeit merchandizes and materials, including but not limited to medicines, drugs, milk-based powders, edible oil, wines, gemstones, currency bills, false signature through inks, art pieces, gasoline, etc.

The disclosed systems and methods are applicable to industrial process quality and production safety monitoring. Application areas include but not limited to process control for product quality, process and production safety at gas and wet chemical process lines, for example, petroleum refinery plant, chemical engineering manufacturing plant, semiconductor wet chemical process line in clean room, airline and space shuttle, boat, ship and submarine, etc.

The disclosed systems and methods are applied to determine the locations of chemicals. For example, a sensor or sensor network can be placed at different locations including but not limiting to medical doctor clinic office, surgery operation room, shopping center, public resort area, building, custom, road check station, harbor, airport, vehicle, boat and ship, airplane, space shuttle, industrial process site, R&D research lab, quality control office, college lab and office, surface water, well, ground water, hand carried by operation people, and so on.

Chemical sensing application engineering, not only single chemical sensor is placed on site, but chemical sensor network is designed and arranged to cover application area which all sensors are controlled by sub-central controllers and main-central controller connected with fiber optic or/and wireless system. When abnormal result is found, an alarming signal is automatically triggered in the forms including but not limiting to red color blinking on screen of a computer or PDA, alarming sound in key area, sending alarming E-mail to key people, triggering a phone call to key people cell phone, etc. The abnormal result can be classified into different risk level, for example, green (safe), blue, yellow, orange, red (the most risk).

EXAMPLES

The disclosed system and methods are further described in the following examples, which do not limit the scope of the invention described in the claims.

Example 1

Fabrication of Nano-Surface Arrays by Anodization Method

A thin film of Ti (about 100 nm) was deposited by e-beam evaporation of Si (100) wafer, followed by the deposition of Ag (about 100 nm). Then a 500 nm Al layer was deposited over the Ag film using physical vapor deposition method.

Then the coated Si wafer was placed into an anodizing bath with 0.3 M oxalic acid solution as the electrolytic solution. The bath was maintained at 10° C., and the anodizing voltage was set at 35 V. After anodization, nano-size narrow pores were formed in the $Al_2O_3$ layer. The diameter of the pores (or holes) can be widened by placing the wafer into a 10 wt. % phosphoric acid solution. The nano pore structure in the $Al_2O_3$ layer acted as a mask for etching active metal layer or depositing active metal layer. Thus a nano surface array was formed after removing oxidized Al layer.

Example 2

Nanoimprint Lithography for Fabrication of Nano-Surface Arrays

The first step in nanoimprint is to press a mold into a thin resist cast on a substrate. The step is to duplicate the nanostructure on the mold in the resist film. The second step is to etch the resist film to form the nanostructure on the substrate.

The mold was patterned with an array of nano dots of 30 nm in feature size using electron beam lithography and reactive ion etching (RIE) on a Si wafer. PMMA was used as the resist on Au coated Si (100) wafer. A thin Ti layer was inserted between Au and Si to improve adhesive. The imprint process was carried out in vacuum at a temperate around 160° C., above the glass temperate of PMMA, at a pressure about 1000 psi. After the pattern from the mole was transferred to the Au coated Si (100), oxygen RIE was used to remove residue resist in the compressed areas in PMMA. Then, the pattern was etched into the Au film. After removing the PMMA, a nano-hole array was formed in Au.

Example 3

1) Demonstration of Nano Array

Figure 24:
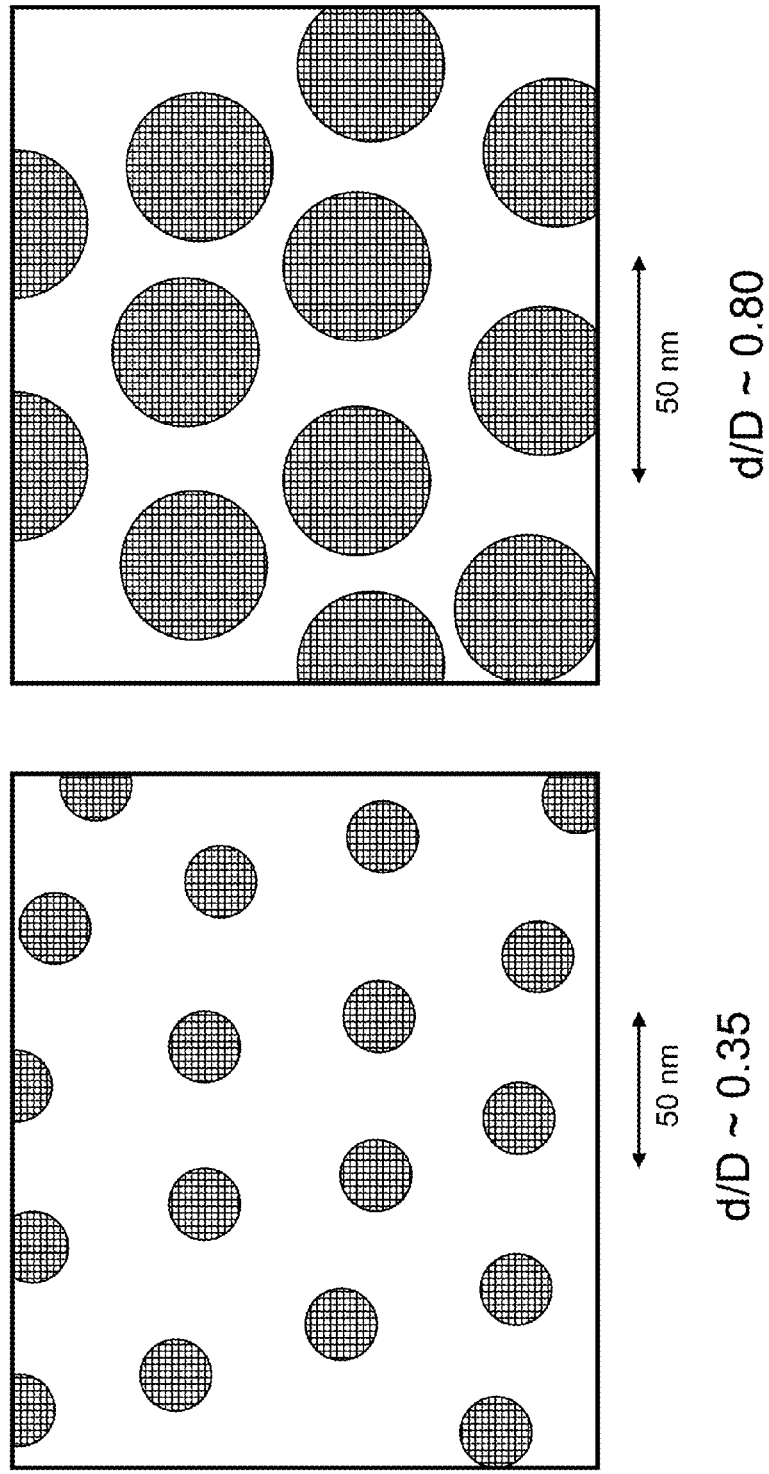
FIG. 24 shows scanning-electron micrographs (SEM) obtained from the top-view of a surface structure, where d is the average diameter of nano holes, and D is the averaged center-to-center distance between adjacent nano holes.

FIG. 24 is an example of scanning electron microscopy imaging of such nano surface arrays. The left image shows an array of nano-holes with 17 nm diameter and about 30 nm spacing. The image on the right shows an array of nano-holes with 38 nm diameter and about 10 nm spacing.

2) Demonstration of Surface-Enhanced Raman Using the Nano-Surface Arrays

Figure 23A:
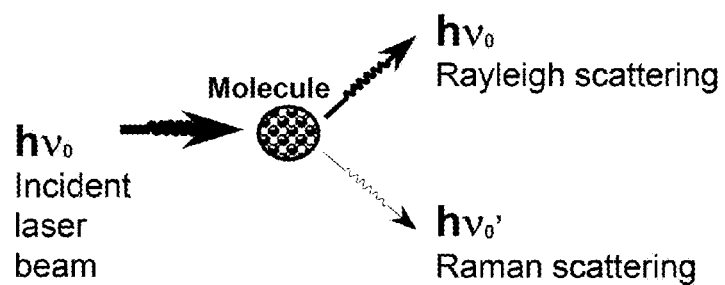
FIGS. 23A and 23B are schematic diagrams respectively showing the physical mechanism of Raman scattering and a Raman experiment setup.
Figure 23B:
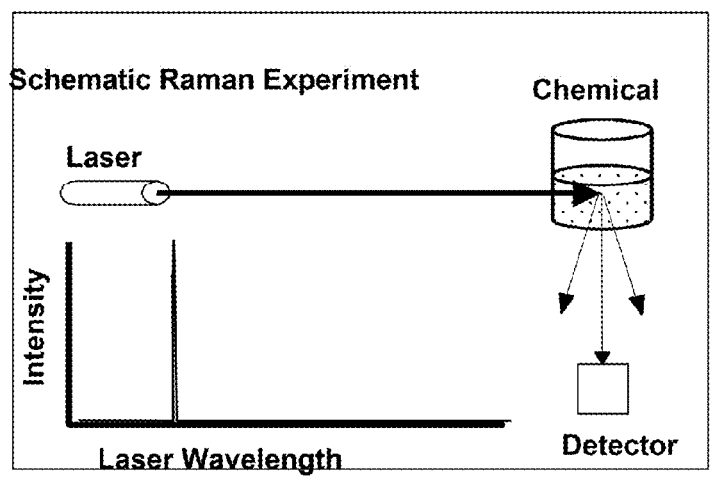

A Raman scattering system, as shown in FIG. 23B, includes a Raman nano-surface array on silicon, a semiconductor laser, which can collect the reflected lights on the surface. The sampling methods include: the array is placed in a solution container or a gas probe cell; or is just lie down horizontally, then to inject liquid chemical onto the surface; or the array is covered by a layer of glass or polymer without physical contact, liquid or gas sample is injected through a microfluidic channel.

Figure 23C:
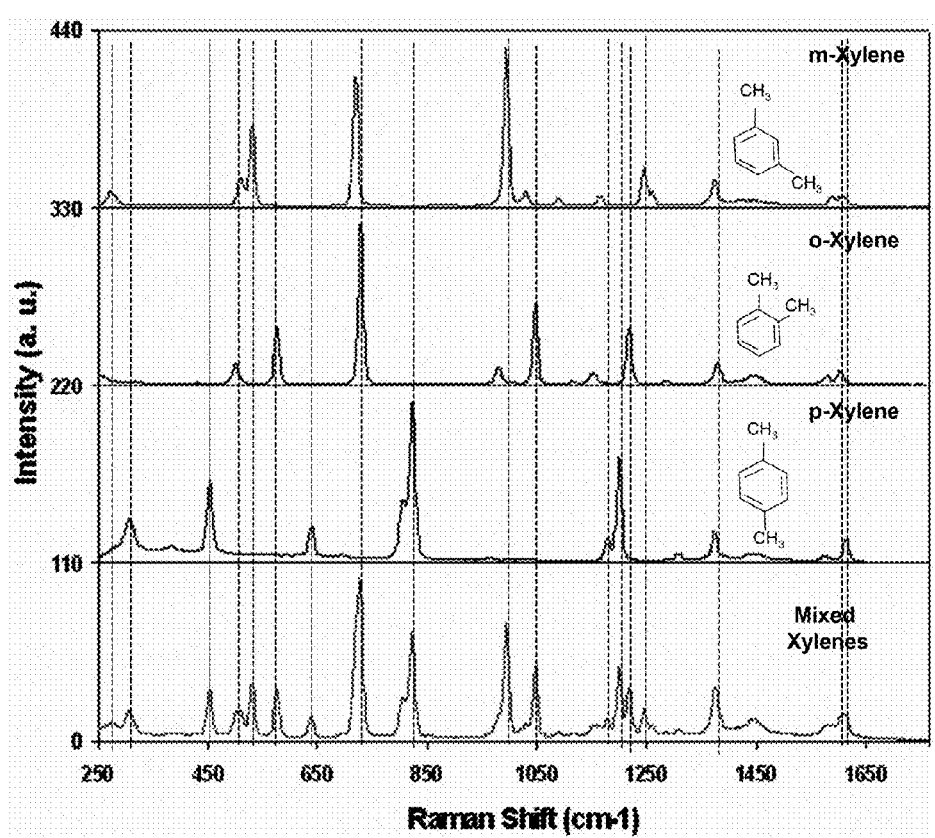
FIG. 23C also shows exemplified Raman spectra obtained from different chemicals.

FIG. 23C shows Raman spectra of xylenes. In this example, Raman spectrum of m-xylene, o-xylene, p-Xylene, and mixed xylene are demonstrated separately. As shown in FIG. 23C, each chemical has its own chemical spectral fingerprint, even though the mass of those different xylenes are exact the same. On the other hand, Raman spectrum of mixed xylene shows little interference among those 3 different xylenes. Then, each chemical can be distinctively identified, therefore, Raman methods is one of the best chemical identification ways with spectral fingerprint capability.

Figure 25:
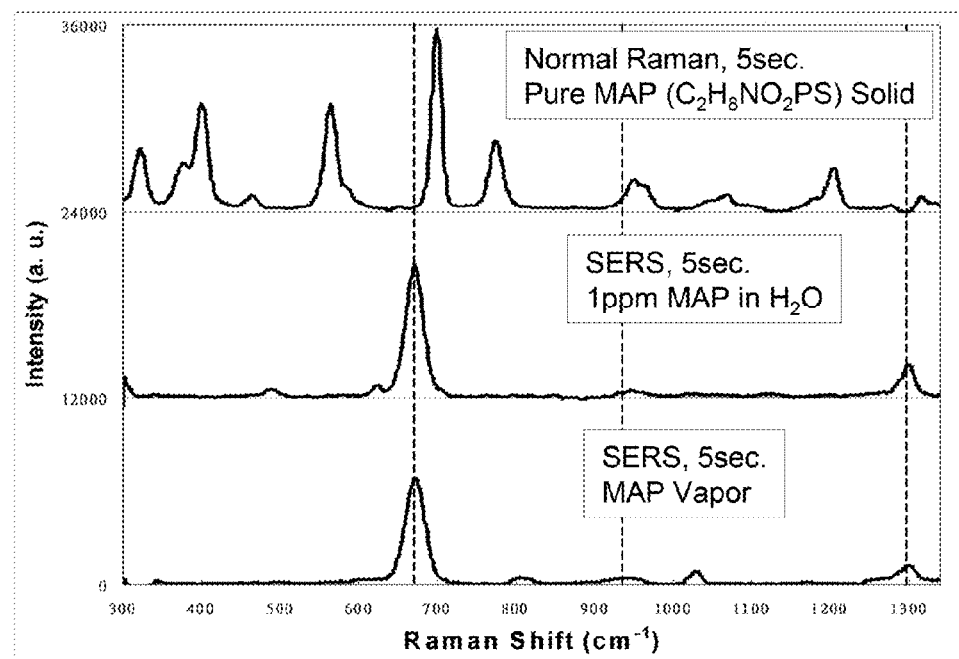
FIG. 25 shows a normal Raman spectrum and SERS spectra of methamidophos.

Another experiment was carried out using methamidophos (MAP) which is a key pesticide; nerve agent stimulant. A trace amount of the chemical is introduced in liquid phase and vapor phase, respectively. The SERS spectra of these samples are compared against normal Raman spectrum of a pure MAP solid sample. As shown in FIG. 25, both liquid sample and vapor sample show MAP spectrum signature. It demonstrates that MAP vapor detection sensitivity is better than 40 parts per billion (ppb).

Monitoring Network System

In some embodiments, a monitoring network system 2600 includes a central office 2610, a mobile detector 2620, and an analysis lab 2630. The central office 2610 can be operated by a government responsible for food safety, environment monitoring and protection, public health, public security, and crisis preparation and warning agencies, etc. The central office 2610 can be run an independent institution that manages quality control for industrial production of food, drinks, medical drugs, petroleum products, and other industrial products, distribution center for commercial products, etc. The mobile detector 2620 can include a portable detector carried by inspection personnel, or a detector system on a vehicle, which are suitable for collecting and detecting harmful substances in the field. The mobile detector can be positioned at distribution centers for food and other commodities, grocery stores, shopping malls, cinemas or sport facilities, or inspection stations on highways, or at border control, airports, bus stations, subways, and train stations, etc. The mobile detector 2620 includes a probe 2621 and an ID reader 2625.

Figure 26:
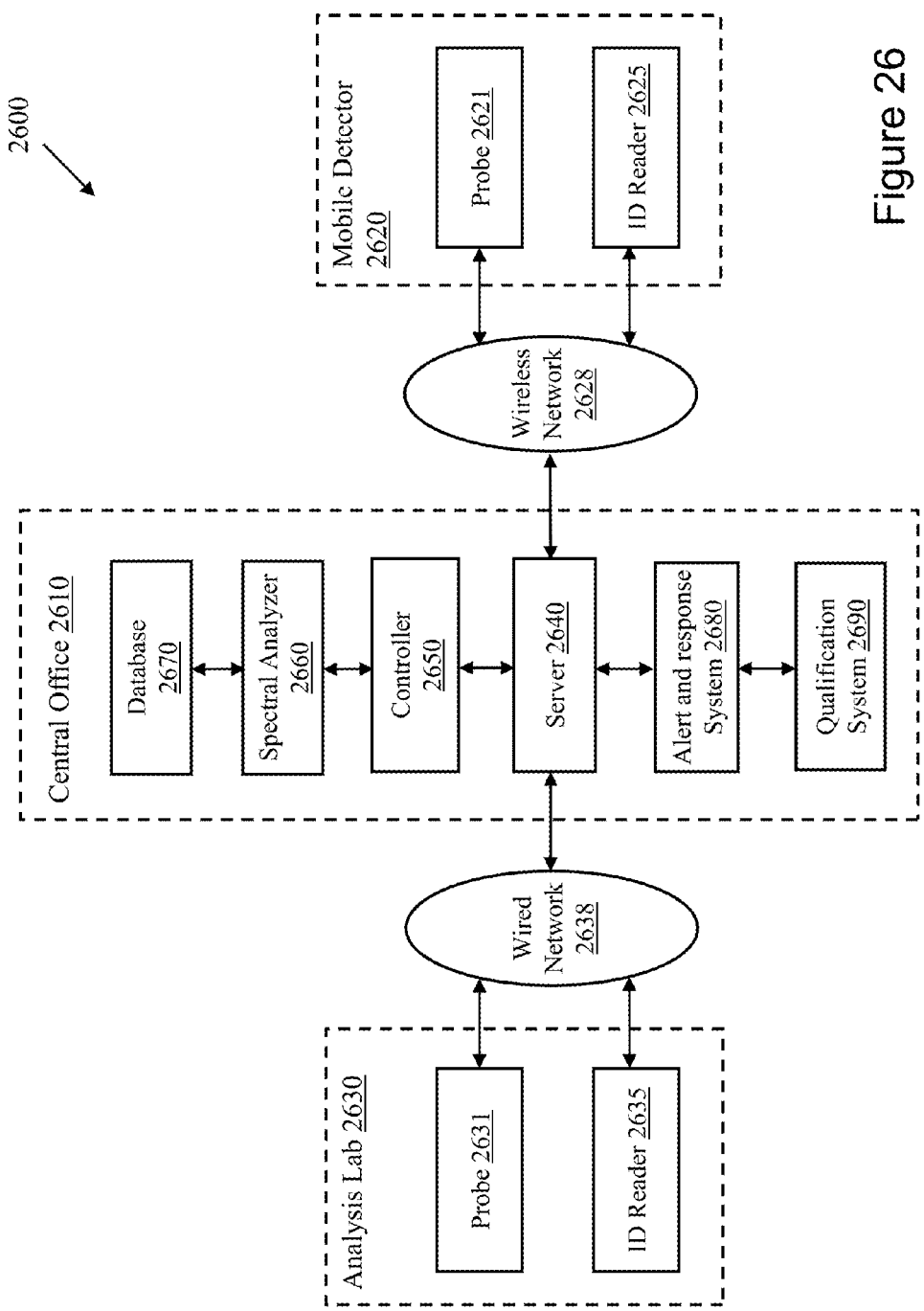
FIG. 26 is a block diagram of an exemplified monitoring network system in accordance to the present invention.
Figure 27:
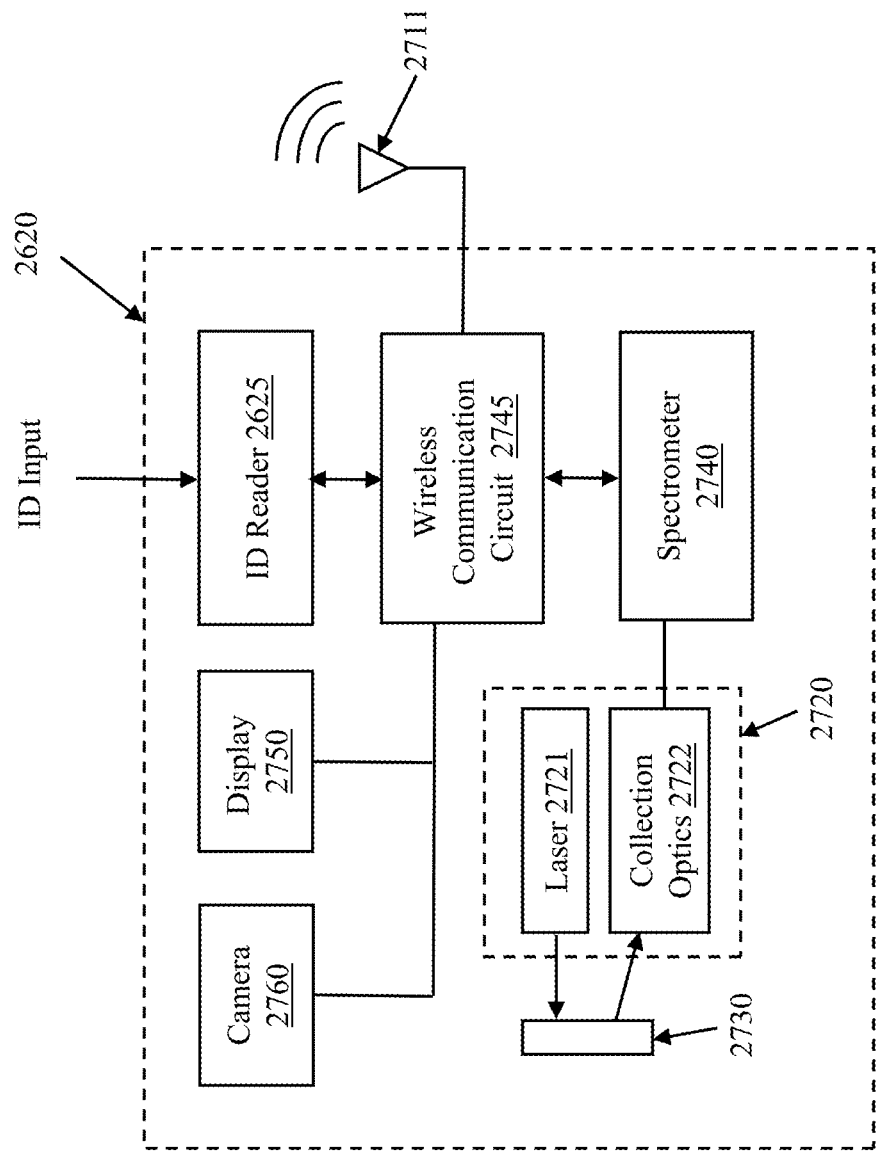
FIG. 27 shows the details of an exemplified mobile detector in accordance to the present invention.

The mobile detector 2620, as shown in FIG. 27, can include a probe head 2720 and a sensor 2730 positioned adjacent to the probe head 2720. The sensor 2730A includes nano-structured surfaces that can adsorb molecules of the substance in the sample or in the ambient environment. The nano-structured surfaces in the sensor 2730 can include an array of active SERS nano surfaces and inactive SERS nano surfaces on a substrate or nano particles on a substrate surface, or the nano particles in a test reagent, as disclosed above in relation to FIGS. 1-25, and FIGS. 30-33 below. The sensor 2730 can also include nano particles in a solution, wherein the sample is introduced in the solution to allow sample molecules to be adsorbed onto the nano particles. The probe head 2720 includes a compact laser 2721 (e.g. a semiconductor laser) configured to illuminate a laser beam on the sample molecules adsorbed on the sensor 2730. The probe head 2720 further includes collection optics 2722 that can collect light scattered from the sample molecules adsorbed on the nano-structured surfaces. The scattered light comprises information about the sample molecules. The probe head 2720 can also include a compact spectrometer 2740 configured to produce a spectrum of the scattered light collected by the probe head 2720. The spectral data is output from the spectrometer 2740 to a wireless communication circuit 2745. The wireless communication circuit 2745 can include an RF transceiver, one or more amplifiers, and impedance matching circuit. The wireless communication circuit 2745 is coupled to an antenna 2711 configured to transmit the spectral data to the central office 2610 via a wireless network 2628 (FIG. 26). The communication can be encrypted in secure protocols.

The ID reader 2625 can be in different formats such as includes non-contact reader such as RFID reading device, a mobile phone, a camera phone, a barcode scanner, an image object recognition system, and a computing device dedicated for inspection and monitoring purposes, etc. The ID reader 2625 can be integrated with the spectrometer 2740 and the probe head 2720, or standalone and in wired or wireless communication with the wireless communication circuit 2745. In some embodiments, the wireless communication circuit 2745 is integrated with the ID reader 2625 (and the display 2750). The spectrometer is connected or in wireless communication with the ID reader 2625.

The ID reader 2625 can receive identification information about the sample such as product model number, batch number, the location of the sampling and substance detection, information about the source of the sample such as the original farm or ranch where the food come from or the manufacturer of a food product, carrier information (e.g. vehicles, trains, ship, airplanes) and the destination of the sample material. The identification can be received in the forms of 1D barcodes, 2D barcodes (i.e. matrix code), alphanumeric numbers, text, etc. The sample ID information is transmitted to the central office 2610 in conjunction with the spectral data of the respective samples. The ID reader 2625 can also receive from the carrier, distributor, or manufacturer of the sample information about pesticide and insecticides applied on the foods being detected, information about animal feeds and antibiotics used on inspected animals and poultries (meat and eggs) and water products.

The mobile detector 2620 can include a display 2750 for displaying instructions for conducting the spectral measurements and messages from the central office 2610. The mobile detector 2620 can include a digital or video camera 2760 which can be combined with the ID reader 2625 or as a separate device. The camera 2760 can take a picture of the commodity that contains the sample material, the vehicle's license number that carries the sample material, the sample or product ID, the driver's license etc. The camera 2760 can also continuously take video images of a site to detect suspicious personnel in correlation with the detection of the harmful materials.

The mobile detectors 2620 can be located within a short range (e.g. within hundreds of yards or a couple of miles) from the central office 2610 to allow wireless signals comprising the spectral data to be communicated in a wireless protocol such as WiMax, WiBro, WiFi, WLAN, 802.11, 802.16, and others. The mobile detectors 2620 can also be located at a long distance from the central office 2610, wherein the wireless signals comprising the spectral data can be communicated using wireless communications standards and protocols such as 3G, 4G, Global System for Mobile communications (GSM), Universal Mobile Telecommunications Service (UMTS), and Code Division Multiple Access (CDMA). GSM can include GPRS, EDGE and CSD. UMTS can include Wideband Code Division Multiple Access (WCDMA), High-Speed Packet Access (HSPA), High-Speed Downlink Packet Access (HSDPA), UMTS-TDD, and Long Term Evolution (LTE). CDMA can include CDMA2000, and Ultra Mobile Broadband (UMB).

Referring to FIG. 26, the analysis lab 2630 can be used for detailed analysis or harmful substances collected from the field or at a large industrial manufacturing sites or distribution center where a high volume of samples need to be analyzed. The analysis lab 2630 can include one or more probes 2631 and one or more ID readers 2635. The probe 2631 and the ID reader 2635 can have structures similar to those illustrated in FIG. 27. The probe 2631 and the ID reader 2635 can communicate with and send spectral data and sample ID information of the samples to the central office 2610.

Figure 28:
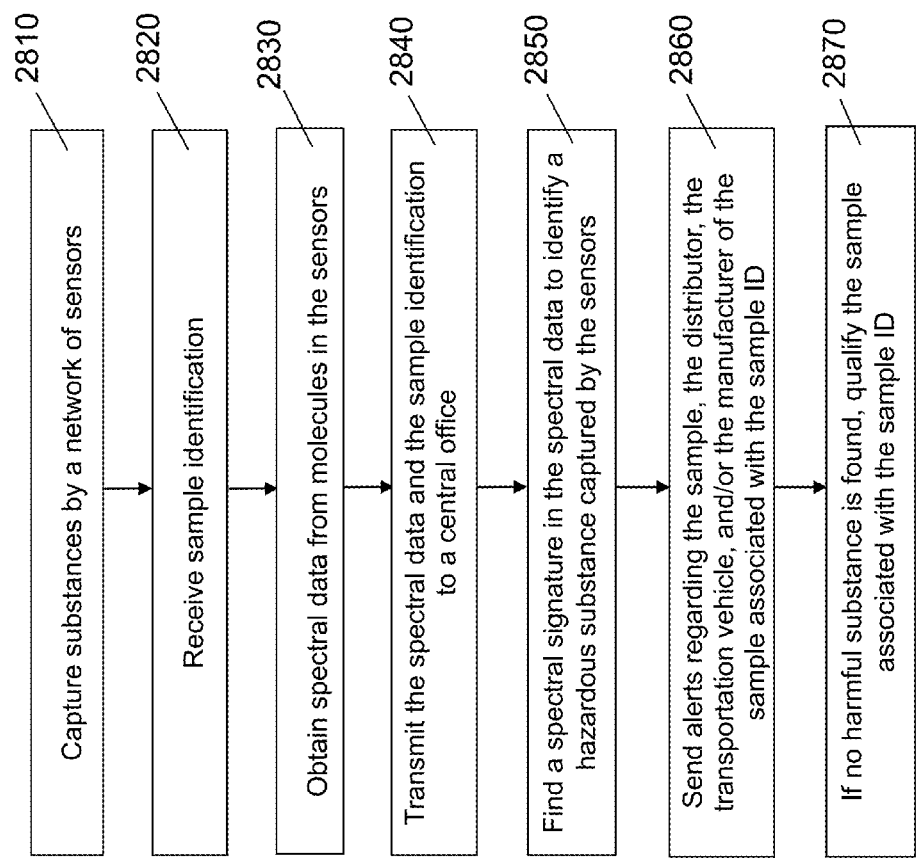
FIG. 28 illustrates an exemplified process for the operations of the monitoring network system.

In some embodiments, referring to FIG. 28, a network of probes can be positioned at grocery stores, shopping malls, transportation stations, border control, a check station on a road, a harbor, an industrial site, a school, or a water source, etc., as described above. Each probe includes a sensor and a probe head. The sensor includes nano structured surfaces to which the molecules can be adsorbed. The probe head is configured to emit a laser beam and collect scattered light from the molecules collected by the sensor. The probe can include a spectrometer for producing spectral data such as Raman spectrum from the scattered light. An ID reader can receive identification information about the sample, the manufacturer, the distributor and carrier of the sample, and/or the destination of the sample.

The sensors in the network capture substances from samples or their perspective environment (step 2810). The samples can include food, drinks, medicine, materials used or produced in manufacturing, water, air, and soil samples from the environment, and samples for forensic and security examinations. The harmful or hazardous substance can include unauthorized additives, residues of pesticides, insecticides and antibiotics in food products, illicit drugs, explosives and flammable materials, a poisonous gas and other harmful chemicals, and contagious virus and bacteria.

Specifically, the sample material can be extracted from a food product such as dairy products, candies, cookies, drinks, alcohol, meat, seafood, tea, fresh or canned vegetables, fruits, grain products, cereals, corn chips, potato chips, or protein containing food. The dairy products can include milk, milk powders, cheese, cheese-containing cakes, yogurts, ice creams, milk containing candies, or cookies, wherein the harmful substance includes melamine, melamine cyanurate, sodium cyclamate, sodium cyclohexylsulfamate, cane sugar, starch, nitrite, nitrate, sulfide, Sudan I, II, III and IV, malachite green, methomidophos, acephate, DDT, DDV, malathion, fenitrothion, malathion, malathion, carbofuran, brodifacoum, tetramethylenedisulfotetramine, sodium fluoroacetate, fluoroacetamide, chlorphacinone, pindone, diphacinone, amitraz, monocrotophos, phorate, disulfoton, phosmet, parathion, fenthion, phosphamidon, diazinon, aldicarb, trichlorfon, aldrin, bentazone, deltamethrin, cypermethrin, methyl parathion, phosmet, dimethoate, nitrofuran, furanzolidole, chloramphenicol, chlortetracycline, ciprofloxacin, clenbuterol, ractopamine, enorfloxacin, rhodanmine B, benzoic acid (sometimes found in milk products), hyposulfurous acid, sodium formaldehyde, formaldehyde, phthalates, dioxins, Pd, Cd, Hg, As, and Cr in water, cyanides, chlorates, sulfates, crysoidine G, boric acid and borax, sodium sulfocyanate, lead chrome green, Basic Flavine O, industrial used formaldehyde and NaOH, carbon monoxide, sodium sulfate, industrial surfer, industrial dyes, fructus papaveris, over dosed level of food colorants (e.g. carmine, lemon yellow, allura red AC, sunset yellow, etc.), food preservants, sweeteners (e.g., saccharin sodium salt, Sodium cyclamate), emulsifier (sucrose easter of fatty acid, etc.), swelling agents overdose ($KAlSO_4$, $NH_4AlSO_4$, etc.), bleach, sulfer suffumigation, color protectants (nitrate, nitrite, etc.), $TiO_2$, benzoyl peroxide, olaquindox, chloromycetin, and $KAlSO_4$.

Molecules of the captured substance are adsorbed on the nano structured surfaces of the sensors. The sample identification is next obtained (step 2820). The sample identification can include information that identifies the sample, and the source, distribution channel and method, and the destination of the sample.

Spectral data are next obtained from the molecules adsorbed to the nano structured surfaces of the sensors (step 2830). As described above, a laser beam is emitted by a laser in the probe assembly (such as the one shown in FIG. 22) to illuminate the molecules adsorbed on the nano structured surfaces on a sensor or in a sample solution. Light scattered by the molecules is collected by the probe assembly. The spectral data is obtained from the scattered light by a spectrometer in the probe assembly. An example for the spectral data is Raman spectrum. The nano structured surfaces on the sensor provide surface enhancement to the signal intensity in the Raman spectrum. The substance capture and associated spectral data can be conducted per sample, or periodically (e.g. at 1 min, 10 min, 15 min, or 1 hour intervals).

The spectral data and the sample identification are next transmitted from the sensors to a central office (step 2840) in wired, wireless or other medium. Referring to FIGS. 26 and 28, the central office 2610 can include a communication device such as a server 2640 configured to communicate with the mobile detector 2620 and the analysis lab 2630. A controller 2650 can handle the data to and from the mobile detectors 2620 and the analysis lab 2630, and can control various tasks for a spectral analyzer 2660, a database 2670, the alert and response system 2680, and a qualification system 2690 under predetermined guidelines or policies stored in the database 2670.

The database 2670 stores spectral signatures in association with harmful substances. The spectral analyzer can identify the spectral signatures of known harmful substances in the spectral data, which determines the existence or non-existences of the harmful substances in the samples (step 2850). The results of the spectral analyses are stored in the database 2670 in association with their respective sample IDs under the control of the controller 2650. The database 2670 can store records for different manufacturers, producers, distribution channels, retailers, grocery stores, etc. Problematic entities or locations can be checked more frequently.

If one or more spectral signatures associated with a harmful substance are found in spectral data, the harmful substance is identified in the sample of a product (step 2850). The result is stored in the database 2670. The controller 2650 can ask the analysis lab 2630 to confirm the finding. The controller 2650 can direct the alert and response system 2680 to send out alerts to operators, the mobile detectors 2620 and other mobile devices in the field, to the check points of the distribution channels for the sample products, to the destination of the sample product, or the manufacturing location of the sample product (step 2860). The alert messages can be displayed on the display 2750 in the mobile detector 2620 so that the in-field operator can take appropriate actions such as stopping the shipment of the lot of material containing the detected harmful material. The warning signal can be in the form of emails, text messages, and voice phone call, etc.

The alert and response system 2680 can generate a "high-risk target list" for the detected harmful substance and base materials, and transportation vehicles, distribution channel and production source associated with the detected harmful substance. The "high-risk target list" is stored in the database 2670 to allow the monitoring network system 2600 to more frequently monitor samples on the "high-risk target list" afterwards.

The level of urgency can be categorized by different risk levels such as green (safe), blue, yellow, orange, red (the most risky). The warning signal can include the current and/or anticipated position of the hazardous substance as well as the suspected exterior appearance for the carrier or the package for the hazardous substance. Appropriate personnel can be alerted. Security personnel can be dispatched to the location of the hazardous substance. An evacuation can be initiated.

If a harmful substance is not found in the samples of a product, the qualification system 2690 can qualify the sample as clear of harmful substances; the results can also be stored in the database 2670 for the record (step 2870).

In some embodiments, the location and time of the hazardous/harmful substance can be correlated by the positions of the sensors and the capture times for the detections of harmful substance. The location for a stationary hazardous material can be determined by interpolating the positions of the sensors. The locations and capture times of a moving sample containing the hazardous substance can be generate a moving path to predict the destination of the sample to allow it to be intercepted.

In some embodiments, the spectral data collected by the sensors can be used in conjunction with image data captured from the scene near the spectral sensors. For example, a digital or video camera 2760 positioned near the probe can take a picture of a suspected person or a package. The image of the suspected person or package can be stored and reported in association of the location of the hazardous substance to prepare for an appropriate response.

The above disclosed systems and methods have wide applications. In one example, a distribution center for meat, vegetables, fruits, and other food products can include a central office (as shown in FIG. 26) and multiple inspection personnel each carrying (or wearing) a mobile detector. The distribution center can include an analysis lab or can use the services of an analysis lab off site. The food products such as vegetables, dairy products, meat and vegetables can be shipped into the distribution center by big trucks (e.g. 20 ton trucks) from food manufacturing sites, vegetable, orchards, farms, dairy farms, ranches, etc. The inspection personnel can retrieve the identification of each food product, driver and vehicle information, and the source and destinations of the product. The inspection personnel can visually inspect the food product, and take samples of the incoming food products for spectral detection as the products are offloaded from the big trucks. The identification information and the spectral data are wirelessly transmitted instantaneously to the central office for spectral analysis. The data is stored in the database. The food products that pass the inspection will be qualified. The food products are then separated into small batches and loaded onto smaller trucks (e.g. 2 ton trucks) to be shipped to retail sites such as grocery stores, supermarkets, restaurants, and large retail stores such as Costco, Wal-Mart, or Target. The problematic products can be held for further analysis in the analysis in the lab. If harmful substance is confirmed, the food products can be stopped or destroyed. Since the identification information is stored, the source of the food is immediately known. Inspection personnel can be sent to the site that produced the food product, and alert messages can be sent to other distribution centers that may have received food products from the same source.

In another example, the disclosed monitoring system can be used to monitor and to prevent the spread of infectious diseases such as SARS in wide area. The disclosed monitoring system can be used to monitor pollutants in the environment, and to monitor chemical and biological agents for preventing and defending against terrorist attacks. For example, the disclosed monitoring system can be disposed in a water distribution system including reservoirs, canals, water treatment plants, and rivers. The disclosed monitoring system can be used to sense chemical changes in the environment for forecasting earthquakes or monitoring chemical changes for action taken after earthquakes.

In some embodiments, the probe 2621 in the mobile detector 2620 and the probe 2631 in the analytical lab 2630 can include other types of sensors. For example, the probe 2621, 2631 can include a chemical or biological immunoassay for detecting harmful biological and chemical substances. The biological immunoassay is configured to hold a plurality of antibodies which each is specifically configured to bind with a target antigen which may be part of or associated harmful biological and chemical substance. Likewise, the biological immunoassay can hold a plurality of antigens which each is specifically configured to bind with a target antibody which may be part of or associated harmful biological and chemical substance. The binding of a specific pair of antigen-antibody in the biological immunoassay can be detected by spectral analysis such as Raman spectroscopy as a positive identification of the harmful antigen or antibody substance. A spectral signature can indicate the binding of one of plurality of antibodies with the specific antigen.

Figure 29:
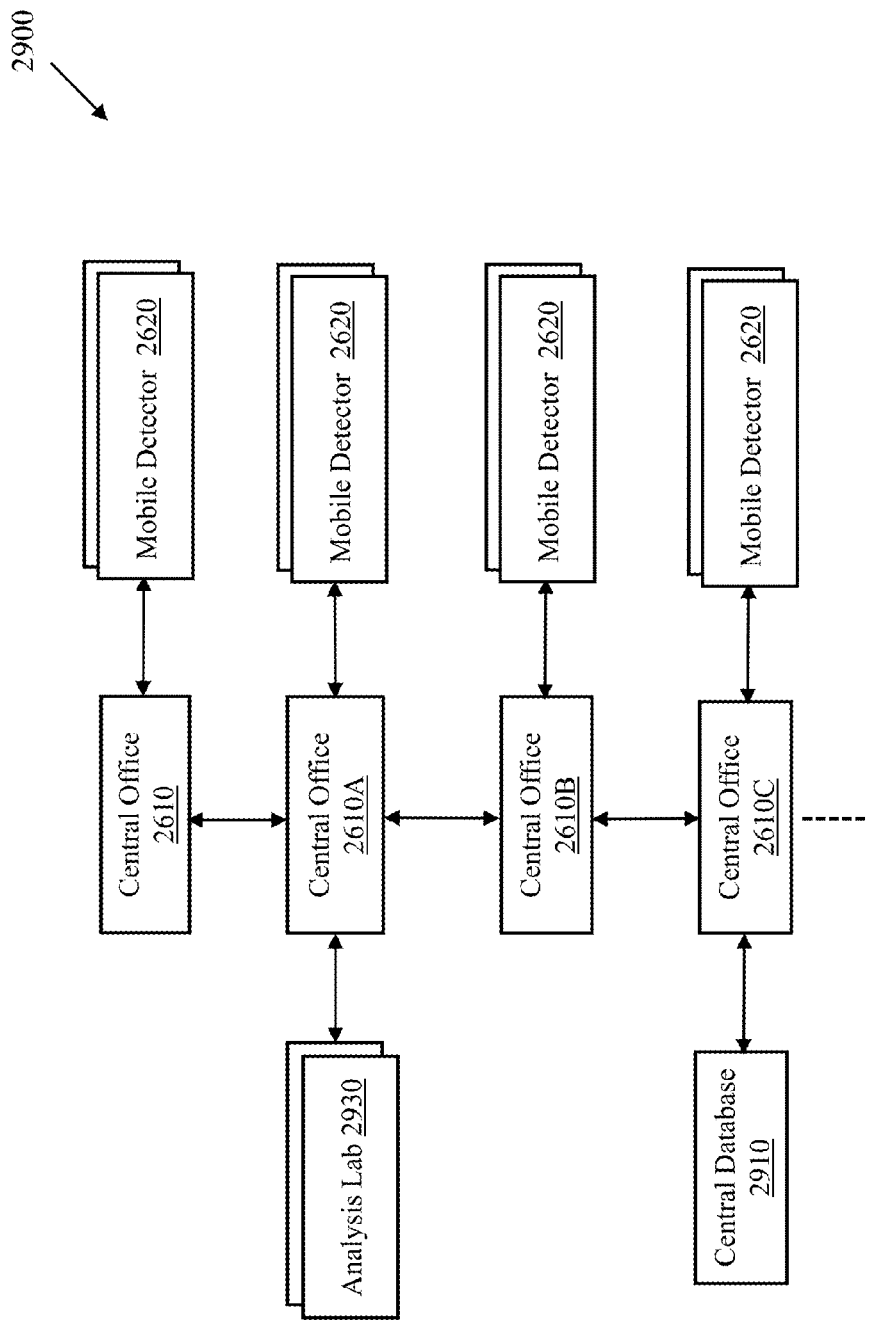
FIG. 29 is a block diagram of another exemplified monitoring network system in accordance to the present invention.

In another example, the probe 2621 in the mobile detector 2620 and the probe 2631 in the analytical lab 2630 can use enzyme inhibition method. Vegetables often include residuals of pesticides which may include organic phosphorus Inhibition of enzymes by the organic phosphorus can be detected by spectral analysis such as Raman spectroscopy. A spectral signature can indicate the inhibition of the enzyme by a harmful substance in the sample material, which is used as an indication to detect the residual pesticides in vegetables and fruits. In some embodiments, referring to FIG. 29, a monitoring network system 2900 can include a network of central offices 2600, 2600A, 2600B . . . , each in communication with mobile detectors 2620 or stationary detectors. The monitoring network system 2900 can include one or more analysis lab 2930 in wired or wireless communication with the central offices 2600, 2600A, 2600B . . . . The monitoring network system 2900 can include a central database to track inspection data from all central offices 2600, 2600A, 2600B . . . so that the data can be cross shared between the central offices which can cover a large region such as a a state, a province, a country, a district, a city, an inspection station or a mobile vehicle. The controllers and processors in the central offices 2600, 2600A, 2600B . . . can process data in a cloud computing model. The qualification and warning can be implemented in region wide. A region-wide alert and response system is in communication with the plurality of central offices. The alert and response system is configured to send out an alert signal about the sample material when the harmful substance is identified in the sample material in one or more of the central offices.

The monitoring network system 2900 can include different stages of inspections: the first stage inspection of harmful substances: using on-site and high throughput detection methods, such as Raman and surface-enhanced Raman methods, enzyme inhibition method, and chemical or biological immunoassay method, to screen high volume high distribution-rate goods (for example: food, drinks, water, drug raw materials, body fluid samples of human being or animals, etc.) in distribution channels, storage areas and logistics distribution centers. Small quantity of the samples (e.g. 0.1%-1% of the samples) can be sent to the analytical lab 2630. The analytical lab 2630 can have other lab equipment such as HPLC, GC-MS, IC, IMS, AAS, ICP-MS, etc., for additional analyses for confirming the existence of the harmful substance.

The monitoring network system 2900 can include different authorized levels: a first level at inspection point (test station or inspection mobile vehicle), a second level that connect inspection points at the first level by a network, a $3^{rd}$ level of city monitoring and control center, a $4^{th}$ level of county monitoring and control center, a $5^{th}$ level of the province/state monitoring and control center, and a $6^{th}$ level of central government monitoring and control center. The monitoring network system 2900 can track the detected harmful substance back to its distribution channels and production sources, so that event monitoring and control center is able to find impact channels and areas as function of time, in order to take immediate action to minimize impact from the event.

Detecting Crude Oil or Gas Content in Drilling Samples Using Nano Surface-Enhanced Raman Spectroscopic Analysis Method The increased energy consumption requires low cost, effective and efficient ways to explore crude oil and gas under the ground. The current conventional analysis methods based on X-Ray and gas chromatography are usually conducted in the labs and have long turn-around times. The present application discloses Raman spectral analyses methods for detecting crude oil and gas in drilling samples extracted from wells. The disclosed methods are at least as accurate as conventional methods, and can be conveniently implemented in the field with significantly reduced measurement cycle times. The disclosed systems also have lower cost than conventional measurement systems.

To detect potential crude oil or gas underground involves drilling a deep hole (e.g. in about 10 cm diameter) into the ground with a drill bit, and extracting a drilling sample (i.e. drilling record) that is typically in the form of a fluid or a piece of rock. For example, a drilling sample can contain a mixture of brine (e.g. about 50%, or 80%), clay and polymers (e.g. about 5%), mineral particles (e.g. about 10% or 20%), and other substances (e.g. about 5%). Once a sample out above ground, the drilling sample fluid is poured into a container, e.g., a bottle, which is subsequently sealed and shipped to a lab for testing. The drilling and pressure in the drilling process deep underground create a lot of heat, which can raise the drilling fluid to 50° C.-80° C., vaporizing much of the low molecular weight substances in the drilling fluid before they arrive at ground surface for testing. Since many low-molecular weight substances in gas and crude oil have vaporization temperatures below 100° C. or even below 20° C., the conventional crude oil/gas detection methods often do not have sufficient signal strengths for low-molecular weight crude oil/gas substances which is consistent with a sample underground (e.g., 3000 m deep underground).

Figure 30:
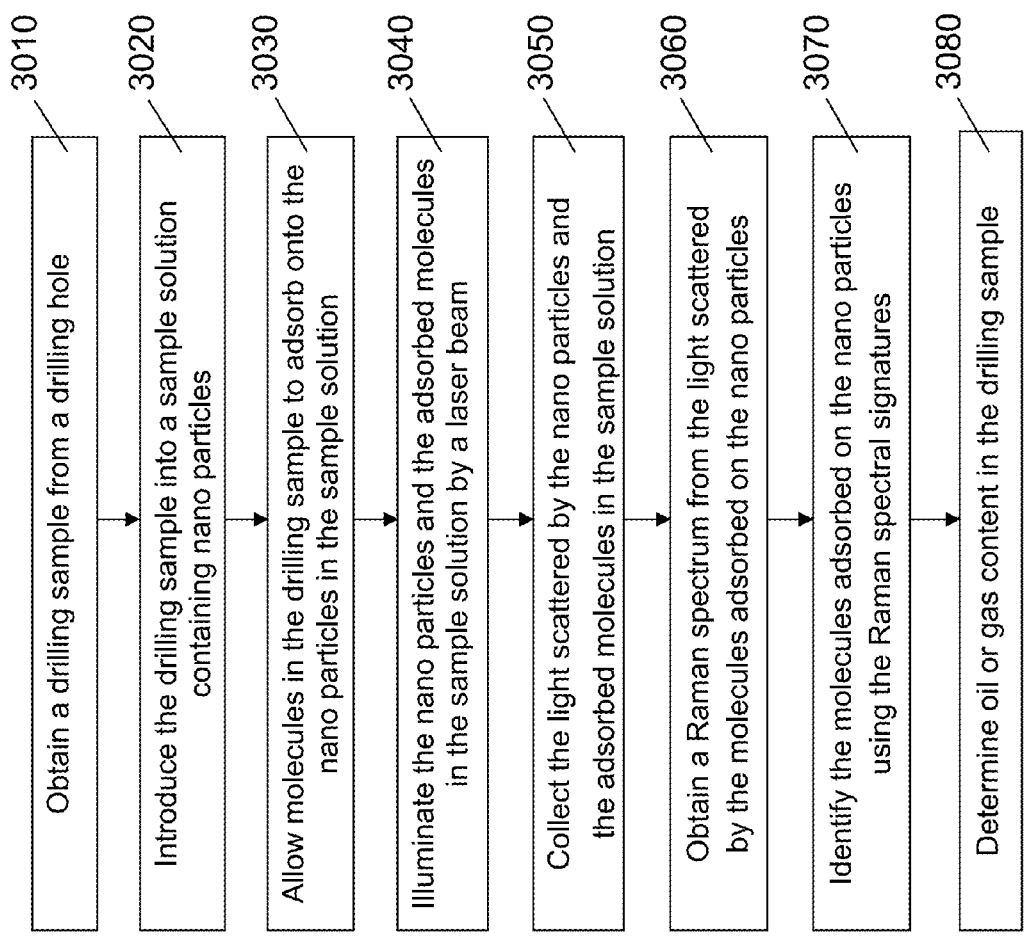
FIG. 30 illustrates an exemplified process for determining potential oil content in drilling fluid.
Figure 31:
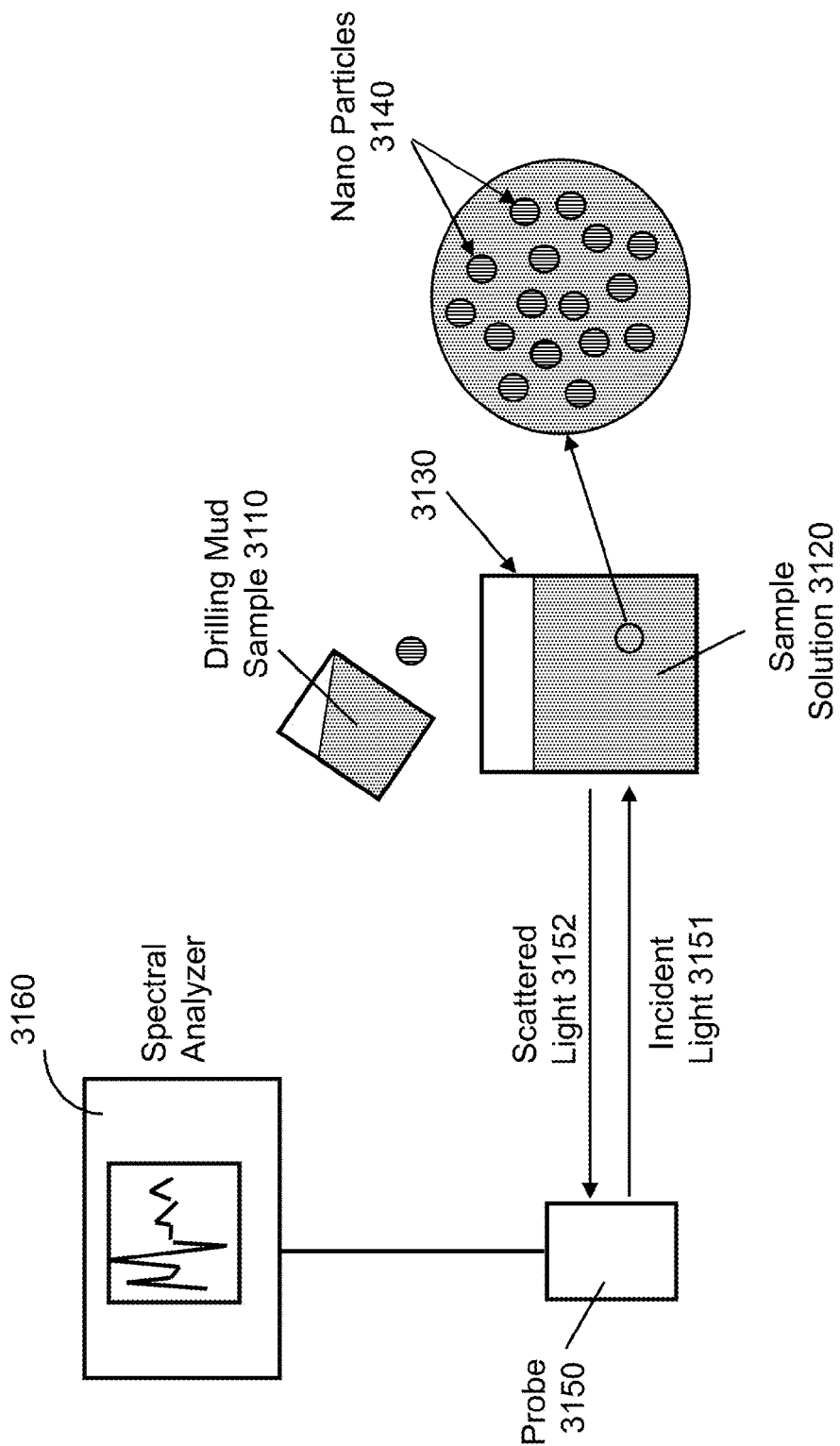
FIG. 31 is a schematic diagram showing a configuration for detecting chemical substance in a drilling sample using a test reagent or a nano chip containing nano particles and a light scattering probe.

In some embodiments, referring to FIGS. 30 and 31, a drilling sample 3110 is extracted from a drilling hole (or well) in the field (step 3010). An example of an important signature chemical substance for crude oil in a drilling sample is an aromatic compound, e.g., thiophene group including thiophene, dibenzothiophene (DBT) and its homologue molecules.

In some embodiments, referring to FIGS. 30 and 31, a drilling sample 3110 is extracted from a drilling hole (or well) in the field (step 3010). An example of an important signature chemical substance for crude oil in a drilling sample is an aromatic compound, e.g., phenanthrene group including phenanthrene, methylphenanthrene and its homologue molecules.

In some embodiments, a drilling sample 3110 is extracted from a drilling hole (or well) in the field (step 3010). An example of an important signature chemical substance for crude oil in a drilling sample is an aromatic compound, e.g., carbazole group including carbazole and its homologue molecules.

The vapor pressure of thiophene, dibenzothiophene, phenanthrene, methyl phenanthrene, carbazole, and their respective homologue compound molecules is above 200° C., or 300° C.

The drilling sample 3110 is introduced into a sample solution test reagent 3120 comprising nano particles 3140 in a container 3130 (step 3020). The container 3130 can be an optical vial, a beaker, or a transparent test tube, etc. The nano particles 3140 can exist in the form of a colloidal suspension in the sample solution 3120. The nano particles 3140 can be in different shapes and can include carbon nano tubes. A drilling sample 3110 is prepared in chemical and physical ways including but not limited to sample purification, extraction, separation, then is mixed and/or dissolved in the sample solution 3120 to allow molecules in the drilling sample 3110 to adsorb on surfaces of the nano particles 3140 (step 3030).

Figure 32:
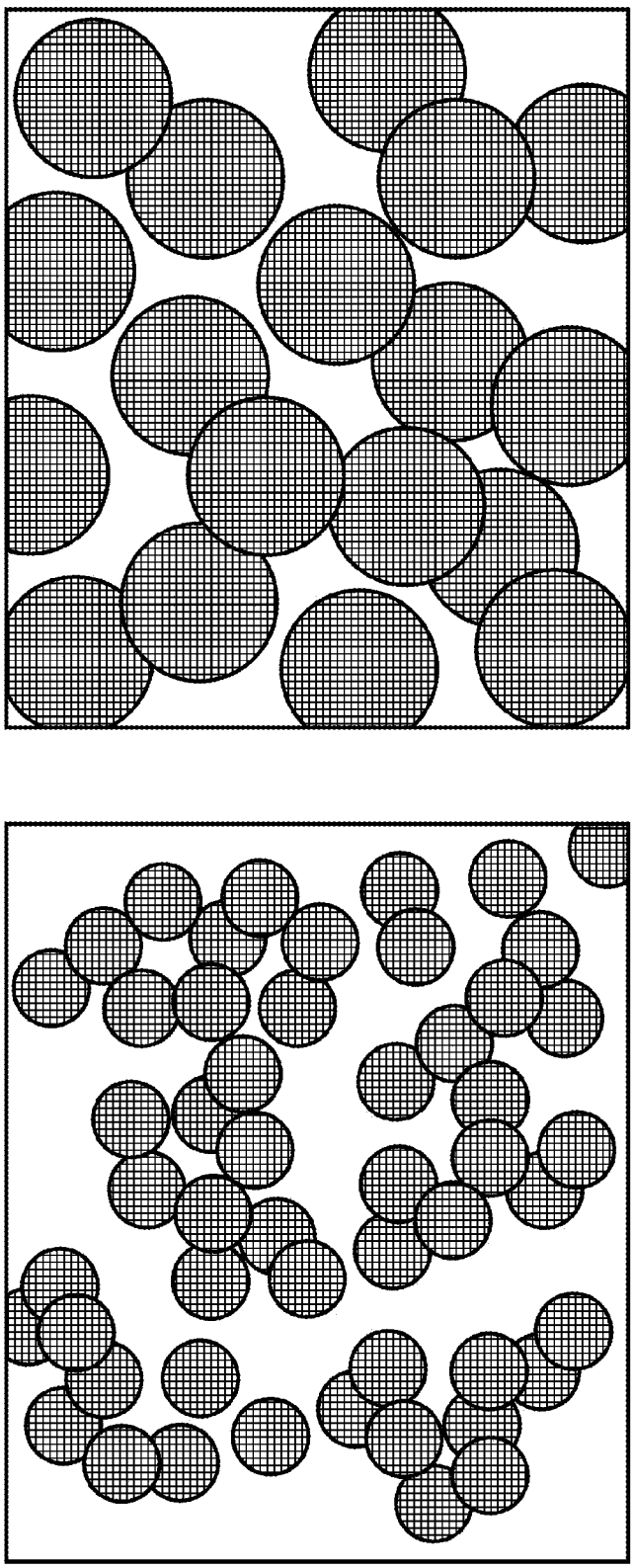
FIG. 32 show exemplified micrographs of the nano particles shown in FIG. 31 using scanning electron microscope.
Figure 33:
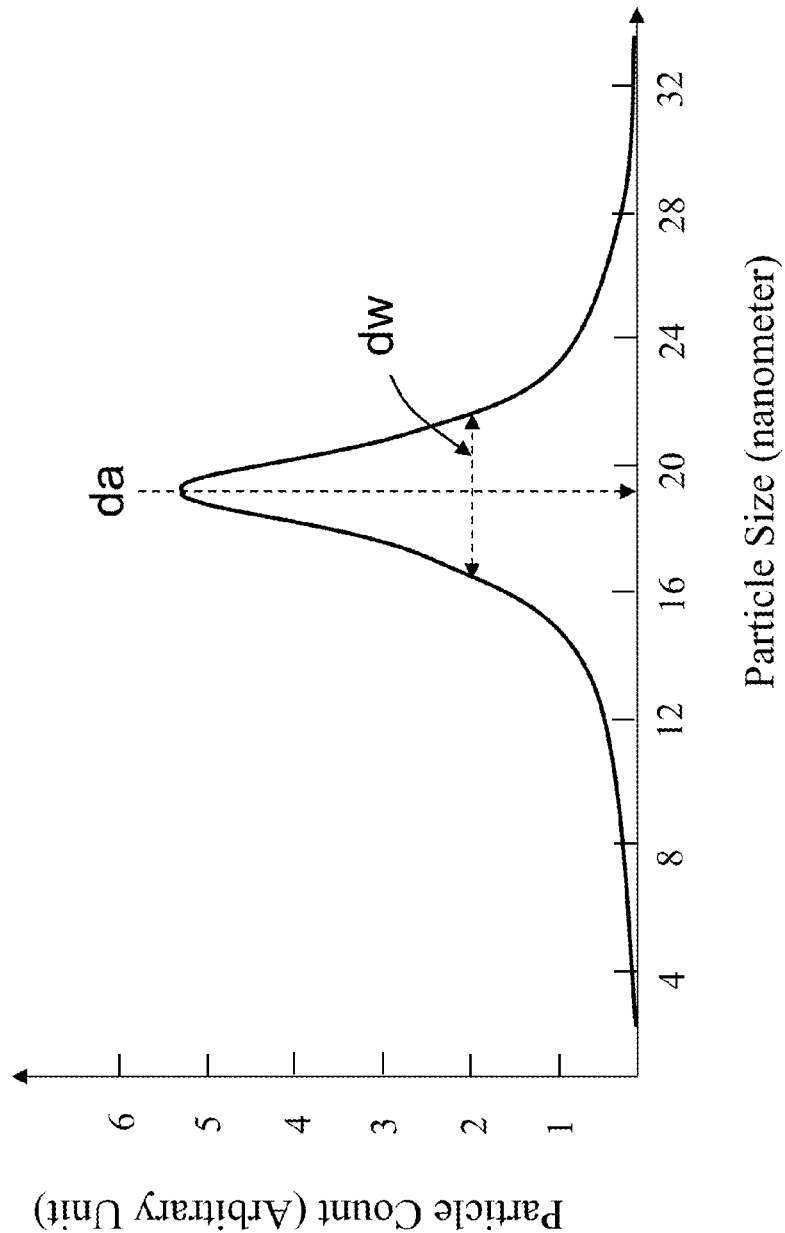
FIG. 33 illustrates an exemplified size distribution of the nano particles in the sample solution shown in FIG. 31.

The nano particles 3140 can exist in round or irregular shapes. The nano particles 3140, as shown in FIG. 32, can be individually separated, or aggregated in clusters, in the sample solution 3120. The nano particles 3140 can have a size distribution, as shown in FIG. 33, which is characterized by an average particle dimension $d_a$ and a particle-dimension distribution width $d_w$. The ratio $d_w/d_a$ can range from about 0.01 to about 3, which defines a quite monodispersed distribution to a polydispersed particle distribution. The ratio $d_w/d_a$ can often range from about 0.03 to about 1. The average particle dimension $d_a$ can range from about 1 nm to about 10,000 nm, or from 2 nm to 500 nm.

The nano particles 3140 can be formed by materials that can be select to enhance Raman spectral signals from the molecules adsorbed on the nano particles 3140. For example, suitable materials for the nano particles 3140 include metallic materials such as Al, Ag, Au, Cu, Fe, Co, Ni, Cr, Zn, Sn, Pd, Pt, and their alloys, oxide materials such as titanium oxide, silicon oxide, and zinc oxide, tin oxide, silicon, silicon oxide, and polymeric materials. The nano particles 3140 can also include polymers tethered to the particle surfaces to help repel each other in the sample solution 3120. The magnetic or ferromagnetic materials (e.g. Fe, Co, Ni, or Fe, Co, Ni containing compounds, or their alloys) can enhance the Raman spectral signal when the sample solution 3120 is applied with a static or alternating electrical, magnetic, or electro-magnetic field.

In some embodiments, the sample solution 3120 can include a mixture of nano particles of different material compositions. For example, the nano particles can include a mixture of silicon and metallic nano particles, or a mixture of silicon and polymeric nano particles, or a mixture of silicon, metallic, metallic oxide, and polymeric nano particles. Raman signal intensity can be enhanced by optimizing mixture compositions.

In some embodiments, the nano particles 3140 are charged and repel each other in the sample solution 3120, which helps to separate the nano particles 3140 and the formation of a colloidal suspension. The solvent in the sample solution 3120 can be arranged to enhance Raman spectral signal intensity from molecules adsorbed on the nano particles 3140. It was found that ions and especially multi-valence ions can significantly enhance the signal intensity of the Raman signal. An ionic material can thus be added to the sample solution 3120. Examples of ions that the ionic material carries to the sample solution 3120 can include $Na^+$, $K^+$, $Li^+$, $Ca^{++}$, $Ba^{++}$, $Sr^{++}$, $Mg^{++}$, $Mn^{++}$, $Al^{+++}$, $Zn^{++}$, $Sn^{++}$, $Sn^{++++}$, $F^-$, $Cl^-$, $Br^-$, and $I^-$, and so on. The ions can have mono charge, or preferably have double or high charges in the sample solution 3120. The ions can have positive or negative charges. The sample solution 3120 can have an ionic compound, including but not limited to LiF, NaF, NaCl, KCl, KI, etc. Suitable ionic concentration can range from 10 μM to saturated level.

In some embodiments, the nano particles 3140 can include carbon nano tubes with diameters ranging from 0.3 nm to 100 nm. The lengths of the carbon nano tubes can be from 5 nm to multiple millimeters. The length-to-diameter ratio of the carbon nano tubes can be as high as 50 million. The carbon nano tubes can have single-walls, or multiple walls. The carbon nano tubes can be in the form of Fullerite, a torus, nanobuds, and nanoflowers.

A probe 3150 includes an optical transmitter (e.g. a laser device, not shown) and an optical detector (not shown). The optical transmitter emits an incident light 3151 (e. g. a laser beam) to illuminate the nano particles 3140 and the molecules adsorbed on the nano particles 3140 in the sample solution 3120 (step 3040). Scattered lights 3152 from the nano particles 3140 and the adsorbed molecules are collected by the optical detector in the probe 3150 (step 3050). The output signal from the probe 3150 is analyzed by a spectral analyzer 3160.

Optionally, when the nano particles 3140 are made of magnetic materials, an electrical field, a magnetic field, or an electro-magnetic field is applied to the sample solution 3120 when the scattered light collected.

An important aspect of the presently disclosed method is that the steps of illuminating the sample solution and collecting light scattered by the drilling sample can be conducted in the field, that is, in the vicinity of the drilling hole to carry out on-site test. There is no need to ship the drilling sample to a central lab location. Thus testing cycle time is saved in the presently disclosed method not only in the measurements themselves but also in the eliminating the time spent on shipping the drilling samples.

Figure 34:
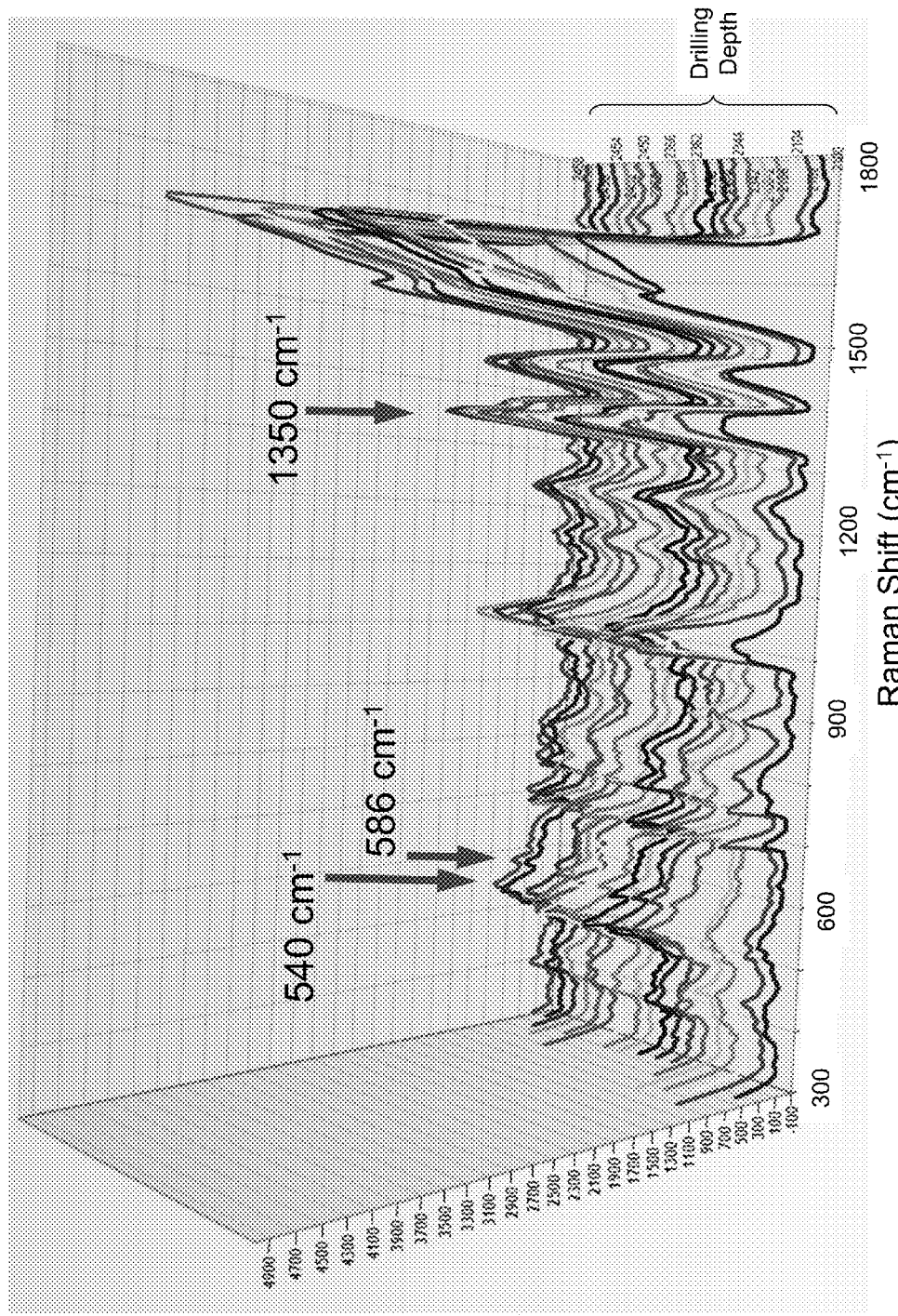
FIG. 34 illustrates exemplified nano-enhanced Raman spectra obtained from drilling mud samples extracted at different depths of a drilling hole.

A Raman spectrum of the molecules adsorbed on the nano particles 3140 is obtained from the scattered light (step 3060). For example, as shown in FIG. 34, nano-surface-enhanced Raman spectra (or nano-enhanced Raman spectra) are obtained from drilling samples extracted at different depths (2100 meters to 2458 meters) of a drilling hole. The spectra corresponding to different drilling-hole depths show several Raman spectral peaks about 540 $cm^{-1}$, 586 $cm^{-1}$, and 1350 $cm^{-1}$.

Spectral signature(s) in the Raman spectrum can be used to identify the molecules adsorbed on the nano particles (step 3070). The concentration of the substance associated with the spectral signature in the drilling sample can be calculated using the spectral signature. For example, the height of a spectral peak, or the area under a spectral peak, or a signal-to-noise (i.e. peak to background noise) ratio can be calculated to calculate the concentration of the substance in the drilling sample. Since crude oil or gas is known to contain the substance, crude oil or gas content in the drilling sample can be qualitatively and quantitatively determined (step 3080). Steps 3070-3080 can be conducted by a local spectral analyzer 3160, or remotely in a central office that in communications with the probe 3150 as discussed below.

Figure 35A:
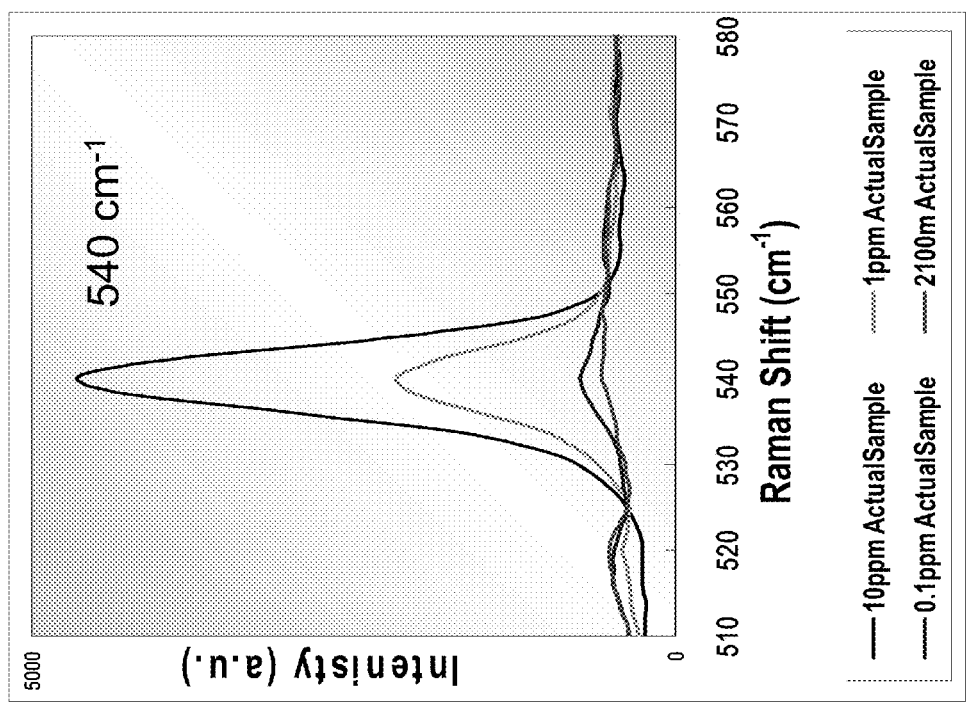
FIGS. 35A-35C illustrate Raman spectral signatures for methyl dibenzothiophenes (MDBTs) at different concentrations which are used to identify MDBTs in drilling mud samples.
Figure 35B:
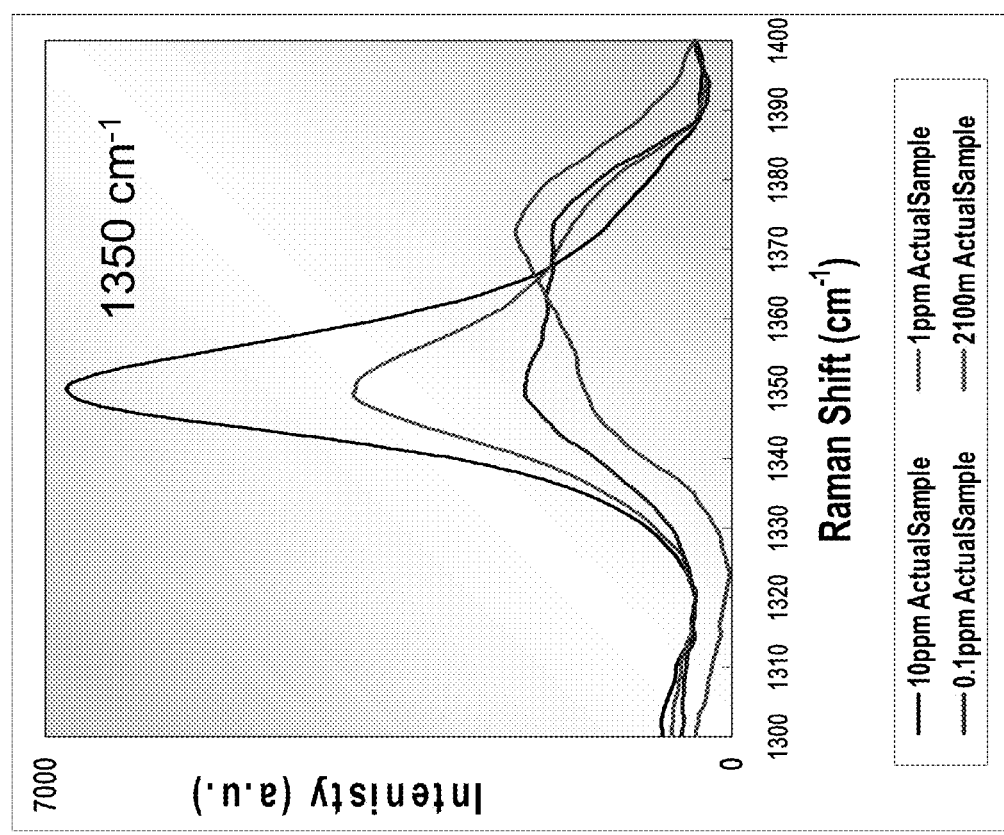
Figure 35C:
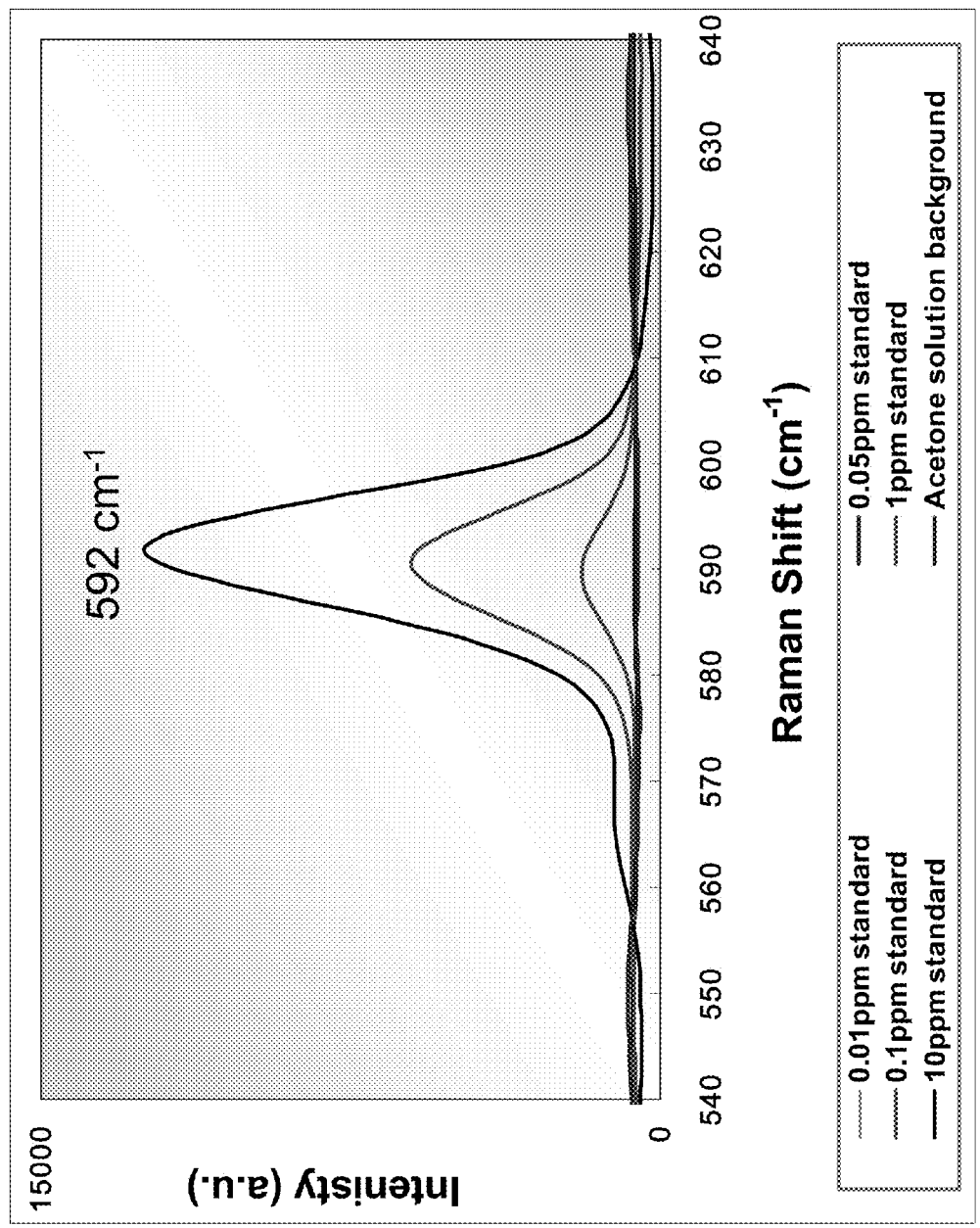

FIGS. 35A-35B illustrate reference Raman spectra of methylphenanthrene, one of homologue of phenanthrene, in a concentrations range from 0.01 ppm to 10 ppm. The reference Raman spectra show Raman spectral signatures about 540 $cm^{-1}$ and 1350 $cm^{-1}$. FIG. 35C illustrates reference Raman spectra of 4-6 methyl dibenzothiophenes (MDBTs), one of homologue of dibenzothiophene (DBT), in concentrations ranging from 0.01 ppm to 10 ppm. The reference Raman spectra show Raman spectral signatures about 592 $cm^{-1}$. These spectral signatures can be used to analyze nano-surface-enhanced Raman spectra obtained from drilling samples obtained from different depths underground (from 2100 meter to 2458 meter deep), as shown in FIG. 34, which identifies content dibenzothiophene's family member(s) in the drilling samples. The existence of dienzothiophene family member(s) in the drilling sample serves as an indicator for the probability of crude oil and gas underground. Other molecules that can provide Raman spectral signatures for detecting oil and gas content in drilling samples include aromatic molecules and multi-ring aromatic molecules such as thiophene, dibenzothiophene, methyl dibenzothiophene, 4,6 methyl dibenzothiophene, methylphenanthrene, and carbazole and their homologue compound molecules, respectively. Other molecules suitable for n-Hexane, Cyclohexane, Benzene, Toluene, Xylene (including m-Xylene, o-Xylene, and p-Xylene), Octane, Heptane, Noname, and other hydrocarbon compounds such as sulfur or nitrogen containing hydrocarbon compounds such as carbazole and its homologue compound molecules, and dibenzothiophene and its homologue compound molecules.

In some embodiments, since nano-surface enhanced Raman spectral analysis is highly sensitive, the presently disclosed method is capable of detecting substances that are partially evaporated in the drilling samples (during the drilling, or after the drilling sample is obtained but before the measurement). In other words, the presently disclosed method is especially advantageous for hydrocarbon molecules that have low boiling or vaporization temperatures, which are often rich in the content of crude oil or gas. For example, the substance associated with the Raman spectral signature(s) suitable for the present method can be a hydrocarbon compound that has a boiling temperature or a vaporization temperature below 100° C., which are difficult, as described above, for the conventional methods to detect due to loss of evaporation materials during drilling and material handling and transfer from drilling well to the lab.

The presently disclosed method of identifying molecules using nano-surface-enhanced Raman spectra has been compared to conventional testing method such as gas chromatography (GC). Close correlation was found between the presently disclosed method and GC testing techniques. However, the presently disclosed method only took 20 minutes in the field at the location of the drilling hole, whereas the conventional GC method took over 4 hours, or even over 15 hours, to complete.

Determining Mineral Compositions in Rock Samples to Predict Probability of Crude Oil or Gas Underground In some embodiments, Raman spectral analysis can be used to determine mineral composition and distribution on rock samples extracted from underground in crude oil and gas exploration.

Figure 36:
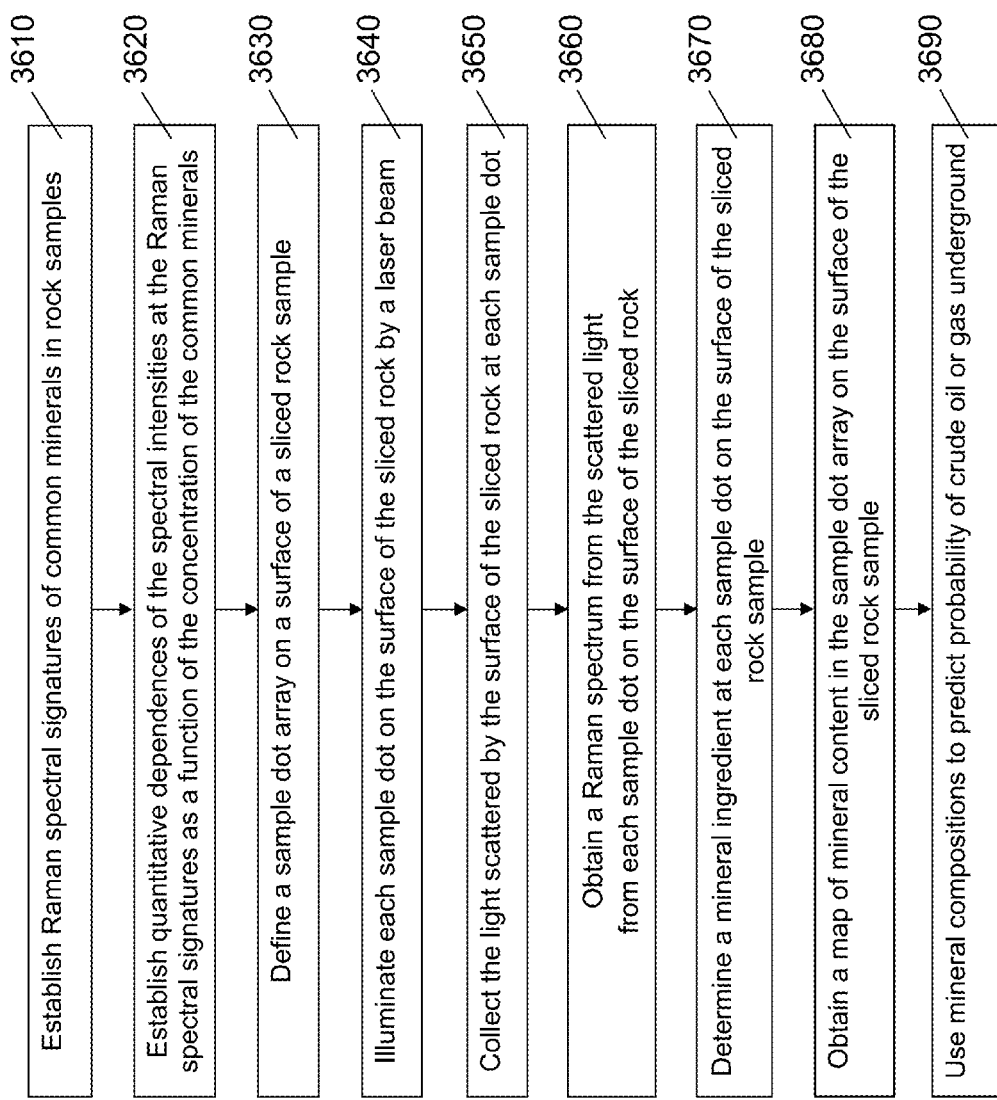
FIG. 36 illustrates an exemplified process for detecting mineral compositions in rock samples to determine probability of crude oil or gas underground.
Figure 37A:
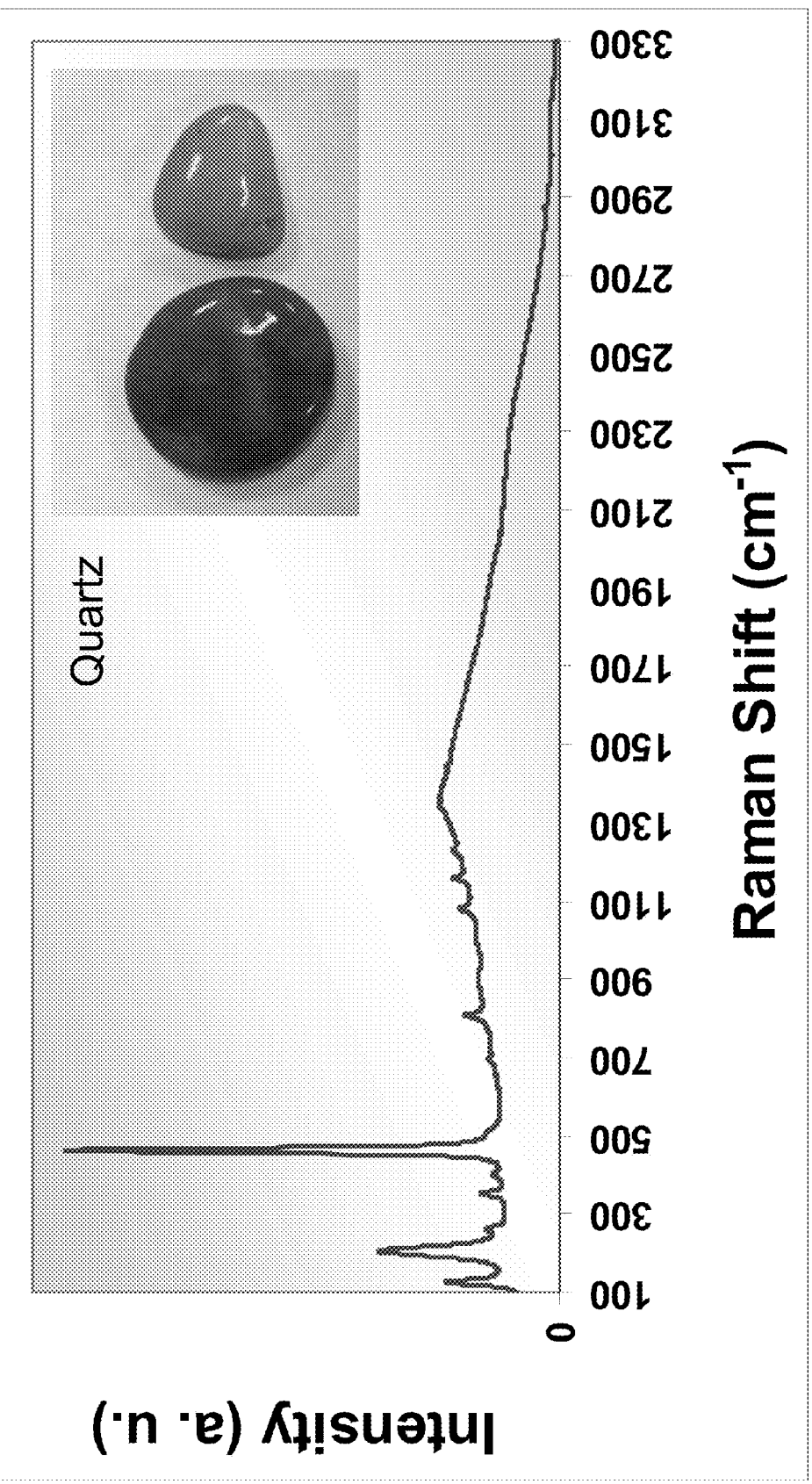
FIGS. 37A-37E illustrate Raman spectra and spectral signatures of several common minerals in rock samples.
Figure 37B:
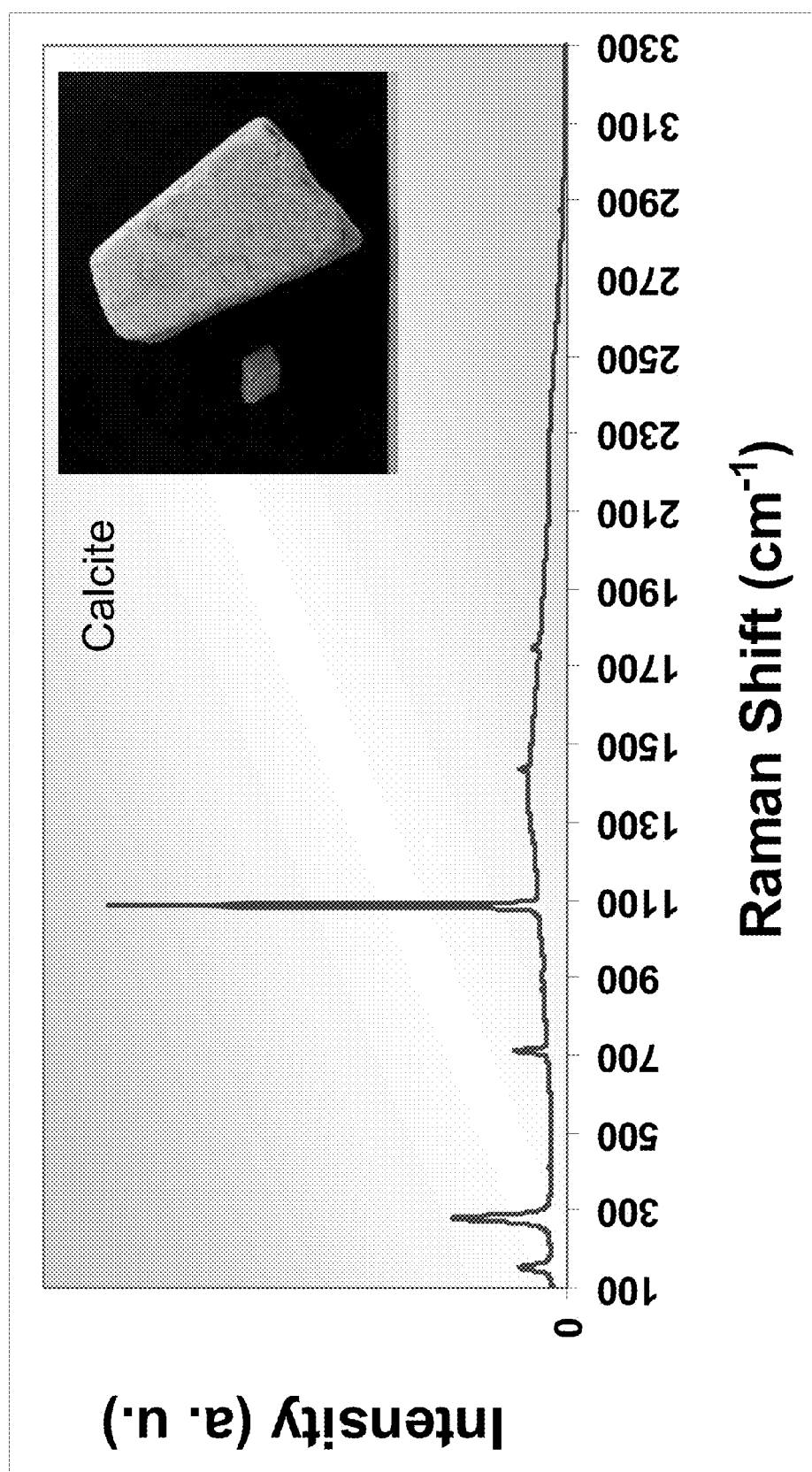
Figure 37C:
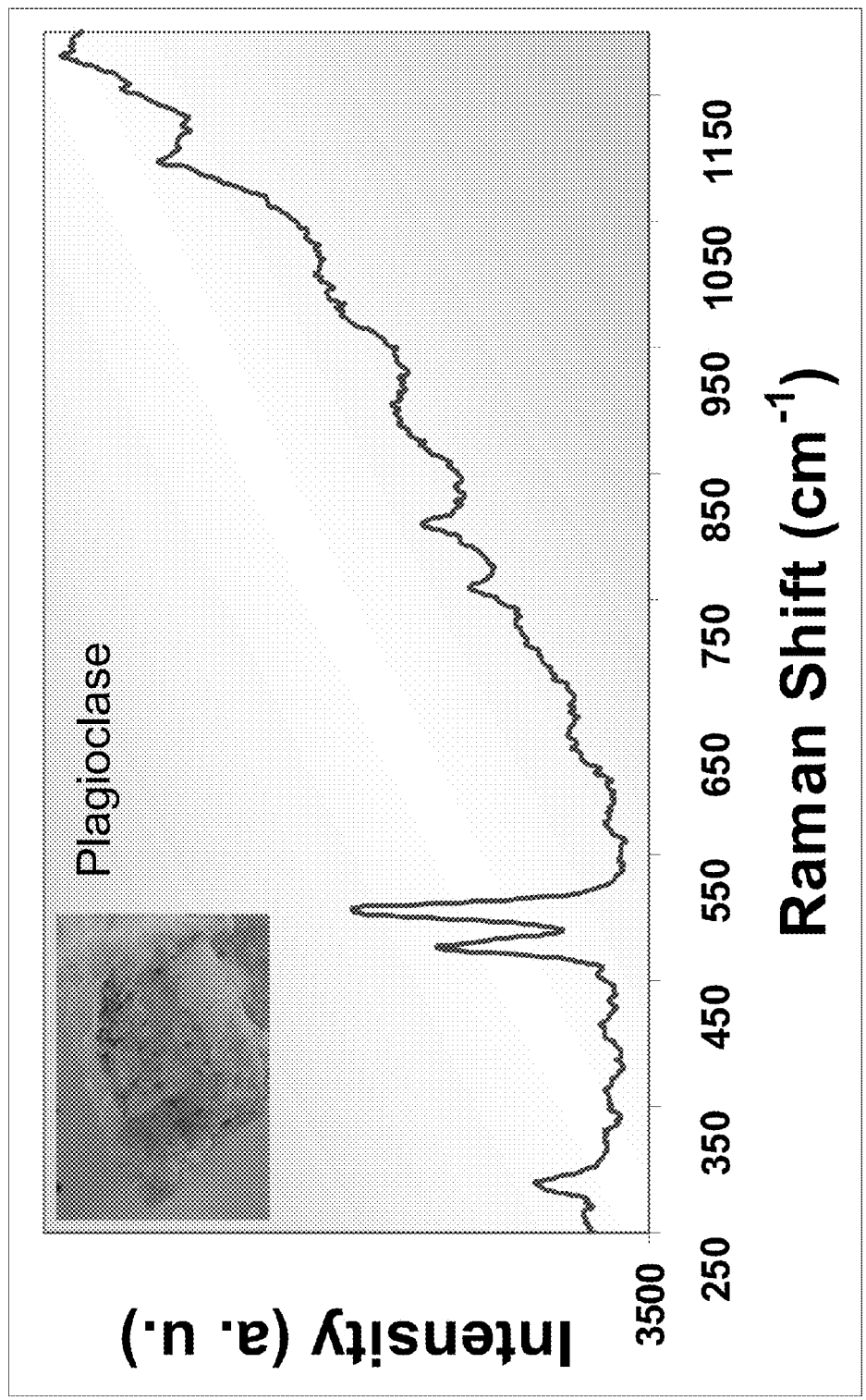
Figure 37D:
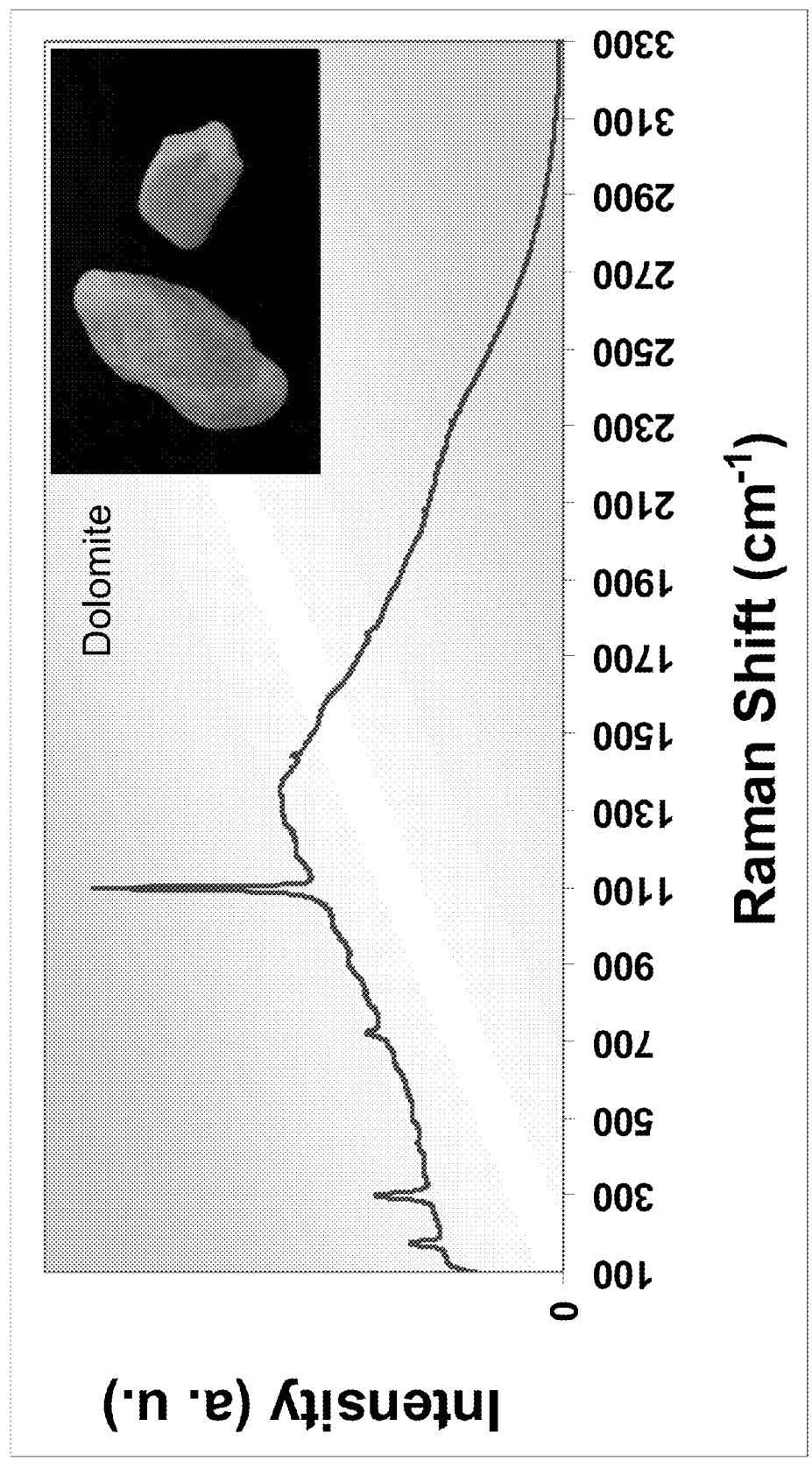
Figure 37E:
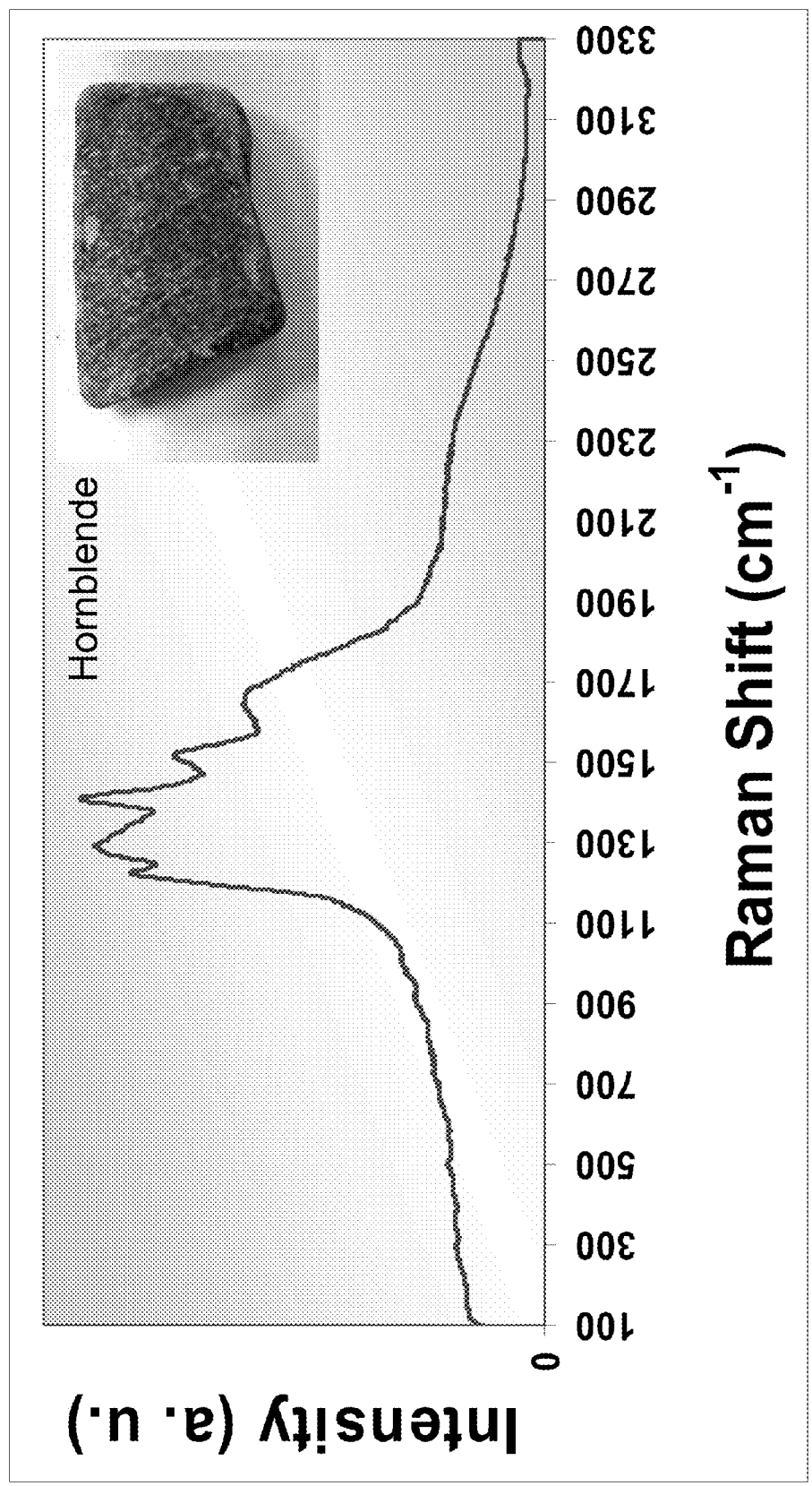

FIG. 36 illustrates an exemplified process for detecting mineral compositions in rock samples to determine probability of crude oil or gas underground. First, Raman spectral signatures of common minerals in rock samples are established (step 3610). FIGS. 37A-37E illustrate Raman spectra, respectively, associated with several common minerals: Quartz, Calcite, Plagioclase, Dolomite, and Hornblende. As shown, each of the Raman spectra includes one or more spectral signatures (Raman spectral peaks) at specific Raman shift in wavenumber.

Figure 38A:
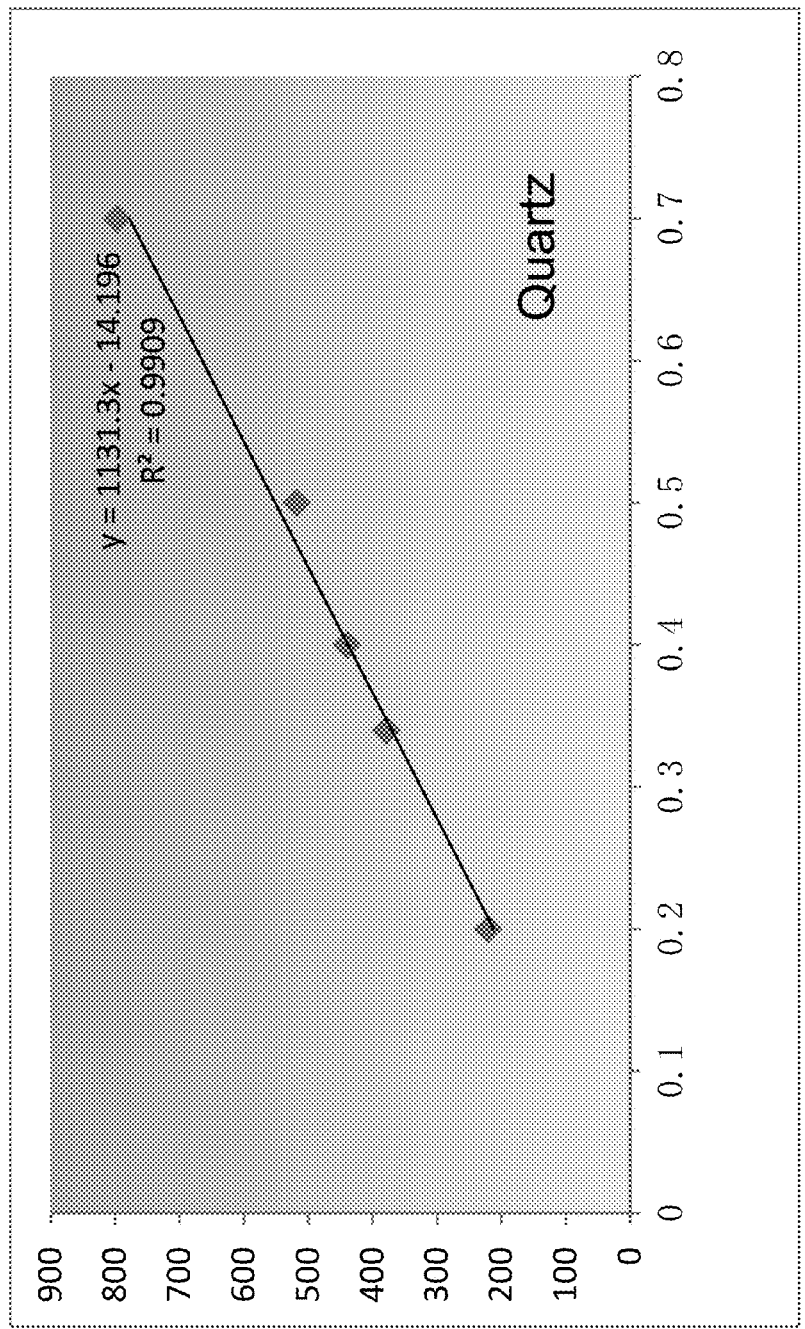
FIGS. 38A-38C illustrate Raman spectral intensities at the spectral signatures as a function of concentration for several common minerals in rock samples.
Figure 38B:
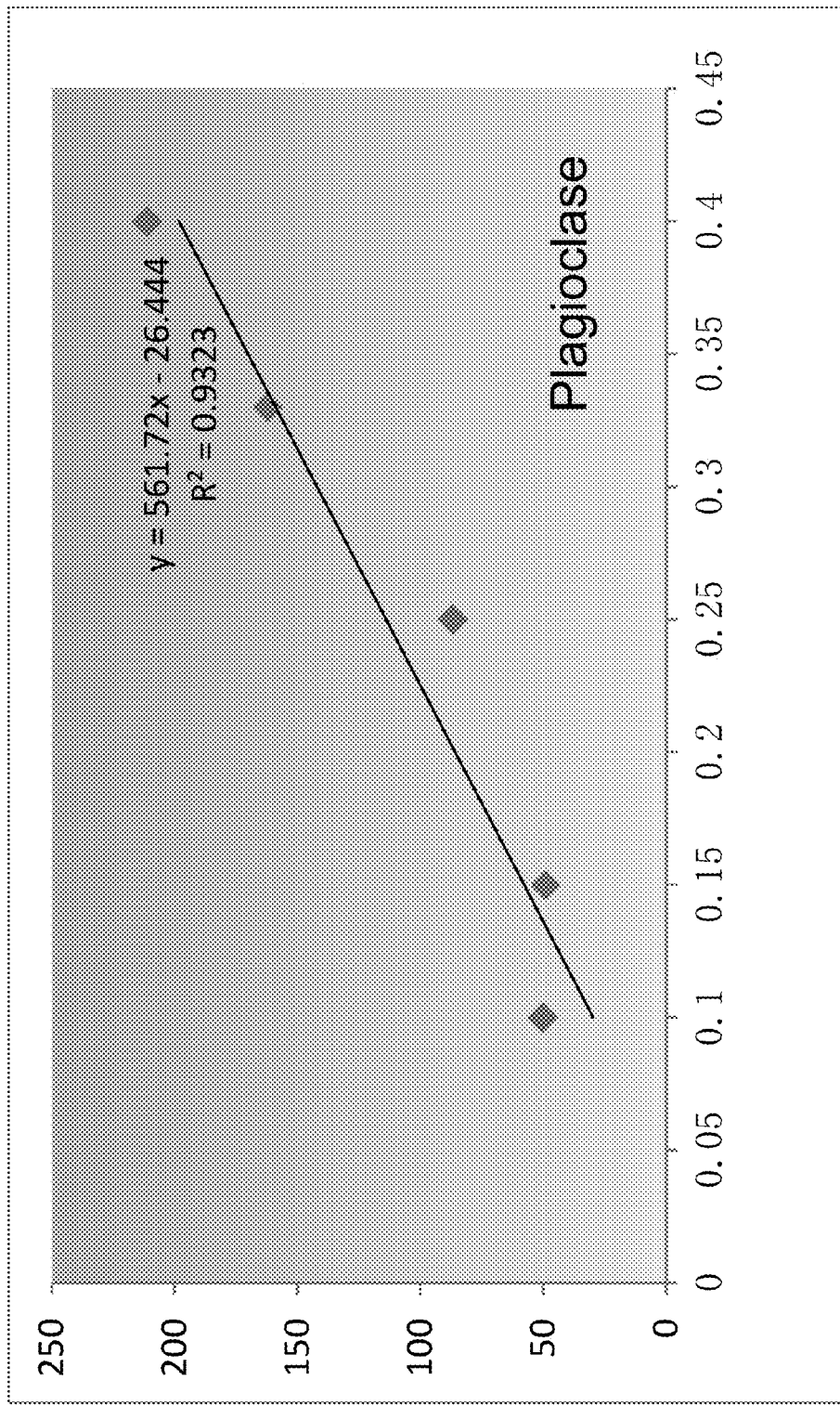
Figure 38C:
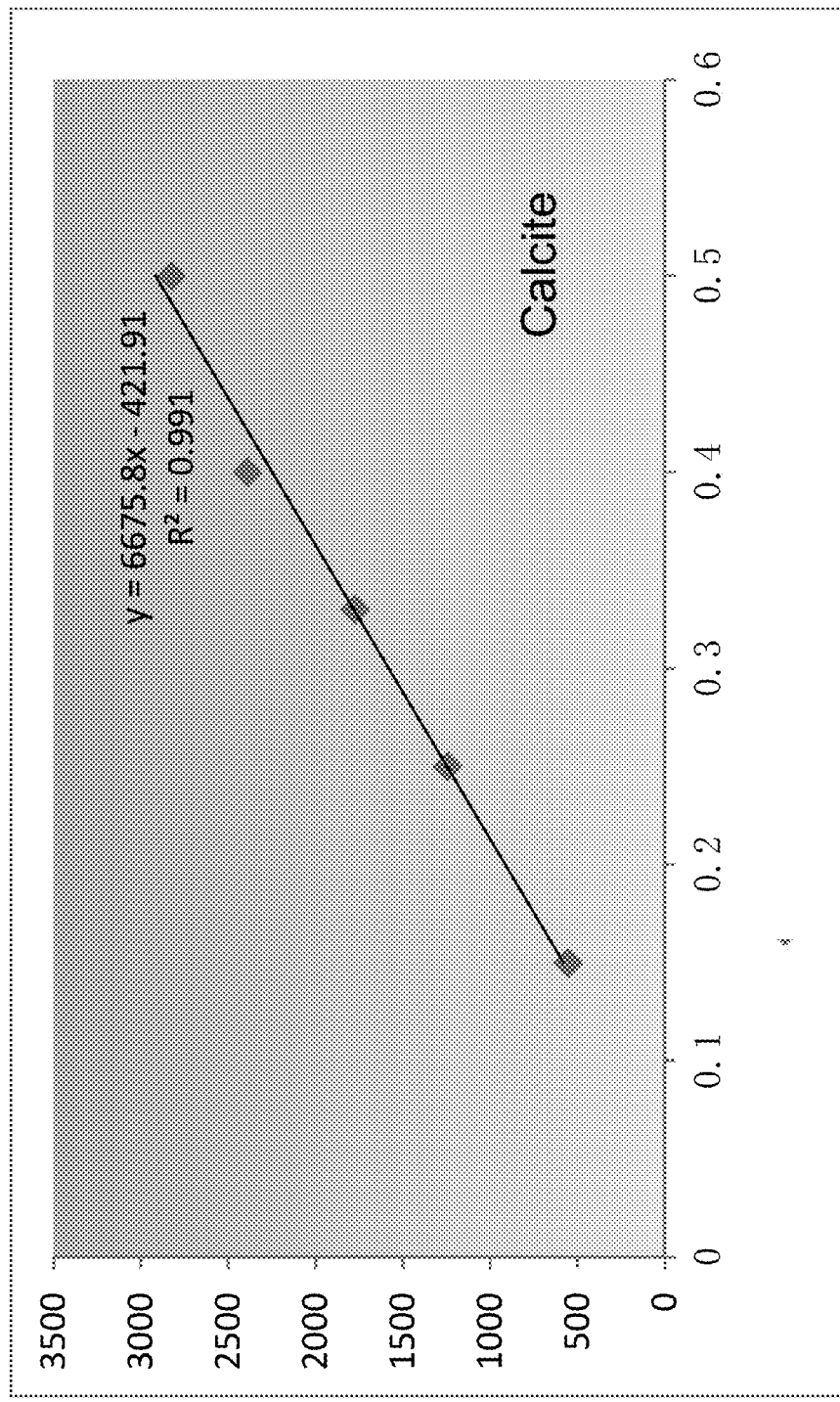

Next, quantitative dependences of the spectral intensities at the Raman spectral signatures are established as a function of the concentration of the common minerals (step 3620). FIGS. 38A-38C show experimentally obtained Raman spectral intensities at the spectral signatures as a function of concentration for Quartz, Plagioclase, and Calcite, which are common in rock samples.

A sliced rack sample (FIG. 39) is obtained by slicing a rock core sample obtained from underground. As shown in FIGS. 40A and 40B, sample dot arrays are respectively defined on the top and the bottom surfaces of the sliced rock sample (step 3630).

Similar to steps 3040-3060 in FIG. 30 (except that no sample solution of nano particles is involved here), each sample dot on the surface of the sliced rock is illuminated by a laser beam (step 3640). The light scattered by the surface of the sliced rock at each sample dot is collected (step 3650). A Raman spectrum is obtained collected the scattered light from each sample dot on the surface of the sliced rock (step 3660).

A main mineral ingredient is determined at each sample dot on the surface of the sliced rock sample (step 3670) using the Raman spectral signatures at specific Raman shift wavenumbers to identify mineral type. Concentration of each main mineral type at each sample dot can be obtained using the Raman spectral intensity at the Raman spectral signature using the functional relationships as exemplified in FIGS. 38A-38C. As shown in FIGS. 40A and 40B, a map of different types of mineral content (as well as each main mineral's concentration) is obtained across the sample dot array on the top and bottom surfaces of the sliced rock sample (step 3680). The exemplified minerals include Quartz, Calcite, Plagioclase, Dolomite, Pyroxene, Chlorite, Kalifeldspar, Na-feldspar, Amphibole, MuscLaumontite, analcime ovite, Biotite, Ankerite, Siderite, Anhydrite, Gypsum, Thenardite, Barite, Pyrite, Glauberite, Laumontite, Analcime, Illite, Smectite, Kaolinite, Corundum, Ankerite, or Halite. Other minerals suitable for the presently disclosed method include Mica, Hornblende, and Granite.

Figure 39:
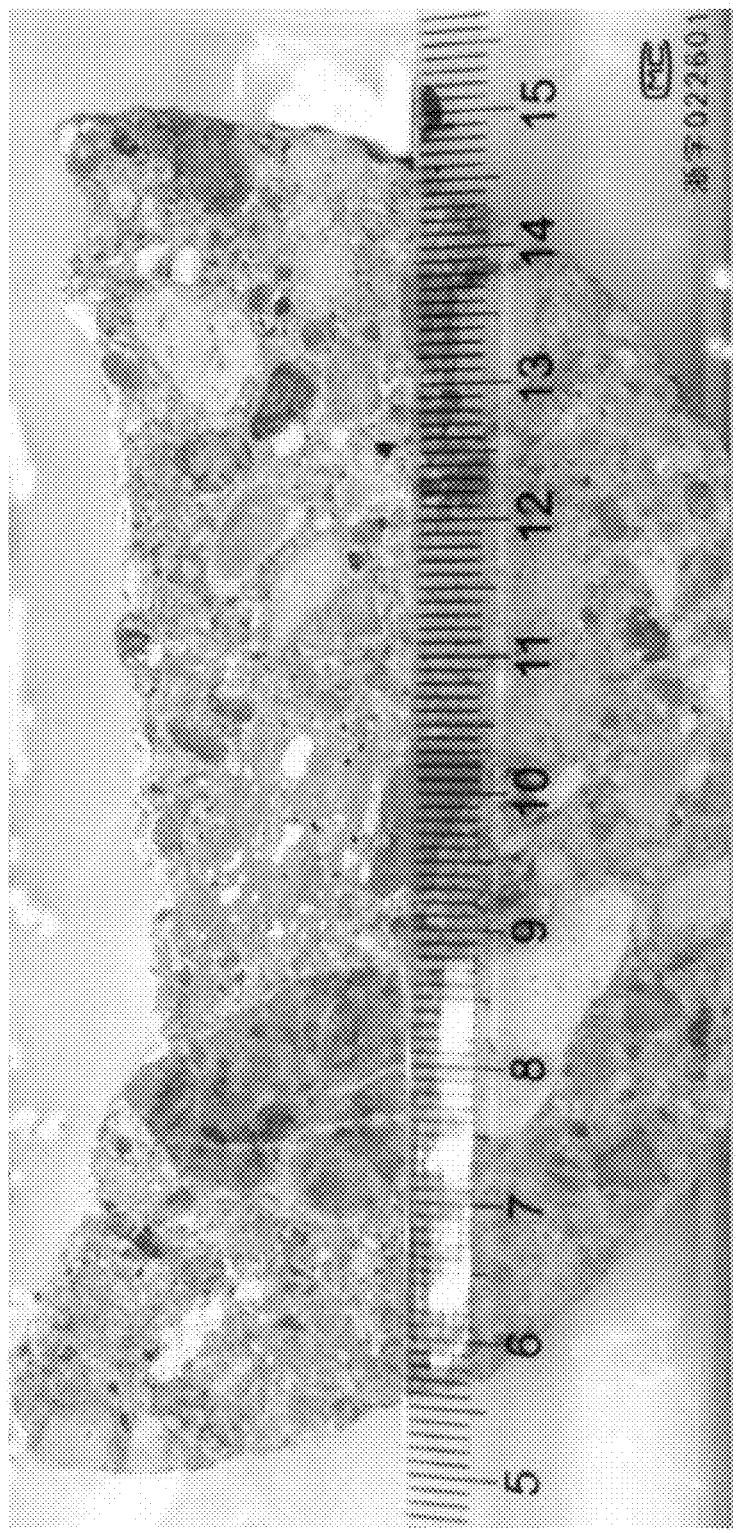
FIG. 39 shows an example of a sliced rock sample.
Figure 40A:
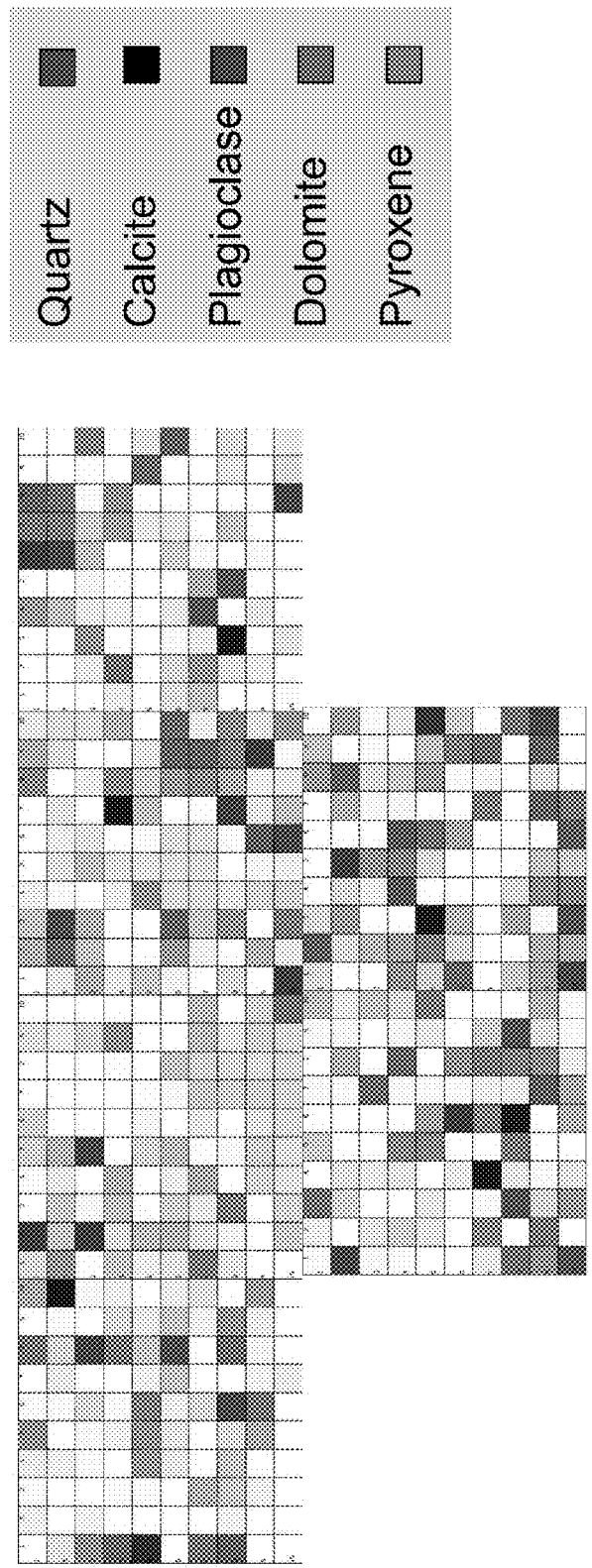
FIGS. 40A and 40B respectively show Raman mapping (or sampling dot arrays) on the two surfaces of the sliced rock sample in FIG. 39 and results of Raman spectral analyses at the sampling dots.
Figure 40B:
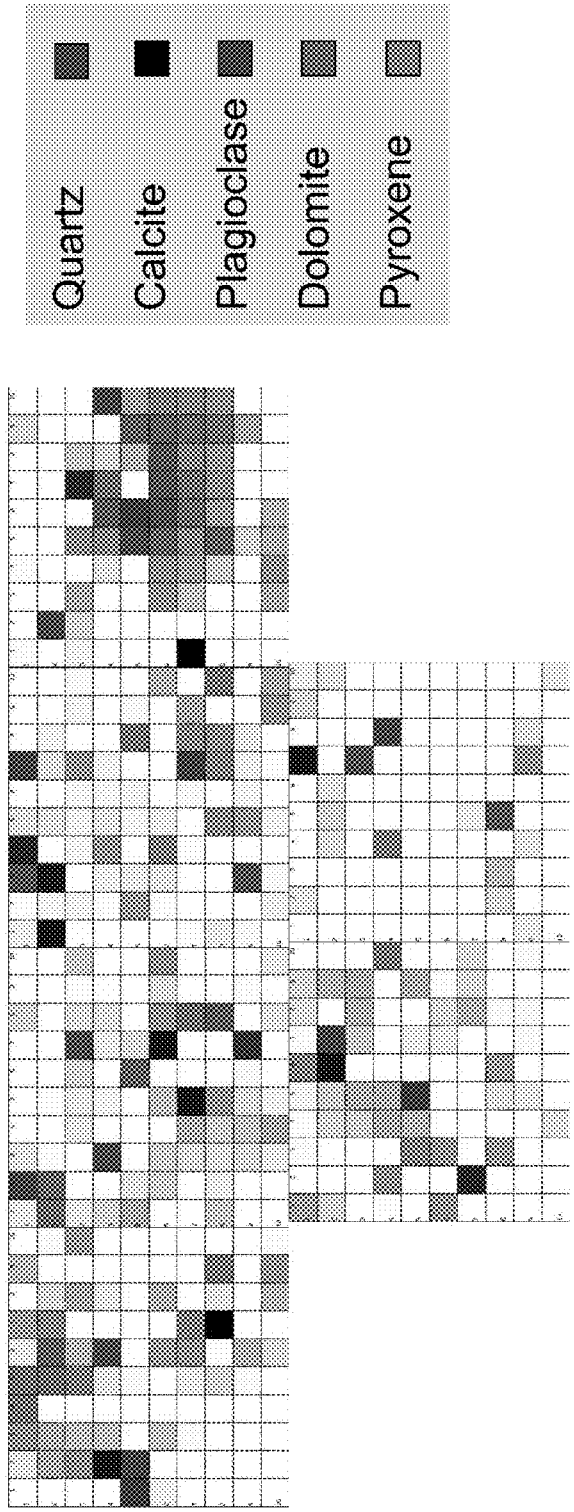
Figure 41:
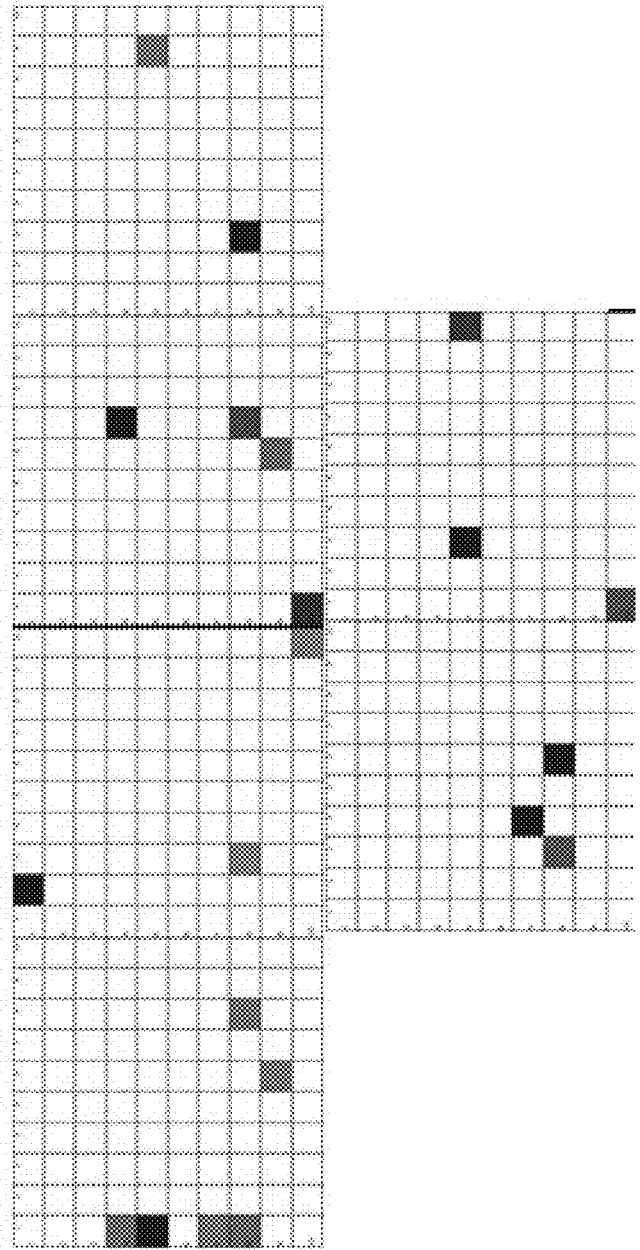
FIG. 41 shows Raman mapping of plagioclase and its concentration across an array of sampling dots on the top surface of the sliced rock sample in FIG. 39.

FIG. 41 shows concentration mapping of plagioclase across an array of sampling dots on the top surface of the sliced rock sample in FIG. 39. The mineral compositions is used to predict probability of crude oil or gas underground (step 3690). Typically, a database of historic data is stored relating to correlations between mineral compositions and known oil/gas content. The historic data can be used to predict oil content based on the mineral compositions using Raman mapping method. As comparison result, targeted mineral sample concentration in a rock sample obtained by rock surface Raman mapping shows good correlation with the results of the X-ray analyses.

It should be noted that the disclosed Raman spectral analysis of mineral compositions in rock samples is not limited to sliced rock samples; it can also be applied to powder rock samples.

It should also be noted that the disclosed Raman spectral analysis of mineral compositions in rock samples has been found to correlate with conventional GC method very well. However, similar to the surface-enhanced Raman analysis method disclosed above, the disclosed Raman spectral analysis of mineral compositions in rock samples can be conducted much faster than conventional testing techniques: for example, a conventional X-ray measurement may take days to finish while the presently disclosed methods usually only take minutes. The presently disclosed method is thus more convenient (in field) and lower cost to implement.

Predict Probability of Crude Oil or Gas Underground by Analyzing Drilling Sample and Rock Samples It should also be noted that the disclosed Raman spectral analysis of mineral compositions in rock samples (FIG. 36) and the surface-enhanced Raman analysis of substances in drilling samples (FIG. 30) can be combined. Both methods can be implemented in the field. Correlation of the results from the two disclosed methods can improve accuracy and confidence in determining the presence as well as concentrations of oil or gas underground.

The combined method for predicting presence of crude oil or gas underground can include one or more of the following steps: first, a drilling sample and a sliced rock sample are obtained from a same geological location. They can be obtained from a same drilling hole, or from different drilling holes. The drilling sample (typically in a fluid or mud form) is introduced into a sample solution containing nano particles. The sample solution comprising the drilling sample and the nano particles is illuminated by a first laser beam emitted by a probe (usually in the field). The probe collects light scattered by the drilling sample and the nano particles in the sample solution. A first Raman spectrum is obtained from the light scattered by the drilling sample and the nano particles in the sample solution. A spectral signature associated with a substance is identified around a predetermined Raman shift in the first Raman spectrum. The substance is known to be present in crude oil or gas. Crude oil or gas content is determined in the drilling sample based on the spectral signature of the substance in the first Raman spectrum. Similarly, the surface of the sliced rock sample is illuminated by a second laser beam. The second laser beam can be produced by the same probe. Light scattered by the surface of the sliced rock sample at each of the sample dots is collected. A second Raman spectrum is obtained from the light scattered from the surface of the sliced rock sample at each of sample dots. A mineral content is determined at each of the sample dots on the surface of the sliced rock sample based on the second Raman spectrum. A probability of crude oil or gas underground is predicted based on the mineral content and the crude oil or gas content in the drilling sample.

Monitoring Network System for Detecting Oil Content in Drilling Samples and Mineral Compositions in Rock Samples in the Field In some embodiments, referring to FIGS. 26-27, 30, 36, the processes shown in FIGS. 30 and 36 can be implemented by the monitoring network system 2600. The presently disclosed mobile detector 2620 is deployed near the drilling holes where the drilling samples and rock samples are extracted from underground. The probe 2621 (i.e. probe 3150 in FIG. 31) emits laser incident light to illuminate a sample solution (3120 in FIG. 31) comprising nano particles and the drilling sample, or the surface of a sliced rock sample (e.g. as shown in FIG. 39). The probe 2621 also collects light scattered by the sample solution or the surface the sliced rock sample. Raman spectrum is obtained by the spectrometer 2740 in the mobile detector 2620.

In some embodiments, one or more mobile detectors 2620 can be installed inside a drilling hole underground to provide real-time, in-field, and "in-depth" (literally and metaphorically) monitoring of the chemical content of the substance in the drilling hole. The mobile detectors 2620 can be connected the network using durable cables which can hold data and power lines, a wireless method. Different mobile detectors 2620 can be installed at different depths underground to enable real-time data at different drilling depths as exemplified by FIG. 34. The steps of illuminating the sample and collecting light from the sample are conducted by a mobile detector 2620 in the drilling hole underground. Optionally, Raman spectra are also obtained in the drilling hole underground. The Raman spectral data is transmitted electronically from underground to the equipment and network above ground.

The spectral data can be analyzed in the mobile detector 2620, or can be transmitted the central office 2610 for analyses. As described above, the analyses can involve identifying spectral signatures of certain substances that is rich in oil or gas, or identifying spectral signatures of certain minerals. The analyses can further include comparing to predetermined thresholds for the substances to predict oil or gas with confidence. The analyses can also include comparing to measured mineral compositions in the rock sample to a predetermined range to reliably predict oil or gas underground. The analyses algorithms, the thresholds, and the predetermined ranges can be stored locally in the mobile detector 2620, or can be stored in the database 2670 and executed by the server 2640 in the central office 2610.

One advantage of the presently disclosed methods is that by providing testing in the field, feedback and guidance can be provided almost real time to the drilling strategies in the field. For example, if a drilling hole or rock core show promising oil/gas content at different depths underground (e.g. by analyzing Raman spectral signatures at different depths of the drilling holes as shown in FIG. 34), more drilling can be done at different depths or in the adjacent areas to explore detailed scope of the oil and gas deposits underground. If the in-field testing result is not promising at a location, the drilling team can quickly move on to the next location. Thus, the entire drilling exploration is made more efficient by the presently disclosed methods.

Another advantage of the presently disclosed methods is that the central office can instantaneously monitor testing results from multiple locations in the field, which allows the monitoring network system 2600 to have a global picture for potential oil and gas deposits in a large geological area.

In should understood that the foregoing description and examples, limited and narrow interpretation of descriptive language intended to better illustrate the invention is not to be construed as limiting in any way nor to limit the scope of the invention contemplated by the inventor. It will be clear that the invention may be practiced otherwise than as particularly described in the foregoing description and examples. Numerous modifications and variations of the present invention are possible in light of the above teachings and, therefore, are within the scope of the appended claims.

What is claimed is:

1. A method for detecting crude oil or gas in a drilling sample, comprising: extracting a drilling sample from a first drilling hole in a ground; introducing the drilling sample into a sample solution containing nano particles; illuminating the sample solution comprising the drilling sample and the nano particles by a laser beam in the vicinity of the first drilling hole; collecting light scattered by the drilling sample and the nano particles in the sample solution; obtaining a Raman spectrum from the light scattered by the drilling sample and the nano particles in the sample solution; identifying, in the Raman spectrum, a spectral signature associated with a substance around a predetermined Raman shift; determining crude oil or gas content in the drilling sample based on the spectral signature of the substance in the Raman spectrum; and in response to the crude oil or gas content determined in the drilling, adjusting drilling depths or locations of one or more drilling holes in real time.

2. The method of claim 1, wherein the drilling sample is collected in a first drilling hole underground, wherein the steps of illuminating the sample solution and collecting light are conducted by a detector in the drilling hole underground.

3. The method of claim 2, wherein the substance comprises at least one of a multi-ring aromatic molecule, thiophene, dibenzothiophene, methyl dibenzothiophene, phenanthrene, methylphenanthrene, carbazole, or a homologue of aforementioned molecules, n-hexane, cyclohexane, benzene, toluene, or xylene, otctane, heptane, or nonane.

4. The method of claim 1, wherein the substance comprises aromatic molecules.

5. The method of claim 1, wherein the substance comprises nitrogen containing hydrocarbon compounds.

6. The method of claim 5, wherein the nitrogen containing hydrocarbon compounds include carbazole or homologue compound molecules of carbazole.

7. The method of claim 1, wherein the substance comprises sulfur containing hydrocarbon compounds.

8. The method of claim 7, wherein the sulfur containing hydrocarbon compounds include dibenzothiophene or homologue compound molecules of dibenzothiophene.

9. The method of claim 1, wherein the spectral signature includes at least one spectral peak around the predetermined Raman shift, the method further comprising:
determining a concentration of the substance in the drilling sample using the spectral signature.

10. The method of claim 1, further comprising:
after the step of introducing, allowing molecules in the drilling sample to adsorb to the nano particles in the sample solution.

11. The method of claim 1, wherein the sample solution comprises multi-valence ions.

12. The method of claim 1, further comprising:
introducing an ionic material into the sample solution, wherein the sample solution has an ionic concentration in a range from about 10 µM to a saturation level.

13. The method of claim 1, wherein the nano particles comprise a magnetic or ferromagnetic material.

14. The method of claim 13, further comprising:
applying an electrical field, a magnetic field, or an electromagnetic field to the sample solution during the step of collecting.

15. The method of claim 1, wherein the nano particles comprise a material selected from a group consisting of a metal, a metal alloy, an oxide material, silicon, a polymeric material, carbon nano tubes, and a combination thereof.

16. The method of claim 1, wherein the nano particles have an average dimension in a range from about 1 nm to about 10 µm.

17. The method of claim 16, wherein the nano particles have an average dimension in a range from about 5 nm to about 500 nm.

18. The method of claim 1, wherein the nano particles have a size distribution characterized by an average dimension and a width, wherein the ratio of the width to the average dimension is in a range from about 0.01 to about 3.

19. A method for predicting presence of crude oil or gas in the underground, comprising:
defining an array of sample dots on a surface of a sliced rock sample obtained from underground;
illuminating each of the sample dots on the surface of the sliced rock sample by a laser beam;
collecting light scattered by the surface of the sliced rock sample at each of the sample dots;
obtaining a Raman spectrum from the surface of the sliced rock sample at each of sample dots;
determining a mineral content at each of the sample dots on the surface of the sliced rock sample based on the Raman spectrum;
obtaining a map of mineral content on the surface of the sliced rock sample; and
predicting a probability of crude oil or gas underground using the map of mineral content.

20. The method of claim 19, further comprising:
establishing Raman spectral signatures in a plurality of minerals, wherein the step of determining a mineral content includes identifying a Raman spectral signature associated with one of the plurality of minerals in the Raman spectrum.

21. The method of claim 20, further comprising:
for at least one of the plurality of minerals, establishing a quantitative dependence of spectral intensity at one of the Raman spectral signatures as a function of the concentration of the one of the plurality of minerals, wherein the step of determining a mineral content includes calculating a concentration of the one of the plurality of minerals based on the function and spectral intensities at the spectral signature.

22. The method of claim 19, wherein the sliced rock sample is extracted from a first drilling hole in the ground, and wherein the steps of illuminating and collecting light are conducted in the vicinity of the first drilling hole.

23. The method of claim 22, further comprising:
in response to the map of mineral content on the surface of the sliced rock sample, adjusting drilling depths or locations of one or more drilling holes in real time.

24. The method of claim 19, wherein the mineral content includes one or more of Quartz, Calcite, Plagioclase, Dolomite, Pyroxene, Chlorite, Kalifeldspar, Na-feldspar, Amphibole, MuscLaumontite and analcime ovite, Biotite, Ankerite, Siderite, Anhydrite, Gypsum, Thenardite, Barite, Pyrite, Glauberite, Laumontite, Analcime, Illite, Smectite, Kaolinite, Corundum, Ankerite, Halite, Mica, Hornblende, or Granite.

25. A method for predicting presence of crude oil or gas in the underground, comprising:
receiving a drilling sample and a sliced rock sample obtained from a same geological location;
introducing the drilling sample into a sample solution containing nano particles;
illuminating the sample solution comprising the drilling sample and the nano particles by a first laser beam;
collecting light scattered by the drilling sample and the nano particles in the sample solution;
obtaining a first Raman spectrum from the light scattered by the drilling sample and the nano particles in the sample solution;
identifying, in the first Raman spectrum, a spectral signature associated with a substance around a predetermined Raman shift;
determining crude oil or gas content in the drilling sample based on the spectral signature of the substance in the first Raman spectrum;
illuminating a surface of the sliced rock sample by a second laser beam;
collecting light scattered by the surface of the sliced rock sample at each of the sample dots;
obtaining a second Raman spectrum using the light scattered from the surface of the sliced rock sample at each of sample dots;
determining a mineral content at each of the sample dots on the surface of the sliced rock sample based on the second Raman spectrum; and
predicting a probability of crude oil or gas underground using the mineral content and the crude oil or gas content in the drilling sample.

* * * * *